(12) United States Patent
Hinuma et al.

(10) Patent No.: US 7,214,495 B2
(45) Date of Patent: May 8, 2007

(54) SCREENING METHOD

(75) Inventors: Shuji Hinuma, Ibaraki (JP); Masaki Hosoya, Ibaraki (JP); Yasuaki Ito, Ibaraki (JP); Makoto Kobayashi, Hyogo (JP); Hideyuki Tanaka, Ibaraki (JP); Shoichi Ohkubo, Ibaraki (JP); Ryo Fujii, Ibaraki (JP); Hideki Kizawa, Ibaraki (JP); Yuji Kawamata, Ibaraki (JP); Kazuhiro Ogi, Ibaraki (JP); Masataka Harada, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 2 days.

(21) Appl. No.: 10/504,726

(22) PCT Filed: Feb. 13, 2003

(86) PCT No.: PCT/JP03/01483

§ 371 (c)(1),
(2), (4) Date: Aug. 13, 2004

(87) PCT Pub. No.: WO03/068959

PCT Pub. Date: Aug. 21, 2003

(65) Prior Publication Data

US 2005/0089866 A1   Apr. 28, 2005

(30) Foreign Application Priority Data

Feb. 14, 2002 (JP) .............................. 2002-037131
Jul. 12, 2002 (JP) .............................. 2002-204163
Nov. 12, 2002 (JP) .............................. 2002-328696
Jan. 22, 2003 (JP) .............................. 2003-014032

(51) Int. Cl.
   *G01N 33/566* (2006.01)

(52) U.S. Cl. ...................... 435/7.1; 435/7.21; 436/501

(58) Field of Classification Search .................... None
See application file for complete search history.

(56) References Cited

U.S. PATENT DOCUMENTS

2004/0137517 A1 * 7/2004 Andrews et al. ............. 435/7.1

FOREIGN PATENT DOCUMENTS

| WO | WO 00/22129 | 4/2000 |
| WO | WO 02/057783 A2 | 7/2002 |
| WO | WO-02/061087 | 8/2002 |
| WO | WO 02/061087 A2 | 8/2002 |

OTHER PUBLICATIONS

Sawzdargo et al, "A Cluster of Four Novel Human G Protein-Coupled Receptor Genes Occurring in Close Proximity to CD22 Gene on Chromosomes 19q13.1," *Biochemical and Biophysical Research Communications* 239:543-547 (1997).
Y. Itoh, et al., "Free fatty acids regulate insulin secretion from pancreatic β cells through GPR40", *Nature*, vol. 422, No. 6928, Mar. 13, 2003, pp. 173-176.
M. Sawzdargo, et al., "Identification and cloning of three novel human G protein-coupled receptor genes GPR52, ψGPR53 and GPR55: GPR55 is extensively expressed in human brain", *Molecular Brain Research*, vol. 64, No. 2, Feb. 5, 1999, pp. 193-198.
R. P. Robertson, "Eicosanoids as Pluripotential Modulators of Pancreatic Islet Function", *Diabetes*, vol. 37, No. 4, 1998, pp. 367-370.

* cited by examiner

*Primary Examiner*—John Ulm
(74) *Attorney, Agent, or Firm*—Edwards Angell Palmer & Dodge LLP; David G. Conlin

(57) ABSTRACT

By using (1) a G protein-coupled receptor protein having the same or substantially the same amino acid sequence as the amino acid sequence represented by SEQ ID NO: 1 or its salt and (2) a fatty acid or an eicosanoid, a compound or its salt that can change the binding properties of the receptor protein or its salt to the fatty acid or the eicosanoid can be screened efficiently.

3 Claims, 34 Drawing Sheets

FIG. 22 m40i103
(SEQ ID NO: 34) 5 CGCCAGUUGUGACAUUCUUdTdT 3
(SEQ ID NO: 35) 3 dTdTGCGGUCAACACUGUAAGAA 5 m40i256
(SEQ ID NO: 36) 5 CUUGUUAGCCAUCCGAGGCdTdT 3
(SEQ ID NO: 37) 3 dTdTGAACAATCGGTAGGCTCCG 5

SCREENING METHOD

TECHNICAL FIELD

The present invention relates to a rat, mouse, monkey and hamster-derived novel G protein-coupled receptor protein (GPR40) or its salts, and a DNA encoding said GPR40 and its use, as well as use of GPR40 including human-derived GPR40.

BACKGROUND ART

Physiological active substances such as various hormones and neurotransmitters regulate the biological function via specific receptor proteins present on cell membranes. Many of these receptor proteins are coupled with guanine nucleotide-binding protein (hereinafter sometimes simply referred to as G protein) and mediate the intracellular signal transduction via activation of G protein. These receptor proteins possess the common structure containing seven transmembrane domains and are thus collectively referred to as G protein-coupled receptors or seven-transmembrane receptors (7TMR).

G protein-coupled receptor proteins are present on the cell surface of each functional cell and organ in the body, and play important physiological roles as the target of the molecules that regulate the functions of the cells and organs, e.g., hormones, neurotransmitters, physiologically active substances and the like. Receptors transmit signals to cells via binding with physiologically active substances, and the signals induce various reactions such as activation and inhibition of the cells.

To clarify the relationship between substances that regulate complex biological functions in various cells and organs, and their specific receptor proteins, in particular, G protein-coupled receptor proteins would elucidate the functional mechanisms in various cells and organs in the body to provide a very important means for development of drugs closely associated with the functions.

For example, in various organs, their physiological functions are controlled in vivo through regulation by many hormones, hormone-like substances, neurotransmitters or physiologically active substances. In particular, physiologically active substances are found in numerous sites of the body and regulate the physiological functions through their corresponding receptor proteins. Many unknown hormones, neurotransmitters or many other physiologically active substances still exist in the body and, as to their receptor proteins, many of these proteins have not yet been reported. In addition, it is still unknown if there are subtypes of known receptor proteins.

It is very important for development of drugs to clarify the relationship between substances that regulate elaborated functions in vivo and their specific receptor proteins. Furthermore, for efficient screening of agonists and antagonists to receptor proteins in development of drugs, it is required to clarify functional mechanisms of receptor protein genes expressed in vivo and express the genes in an appropriate expression system.

In recent years, random analysis of cDNA sequences has been actively studied as a means for analyzing genes expressed in vivo. The sequences of cDNA fragments thus obtained have been registered on and published to databases as Expressed Sequence Tag (EST). However, since many ESTs contain sequence information only, it is difficult to predict their functions from the information.

The amino acid sequence of human-derived GPR40 and the DNA encoding the same are reported (WO 2000-22129 and Biochem. Biophys. Res. Commun. 1997, Oct. 20; 239 (2): 543–547).

Also, it is reported that the ligand to human-derived GPR40 is a fatty acid (WO 02/057783).

Heretofore, substances that inhibit the binding of G protein-coupled proteins to physiologically active substances (i.e., ligands) and substances that bind and induce signals similar to those physiologically active substances (i.e., ligands) have been used for pharmaceuticals as antagonists and agonists specific to the receptors that regulate the biological functions. Therefore, these substances are not only important for physiological expression in the body as stated above but discovery and cloning of its gene (e.g., cDNA) for a novel G protein-coupled receptor that can be targeted for pharmaceutical development are also very important means in search for a specific ligand, agonist, and antagonist of the novel G protein-coupled receptor.

However, not all G protein-coupled receptors have been discovered. There are unknown G protein-coupled receptors and many of these receptors in which the corresponding ligands are yet unidentified are called orphan receptors. Therefore, search and functional elucidation of a novel G protein-coupled receptor is eagerly awaited.

G protein-coupled receptors are useful in searching for a novel physiological active substance (i.e., ligand) using the signal transduction activity as an indicator and in search for agonists and antagonists of the receptor. On the other hand, even if no physiological ligand is found, agonists and antagonist of the receptor may be prepared by analyzing the physiological action of the receptor through inactivation experiment of the receptor (knockout animal). Ligands, agonists, antagonists, etc. of the receptor are expected to be used as prophylactic/therapeutic and diagnostic agents for diseases associated with dysfunction of the G protein-coupled receptor.

Attenuation or accentuation in functions of the G protein coupled receptor due to genetic aberration of the G protein-coupled receptor protein in vivo causes some disorders in many cases. In this case, the G protein coupled receptor may be used not only for administration of antagonists or agonists of the receptor, but also for gene therapy by transfer of the receptor gene into the body (or some particular organs) or by introduction of the antisense nucleic acid of the receptor gene into the body (or the particular organ). In this case, information on the base sequence of the receptor gene is essentially required for investigating deletion or mutation in the gene. The receptor gene is also applicable as prophylactic/therapeutic and diagnostic agents for diseases associated with dysfunction of the receptor.

The present invention provides a novel and useful G protein-coupled receptor protein as described above. That is, the present invention provides a novel G protein-coupled receptor protein, its partial peptides and salts thereof; polynucleotides (DNA and RNA, and derivatives thereof) containing the polynucleotides (DNA and RNA, and derivatives thereof) encoding the G protein-coupled receptor protein or its partial peptides; recombinant vectors containing the polynucleotides; transformants bearing the recombinant vectors; methods for manufacturing the G protein-coupled receptor protein or its salts; antibodies to the G protein-coupled receptor protein, its partial peptides and salts thereof; compounds that change the expression level of said G protein-coupled receptor protein; methods of determining ligands to the G protein-coupled receptor protein; methods for screening the compounds (antagonists and agonists) or salts thereof that change the binding properties of ligands and the G protein-coupled receptor protein; kits for use in the screening methods, compounds (antagonists and agonists) or salts thereof that change the binding properties of ligands obtainable by the screening methods or obtainable using the screening kits and the G protein-coupled receptor protein, or pharmaceuticals comprising the compounds (antagonists and agonists) that change the binding properties of ligands to the G protein-coupled receptor protein, or compounds or salts thereof that change the expression level of the G protein-coupled receptor protein; etc.

DISCLOSURE OF THE INVENTION

The present inventors made extensive investigations and as a result, found that ligands to human GPR40 are fatty acids or eicosanoids. Also, the inventors succeeded in cloning DNAs encoding rat, mouse and hamster-derived GPR40. Furthermore, the inventors found that GPR40 is highly expressed in pancreatic Langerhans islets, fatty acids or eicosanoids bind to GPR40 thereby to induce increased intracellular $Ca^{2+}$ level and suppressed cAMP production, and free fatty acids promote insulin secretion from MIN6 cells. In addition, the inventors acquired monoclonal antibodies to the C-terminal peptide of human GPR40 and siRNA to mouse GPR40. Based on these findings, the present inventors continued further studies and have come to accomplish the present invention.

That is, the present invention provides the following features and the like.

(1) A G protein-coupled receptor protein comprising the same or substantially the same amino acid sequence as the amino acid sequence represented by SEQ ID NO: 1, SEQ ID NO: 3, SEQ ID NO: 17 or SEQ ID NO: 29, or its salt.

(2) A G protein-coupled receptor protein comprising the same or substantially the same amino acid sequence as the amino acid sequence represented by SEQ ID NO: 1 or SEQ ID NO: 3, or its salt.

(3) A G protein-coupled receptor protein consisting of the amino acid sequence represented by SEQ ID NO: 1 or SEQ ID NO: 3, or its salt.

(4) A G protein-coupled receptor protein consisting of the amino acid sequence represented by SEQ ID NO: 17, or its salt.

(5) A G protein-coupled receptor protein consisting of the amino acid sequence represented by SEQ ID NO: 29, or its salt.

(6) A partial peptide of the G protein-coupled receptor protein according to (1), or its salt.

(7) A polynucleotide containing a polynucleotide encoding the G protein-coupled receptor protein according to (1).

(8) A DNA encoding the G protein-coupled receptor protein according to (3).

(9) A DNA encoding the G protein-coupled receptor protein according to (4).

(10) A DNA encoding the G protein-coupled receptor protein according to (5).

(11) A DNA consisting of the base sequence represented by SEQ ID NO: 2 or SEQ ID NO: 4.

(12) A DNA consisting of the base sequence represented by SEQ ID NO: 18.

(13) A DNA consisting of the base sequence represented by SEQ ID NO: 30.

(14) A recombinant vector containing the polynucleotide according to (7).

(15) A transformant transformed by the recombinant vector according to (14).

(16) A method of manufacturing the G protein-coupled receptor protein or its salt according to (1), which comprises culturing the transformant according to (15) and producing the G protein-coupled receptor protein or its salt according to (1).

(17) A pharmaceutical comprising the G protein-coupled receptor protein according to (1), the partial peptide according to (6), or a salt thereof.

(18) A pharmaceutical comprising the polynucleotide according to (7).

(19) A diagnostic product comprising the polynucleotide according to (7).

(20) An antibody to the G protein-coupled receptor protein according to (1), the partial peptide according to (6), or a salt thereof.

(21) The antibody according to (20), which is a monoclonal antibody capable of recognizing the C-terminal peptide of the G protein-coupled receptor protein according to (1) or its salt.

(22) The antibody according to (20), which is a monoclonal antibody capable of recognizing the peptide represented by SEQ ID NO: 33 or its salt.

(23) The antibody according to (20), which is a neutralizing antibody capable of inactivating signal transduction of the G protein-coupled receptor protein according to (1).

(24) A diagnostic product comprising the antibody according to (20).

(25) A pharmaceutical comprising the antibody according to (20).

(26) A polynucleotide containing a base sequence complementary to the polynucleotide according to (7), or a part of the base sequence.

(27) A diagnostic product comprising the polynucleotide according to (26).

(28) A pharmaceutical comprising the polynucleotide according to (26).

(29) A siRNA to the polynucleotide according to (7).

(30) The siRNA according to (29), which is siRNA constructed by a sense strand consisting of the base sequence represented by SEQ ID NO: 34 and an antisense strand consisting of the base sequence represented by SEQ ID NO: 35.

(31) The siRNA according to (29), which is siRNA constructed by a sense strand consisting of the base sequence represented by SEQ ID NO: 36 and an antisense strand consisting of the base sequence represented by SEQ ID NO: 37.

(32) A diagnostic product comprising the siRNA according to (29).

(33) A pharmaceutical comprising the siRNA according to (29).

(34) A pancreatic function regulating agent comprising a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, its partial peptide, or a salt thereof.

(35) A preventive/therapeutic agent for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory and learning, which comprises a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, its partial peptide, or a salt thereof.

(36) An insulin secretion promoting agent or hypoglycemic agent comprising a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, its partial peptide, or a salt thereof.

(37) A pancreatic β cell protecting agent comprising a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, its partial peptide, or a salt thereof.

(38) A pancreatic function regulating agent, which comprises a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide.

(39) A preventive/therapeutic agent for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory and learning, which comprises a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide.

(40) An insulin secretion promoting agent or hypoglycemic agent, which comprises a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide.

(41) A pancreatic β cell protecting agent, which comprises a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide.

(42) A diagnostic product for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory and learning, obesity, hyperlipemia, hypoglycemia, hypertension, edema, insulin resistance syndrome, unstable diabetes, fatty atrophy, insulin allergy, insulinoma, lipotoxicity or cancer, which comprises a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide.

(43) A diagnostic product for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory and learning, obesity, hyperlipemia, hypoglycemia, hypertension, edema, insulin resistance syndrome, unstable diabetes, fatty atrophy, insulin allergy, insulinoma, lipotoxicity or cancer, which comprises an antibody to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, its partial peptide, or a salt thereof.

(44) A pancreatic function regulating agent, comprising an antibody to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, its partial peptide, or a salt thereof.

(45) A preventive/therapeutic agent for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, which comprises an antibody to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, its partial peptide, or a salt thereof.

(46) A pancreatic function regulating agent comprising a polynucleotide containing a base sequence complementary to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a part of the base sequence.

(47) A preventive/therapeutic agent for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, which comprises a polynucleotide containing a base sequence complementary to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a part of the base sequence.

(48) A method of screening a compound or its salt that changes the binding properties of a G protein-coupled receptor protein containing the same or substantially the same amino acid sequence represented by SEQ ID NO: 1, SEQ ID NO: 3, SEQ ID NO: 5, SEQ ID NO: 17 or SEQ ID NO: 29 or its salt to a fatty acid or its salt, which comprises using (1) the G protein-coupled receptor protein or its partial peptide, or a salt thereof and (2) the fatty acid or its salt.

(49) A kit for screening a compound or its salt that changes the binding properties of a G protein-coupled receptor protein containing the same or substantially the same amino acid sequence represented by SEQ ID NO: 1, SEQ ID NO: 3, SEQ ID NO: 5, SEQ ID NO: 17 or SEQ ID NO: 29 or its salt to a fatty acid or its salt, comprising (1) the G protein-coupled receptor protein, its partial peptide, or a salt thereof and (2) the fatty acid or its salt.

(50) A compound or its salt that changes the binding properties of a fatty acid or its salt to a G protein-coupled receptor protein containing the same or substantially the same amino acid sequence represented by SEQ ID NO: 1, SEQ ID NO: 3, SEQ ID NO: 5, SEQ ID NO: 17 or SEQ ID NO: 29 or its salt, which is obtainable by using the screening method according to (48) or the screening kit according to (49).

(51) The compound or its salt according to (50), which is an agonist.

(52) The compound or its salt according to (50), which is an antagonist.

(53) A pharmaceutical comprising the compound or its salt according to (50).

(54) A pancreatic function regulating agent comprising a compound or its salt that changes the binding properties of a fatty acid or its salt to a G protein-coupled receptor protein containing the same or substantially the same amino acid sequence represented by SEQ ID NO: 1, SEQ ID NO: 3, SEQ ID NO: 5, SEQ ID NO: 17 or SEQ ID NO: 29, or its salt.

(55) A pharmaceutical comprising the agonist according to (51).

(56) A preventive/therapeutic agent for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory and learning, which comprises an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its salt.

(57) An insulin secretion promoting agent or hypoglycemic agent comprising an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its salt.

(58) A pancreatic β cell protecting agent comprising an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its salt.

(59) A pharmaceutical comprising the antagonist according to (52).

(60) A preventive/therapeutic agent for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, which comprises an antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its salt.

(61) A method of screening a compound or its salt having an action of changing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 to regulate pancreatic functions, which comprises using a polynucleotide containing a polynucleotide encoding the G protein-coupled receptor protein or its partial peptide.

(62) A kit for screening a compound or its salt having an action of changing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 to regulate pancreatic functions, comprising a polynucleotide containing a polynucleotide encoding the G protein-coupled receptor protein or its partial peptide.

(63) A compound or its salt having an action of changing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions, which is obtainable by using the screening method according to (61) or the screening kit according to (62).

(64) A compound or its salt having an action of increasing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions, which is obtainable by using the screening method according to (61) or the screening kit according to (62).

(65) A compound or its salt having an action of decreasing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions, which is obtainable by using the screening method according to (61) or the screening kit according to (62).

(66) A pancreatic function regulating agent comprising a compound or its salt having an action of changing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions.

(67) A preventive/therapeutic agent for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, which comprises a compound or its salt having an action of increasing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions.

(68) An insulin secretion promoting agent or hypoglycemic agent comprising a compound or its salt having an action of increasing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions.

(69) A pancreatic β cell protecting agent comprising a compound or its salt having an action of increasing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions.

(70) A preventive/therapeutic agent for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, which comprises a compound or its salt having an action of decreasing the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide to regulate pancreatic functions.

(71) A method of determining a ligand to a G protein-coupled receptor protein containing the same or substantially the same amino acid sequence represented by SEQ ID NO: 1, SEQ ID NO: 3, SEQ ID NO: 5, SEQ ID NO: 17 or SEQ ID NO: 29 or its salt, which comprises assaying the intracellular $Ca^{2+}$ level increasing activity or intracellular cAMP inhibitory activity when a test compound is brought in contact with a cell containing the receptor protein.

(72) A ligand, which is obtained by the determination method according to (71).

(73) A method of screening an agonist or antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which comprises using (1) the G protein-coupled receptor protein or its partial peptide, or a salt thereof and (2) (i) a fatty acid or its salt or (ii) a compound or its salt that changes the binding properties of the receptor protein or its salt to a fatty acid or its salt.

(74) The screening method according to (73), wherein the binding amount of (i) a labeled form of the fatty acid or its salt or (ii) a labeled form of the compound or its salt that changes the binding properties of the receptor protein or its salt to the fatty acid or its salt, to the receptor protein, its partial peptide, or a salt thereof is measured, (1) when (i) the labeled form of the fatty acid or its salt or (ii) the labeled form of the compound or its salt that changes the binding properties of the receptor protein or its salt to the fatty acid or its salt is brought in contact with the receptor protein, its partial peptide, or a salt thereof and (2) when a test compound and (i) the labeled form of the fatty acid or its salt or (ii) the labeled form of the compound or its salt that changes the binding properties of the receptor protein or its salt to the fatty acid or its salt are brought in contact with the receptor protein, its partial peptide, or a salt thereof.

(75) The screening method according to (73), wherein the binding amount of (i) a labeled form of the fatty acid or its salt or (ii) a labeled form of the compound or its salt that changes the binding properties of the receptor protein or its salt to the fatty acid or its salt, to a cell containing the receptor protein or a membrane fraction of the cell is measured, (1) when (i) the labeled form of the fatty acid or its salt or (ii) the labeled form of the compound or its salt that changes the binding properties of the receptor protein or its salt to the fatty acid or its salt is brought in contact with the cell containing the receptor protein or a membrane fraction of the cell and (2) when a test compound and (i) the labeled form of the fatty acid or its salt or (ii) the labeled form of the compound or its salt that changes the binding properties of the receptor protein or its salt to the fatty acid or its salt are brought in contact with the cell containing the receptor protein or a membrane fraction of the cell.

(76) The screening method according to (73), wherein the intracellular $Ca^{2+}$ level increasing activity or the intracellular cAMP production suppressing activity is assayed, (1) when (i) the fatty acid or its salt or (ii) the compound or its salt that changes the binding properties of the receptor protein or its salt to the fatty acid or its salt is brought in contact with a cell containing the receptor protein or a membrane fraction of the cell and (2) when a test compound and (i) the fatty acid or its salt or (ii) the compound or its salt that changes the binding properties of the receptor protein or its salt to the fatty acid or its salt are brought in contact with the cell containing the receptor protein or a membrane fraction of the cell.

(77) A kit for screening an agonist or antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which comprises (1) the receptor protein, its partial peptide, or a salt thereof and (2) (i) a fatty acid or its salt or (ii) a compound or its salt that changes the binding properties of the receptor protein or its salt to a fatty acid or its salt.

(78) An agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which is obtainable by using the screening method according to (73) or the screening kit according to (77).

(79) An antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which is obtainable by using the screening method according to (73) or the screening kit according to (77).

(80) A pharmaceutical comprising the agonist according to (78).

(81) A pharmaceutical comprising the antagonist according to (79).

(82) The screening method according to (74) through (76), wherein the test compound is a compound designed to bind, based on the atomic coordinate and the position of the ligand-binding pocket in the active site of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, to the ligand-binding pocket.

(83) A method for confirmation that (i) a pancreatic function regulating drug, (ii) a preventive/therapeutic drug for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, (iii) an insulin secretion promoting drug, (iv) a hypoglycemic drug, (v) a pancreatic β cell protecting drug or (vi) a preventive/therapeutic drug for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, binds to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its salt, which comprises using the receptor protein or its salt.

(84) A method for confirmation that (i) a preventive/therapeutic drug for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, (ii) an insulin secretion promoting drug, (iii) a hypoglycemic drug or (iv) a pancreatic β cell protection is an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its salt, which comprises using the receptor protein or its salt.

(85) A method for confirmation that a preventive/therapeutic drug for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer is an antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its salt, which comprises using the receptor protein or its salt.

(86) The method for confirmation according to (83) through (85), wherein the binding amount of each drug to the receptor protein, its partial peptide, or a salt thereof is measured when each drug is brought in contact with the receptor protein or its partial peptide, or a salt thereof.

(87) The method for confirmation according to (83) through (85), wherein the binding amount of (i) a labeled form of the fatty acid or its salt or (ii) a labeled form of the compound or its salt that changes the binding properties of the receptor protein or its salt to the fatty acid or its salt, to the receptor protein, its partial peptide, or a salt thereof is measured, (1) when (i) the labeled form of the fatty acid or its salt or (ii) the labeled form of the compound or its salt is brought in contact with the receptor protein, its partial peptide, or a salt thereof, and (2) when each drug and (i) the labeled form of the fatty acid or its salt or (ii) the labeled form of the compound or its salt are brought in contact with the receptor protein, its partial peptide, or a salt thereof.

(88) The method for confirmation according to (83) through (85), wherein the binding amount of (i) a labeled form of the fatty acid or its salt or (ii) a labeled form of the compound or its salt that changes the binding properties of the receptor protein or its salt to the fatty acid or its salt to a cell containing the receptor protein or a membrane fraction of the cell is measured, (1) when (i) the labeled form of the fatty acid or its salt or (ii) the labeled form of the compound or its salt is brought in contact with the cell containing the receptor protein or a membrane fraction of the cell and (2) when each drug and (i) the labeled form of the fatty acid or its salt or (ii) the labeled form of the compound or its salt are brought in contact with the cell containing the receptor protein or a membrane fraction of the cell.

(89) The method for confirmation according to (83) through (85), wherein the intracellular $Ca^{2+}$ level increasing activity or the intracellular cAMP production suppressing activity is assayed, (1) when (i) the fatty acid or its salt or (ii) the compound or its salt that changes the binding properties of the receptor protein or its salt to the fatty acid or its salt is brought in contact with a cell containing the receptor protein or a membrane fraction of the cell and (2) when each drug and (i) the fatty acid or its salt or (ii) the compound or its salt that changes the binding properties of the receptor protein or its salt to the fatty acid or its salt are brought in contact with the cell containing the receptor protein or a membrane fraction of the cell.

(90) A kit for confirmation that (i) pancreatic function regulating drug, (ii) a preventive/therapeutic drug for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, (iii) an insulin secretion promoting drug, (iv) a hypoglycemic drug, (v) a pancreatic β cell protecting drug or (vi) a preventive/therapeutic drug for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer binds to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which comprises the receptor protein or its partial peptide, or a salt thereof.

(91) (i) A pancreatic function regulating drug, (ii) a preventive/therapeutic drug for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, (iii) an insulin secretion promoting drug, (iv) a hypoglycemic drug, (v) a pancreatic β cell protecting drug or (vi) a preventive/therapeutic drug for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, which is an agonist or antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29.

(92) A pharmaceutical comprising the combination of:
(1) (i) an agonist or antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or/and (ii) a compound or its salt that changes the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29, or its partial peptide; and, (2) (i) a pancreatic function regulating drug, (ii) a preventive/therapeutic drug for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, (iii) an insulin secretion promoting drug, (iv) a hypoglycemic drug, (v) a pancreatic β cell protecting drug or (vi) a preventive/therapeutic drug for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer.

(93) A non-human mammal bearing an exogenous DNA encoding the G protein-coupled receptor protein according to (1) or its variant DNA.

(94) The mammal according to (93), wherein the non-human mammal is a rodent.

(95) The mammal according to (94), wherein the rodent is mouse or rat.

(96) A non-human mammalian embryonic stem cell, in which a DNA encoding the G protein-coupled receptor protein according to (1) is inactivated.

(97) The embryonic stem cell according to (96), wherein the DNA is inactivated by introducing a reporter gene.

(98) The embryonic stem cell according to (96), which is resistant to neomycin.

(99) The embryonic stem cell according to (96), wherein the non-human mammal is a rodent.

(100) The embryonic stem cell according to (99), wherein the rodent is mouse.

(101) A non-human mammal deficient in expressing the DNA encoding the G protein-coupled receptor protein according to (1), wherein the DNA is inactivated.

(102) The non-human mammal according to (101), wherein the DNA is inactivated by inserting a reporter gene therein and the reporter gene is capable of being expressed under control of a promoter for the DNA.

(103) The non-human mammal according to (101), wherein the non-human mammal is a rodent.

(104) The non-human mammal according to (103), wherein the rodent is mouse.

(105) A method of screening a compound or its salt that promotes or inhibits the promoter activity to a DNA encoding the G protein-coupled receptor protein according to (1), which comprises administering a test compound to the mammal according to (102) and detecting expression of the reporter gene.

(106) A method of screening a compound or its salt that changes the binding properties of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt and an eicosanoid, which comprises using (1) the receptor protein, its partial peptide, or a salt thereof and (2) the eicosanoid.

(107) A kit for screening a compound or its salt that changes the binding properties of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt and an eicosanoid, comprising (1) the receptor protein, its partial peptide, or a salt thereof and (2) the eicosanoid.

(108) A compound or its salt that changes the binding properties of an eicosanoid and a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which is obtainable by using the screening method according to (106) or the screening kit according to (107).

(109) The compound or its salt according to (108), which is an agonist.

(110) The compound or its salt according to (108), which is an antagonist.

(111) A pharmaceutical comprising the compound or its salt according to (108).

(112) A pancreatic function regulating agent comprising a compound or its salt that changes the binding properties of an eicosanoid to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt.

(113) A pharmaceutical comprising the agonist according to (109).

(114) A pharmaceutical comprising the antagonist according to (110).

(115) A method of screening an agonist or antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which comprises using (1) the receptor protein or its partial peptide, or a salt thereof and (2) (i) an eicosanoid or (ii) a compound or its salt that changes the binding properties of the receptor protein or it salt to the eicosanoid.

(116) The screening method according to (115), wherein the binding amount of (i) a labeled form of eicosanoid or (ii) a labeled form of the compound or its salt that changes the binding properties of the receptor protein or its salt to the eicosanoid, to the receptor protein, its partial peptide, or a salt thereof is measured, (1) when (i) the labeled form of the eicosanoid or (ii) the labeled form of the compound or its salt that changes the binding properties of the receptor protein or its salt to the eicosanoid is brought in contact with the receptor protein or its partial peptide, or a salt thereof and (2) when a test compound and (i) the labeled form of the the eicosanoid or (ii) the labeled form of the compound or its salt that changes the binding properties of the receptor protein or its salt to the eicosanoid are brought in contact with the receptor protein or its partial peptide, or a salt thereof.

(117) The screening method according to (115), wherein the binding amount of (i) a labeled form of the eicosanoid or (ii) a labeled form of the compound or its salt that changes the binding properties of the receptor protein or its salt to the eicosanoid, to a cell containing the receptor protein or a membrane fraction of the cell is measured, (1) when (i) the labeled form of the eicosanoid or (ii) the labeled form of the compound or its salt that changes the binding properties of the receptor protein or its salt to the eicosanoid is brought in contact with the cell containing the receptor protein or a membrane fraction of the cell and (2) when a test compound and (i) the labeled form of the eicosanoid or (ii) the labeled form of the compound or its salt that changes the binding properties of the receptor protein or its salt to the eicosanoid are brought in contact with the cell containing the receptor protein or a membrane fraction of the cell.

(118) The screening method according to (115), wherein the intracellular $Ca^{2+}$ level increasing activity or the intracellular cAMP production suppressing activity is assayed, (1) when (i) the eicosanoid or (ii) the compound or its salt that changes the binding properties of the receptor protein or its salt to the eicosanoid is brought in contact with a cell containing the receptor protein or a membrane fraction of the cell and (2) when a test compound and (i) the eicosanoid or (ii) the compound or its salt that changes the binding properties of the receptor protein or its salt to the eicosanoid are brought in contact with the cell containing the receptor protein or a membrane fraction of the cell.

(119) A kit for screening an agonist or antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, comprising (1) the receptor protein or its partial peptide, or a salt thereof and (2) (i) an eicosanoid or (ii) a compound or its salt that changes the binding properties of the receptor protein or its salt to the eicosanoid.

(120) An agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which is obtainable by using the screening method according to (115) or the screening kit according to (119).

(121) An antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, which is obtainable by using the screening method according to (115) or the screening kit according to (119).

(122) A pharmaceutical comprising the agonist according to (120).

(123) A pharmaceutical comprising the antagonist according to (121).

(124) The screening method according to (116) through (118), wherein the test compound is a compound designed to bind, based on the atomic coordinate and the position of the ligand-binding pocket in the active site of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its salt, to the ligand-binding pocket.

(125) A method of regulating pancreatic functions, which comprises administering to a mammal an effective dose of:
(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;
(2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;
(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or
(4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide.

(126) A method of preventing/treating diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, which comprises administering to a mammal an effective dose of:
(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;
(2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;
(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or
(4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide.

(127) A method of promoting insulin secretion or reducing blood sugar, which comprises administering to a mammal an effective dose of:
(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;
(2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;
(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or (4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide.

(128) A pancreatic β cell protecting agent, which comprises administering to a mammal an effective dose of:

(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof, (2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or (4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide.

(129) A method of regulating pancreatic functions, which comprises administering to a mammal an effective dose of:

(1) an antibody to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a base sequence complementary to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a part of the base sequence;

(3) a siRNA to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(4) an antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (5) a compound or its salt that decreases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide.

(130) A method of preventing/treating obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, which comprises administering to a mammal an effective dose of:

(1) an antibody to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a base sequence complementary to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a part of the base sequence;

(3) a siRNA to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(4) an antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (5) a compound or its salt that decreases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide.

(131) Use of:

(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, to manufacture a pancreatic function regulating agent.

(132) Use of:

(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, to manufacture a preventive/therapeutic agent for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory.

(133) Use of:

(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, to manufacture an insulin secretion promoting agent or hypoglycemic agent.

(134) Use of:

(1) a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(3) an agonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (4) a compound or its salt that increases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, to manufacture a pancreatic β cell protecting agent.

(135) Use of:

(1) an antibody to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a base sequence complementary to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a part of the base sequence;

(3) a siRNA to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(4) an antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (5) a compound or its salt that decreases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, to manufacture a pancreatic function regulating agent.

(136) Use of:

(1) an antibody to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a salt thereof;

(2) a polynucleotide containing a base sequence complementary to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, or a part of the base sequence;

(3) a siRNA to a polynucleotide containing a polynucleotide encoding a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide;

(4) an antagonist to a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29; or, (5) a compound or its salt that decreases the expression level of a G protein-coupled receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29 or its partial peptide, to manufacture a preventive/therapeutic agent for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer.

The present invention further provides the following features and the like.

(137) The protein according to (1), which is a protein containing a) the amino acid sequence represented by SEQ ID NO: 1, SEQ ID NO: 3, SEQ ID NO: 17 or SEQ ID NO: 29 or the amino acid sequence wherein at least 1 or 2 (preferably approximately 1 to 30, more preferably approximately 1 to 10 and most preferably several (1 to 5)) amino acids are deleted in the amino acid sequence represented by SEQ ID NO: 1, SEQ ID NO: 3, SEQ ID NO: 17 or SEQ ID NO: 29; b) the amino acid sequence wherein at least 1 or 2 (preferably approximately 1 to 30, more preferably approximately 1 to 10 and most preferably several (1 to 5)) amino acids are added to the amino acid sequence represented by SEQ ID NO: 1, SEQ ID NO: 3, SEQ ID NO: 17 or SEQ ID NO: 29; c) the amino acid sequence wherein at least 1 or 2 (preferably approximately 1 to 30, more preferably approximately 1 to 10 and most preferably several (1 to 5)) amino acids in the amino acid sequence represented by SEQ ID NO: 1, SEQ ID NO: 3, SEQ ID NO: 17 or SEQ ID NO: 29 are substituted by other amino acids; or d) a combination of these amino acid sequences.

(138) The screening method according to (48), wherein comparison is made between the cases (i) where the G protein-coupled receptor protein containing the same or substantially the same amino acid sequence as the amino acid sequence represented by SEQ ID NO: 1, SEQ ID NO: 3, SEQ ID NO: 17 or SEQ ID NO: 29 (hereinafter merely referred to as GPR40) or its partial peptide, or a salt thereof is brought in contact with the fatty acid or its salt and (ii) where GPR40 or its partial peptide, or a salt thereof is brought in contact with the fatty acid or its salt and a test compound.

(139) The screening method according to (48), wherein the binding amount of a labeled form of the fatty acid or its salt to GPR40 or its partial peptide, or a salt thereof is measured and compared in the cases (i) where the labeled form of the fatty acid or its salt is brought in contact with the GPR40 or its partial peptide, or a salt thereof and (ii) where the labeled form of the fatty acid or its salt and a test compound are brought in contact with the GPR40 or its partial peptide, or a salt thereof.

(140) The screening method according to (48), wherein the binding amount of a labeled form of the fatty acid or its salt to a cell containing GPR40 is measured and compared in the cases (i) where the labeled form of the fatty acid or its salt is brought in contact with the cell containing GPR40 and (ii) where the labeled form of the fatty acid or its salt and a test compound are brought in contact with the cell containing GPR40.

(141) The screening method according to (48), wherein the binding amount of a labeled form of the fatty acid or its salt to a membrane fraction of a cell containing GPR40 is measured and compared in the cases (i) where the labeled form of the fatty acid or its salt is brought in contact with the membrane fraction of the cell containing GPR40 and (ii) where the labeled form of the fatty acid or its salt and a test compound are brought in contact with the membrane fraction of the cell containing GPR40.

(142) The screening method according to (48), wherein the binding amount of a labeled form of the fatty acid or its salt to GPR40 is measured and compared in the cases (i) where the labeled form of the fatty acid or its salt is brought in contact with GPR40, which is expressed on the cell membrane by culturing a transformant transformed with a recombinant vector bearing DNA containing a DNA encoding GPR40, and (ii) where the labeled form of the fatty acid or its salt and a test compound are brought in contact with GPR40 expressed on the cell membrane of the transformant.

(143) The screening method according to (48), wherein the cell stimulating activities mediated by GPR40 are assayed in and compared between the cases (i) where a compound that activates GPR40 is brought in contact with a cell containing GPR40 and (ii) where the compound that activates GPR40 and a test compound are brought in contact with the cell containing GPR40.

(144) The screening method according to (48), wherein the cell stimulating activities mediated by GPR40 are assayed in and compared between the case where a compound that activates GPR40 is brought in contact with GPR40 expressed on the cell membrane by culturing a transformant transformed with a recombinant vector bearing a DNA containing a DNA encoding GPR40 and the case where the compound that activates GPR40 and a test compound are brought in contact with GPR40 expressed on the cell membrane of the transformant.

(145) The screening method according to (143) or (144), wherein the compound that activates GPR40 is a fatty acid or its salt.

(146) The screening kit according to (49), which comprises containing a cell containing GPR40 or its membrane fraction.

(147) The screening kit according to (49), which comprises containing GPR40 expressed on the cell membrane of the transformant by culturing a transformant transformed with a recombinant vector bearing a DNA containing the DNA encoding GRP40.

(148) The screening method according to (106), wherein comparison is made between the cases (i) where the G protein-coupled receptor protein containing the same or substantially the same amino acid sequence as the amino acid sequence represented by SEQ ID NO: 1, SEQ ID NO: 3, SEQ ID NO: 17 or SEQ ID NO: 29 (hereinafter merely referred to as GPR40) or its partial peptide, or a salt thereof is brought in contact with the eicosanoid and (ii) GPR40 or its partial peptide, or a salt thereof is brought in contact with the eicosanoid and a test compound.

(149) The screening method according to (106), wherein the binding amount of a labeled form of the eicosanoid to GPR40 is measured in and compared between the cases (i) where a labeled form of the eicosanoid is brought in contact with GPR40 or its partial peptide, or a salt thereof and (ii) where the labeled form of the eicosanoid and a test compound are brought in contact with GPR40 or its partial peptide, or a salt thereof.

(150) The screening method according to (106), wherein the binding amount of a labeled form of the eicosanoid to a cell containing GPR40 is measured in and compared between the cases (i) where a labeled form of the eicosanoid is brought in contact with the cell containing GPR40 and (ii) where the labeled form of the eicosanoid and a test compound are brought in contact with the cell containing GPR40.
(151) The screening method according to (106), wherein the binding amount of a labeled form of the eicosanoid to a membrane fraction of a cell containing GPR40 is measured in and compared between the cases (i) where a labeled form of the eicosanoid is brought in contact with the membrane fraction of the cell containing GPR40 and (ii) where the labeled form of the eicosanoid and a test compound are brought in contact with the membrane fraction of the cell containing GPR40.
(152) The screening kit according to (106), wherein the binding amount of a labeled form of the eicosanoid to GPR40 is measured in and compared between the cases (i) where the labeled form of the eicosanoid is brought in contact with GPR40 expressed on the cell membrane by culturing a transformant transformed with a recombinant vector bearing a DNA containing a DNA encoding GPR40 and (ii) where t the labeled form of the eicosanoid and a test compound are brought in contact with GPR40 expressed on the cell membrane of the transformant.
(153) The screening method according to (106), wherein the cell stimulating activities mediated by GPR40 are assayed in and compared between the cases (i) where a compound that activates GPR40 is brought in contact with a cell containing GPR40 and (ii) where the compound that activates GPR40 and a test compound are brought in contact with the cell containing GPR40.
(154) The screening method according to (106), wherein the cell stimulating activities mediated by GPR40 are assayed in and compared between the cases where a compound that activates GPR40 is brought in contact with GPR40 expressed on the cell membrane by culturing a transformant transformed with a recombinant vector bearing a DNA containing a DNA encoding GPR40 and where the compound that activates GPR40 and a test compound are brought in contact with GPR40 expressed on the cell membrane of the transformant.
(155) The screening method according to (153) or (154), wherein the compound that activates GPR40 is an eicosanoid.
(156) The screening kit according to (107), which comprises containing the cell containing GPR40 or its membrane fraction.
(157) The screening kit according to (107), which comprises containing GPR40 expressed on the cell membrane of a transformant by culturing the transformant transformed with a recombinant vector bearing a DNA containing a DNA encoding GRP40.

BRIEF DESCRIPTION OF THE DRAWINGS

FIG. 22 shows the sequences of m40i103 (SEQ ID NO: 34 and SEQ ID NO. 35) and m40i256 (SEQ ID NO: 36 and SEQ ID NO: 37).

BEST MODE FOR CARRYING OUT THE INVENTION

Figure 1:
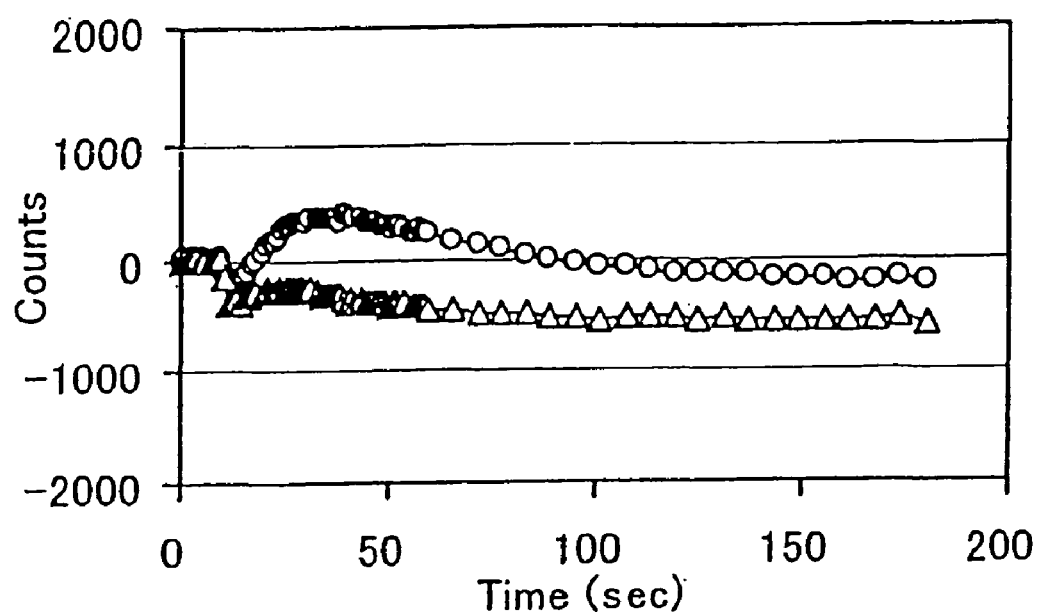
FIG. 1 shows the results of changes in intracellular $Ca^{2+}$ level examined when farnesoic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 2:
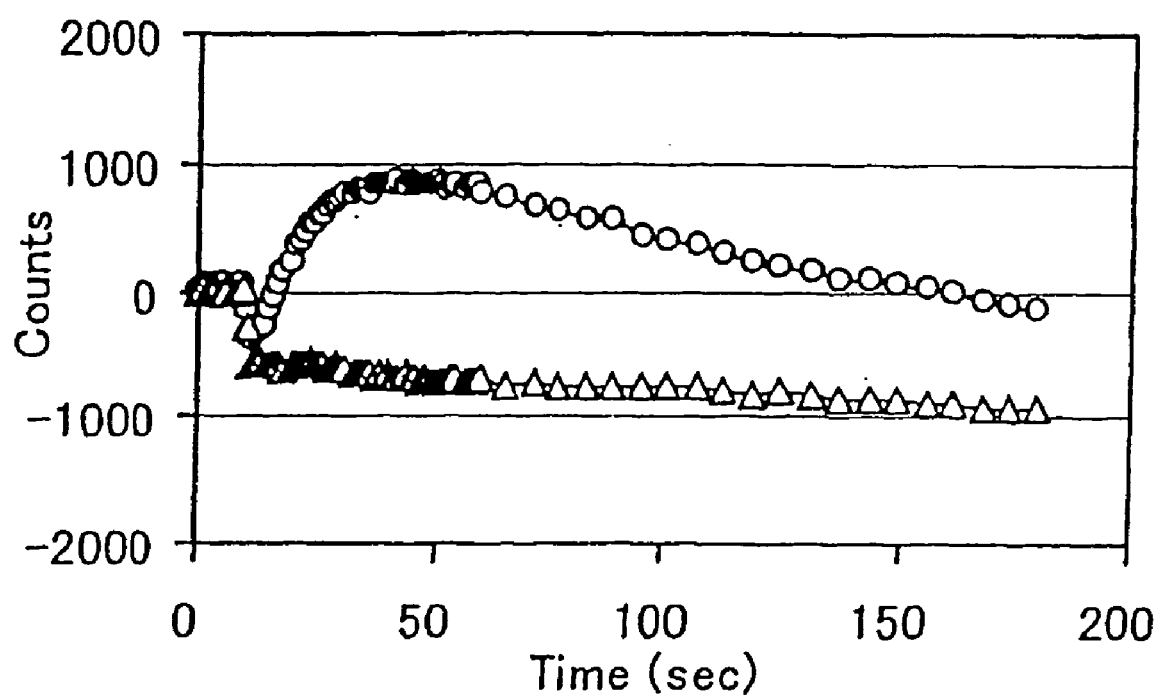
FIG. 2 shows the results of changes in intracellular $Ca^{2+}$ level examined when 5.8.11-eicosatriynoic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 3:
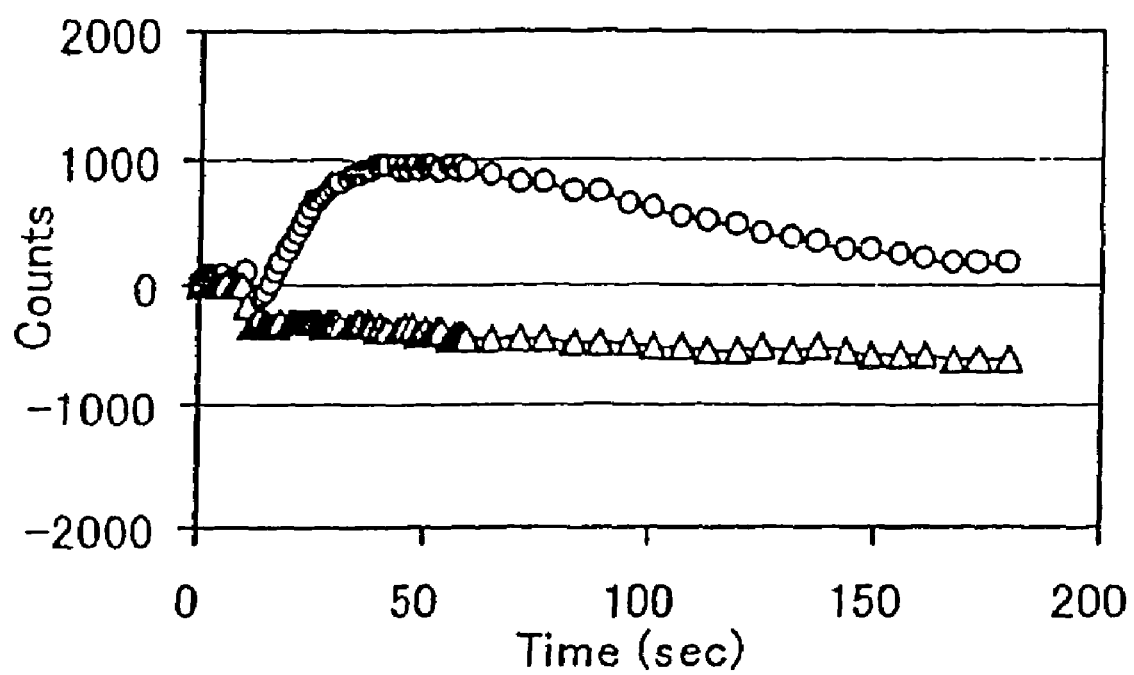
FIG. 3 shows the results of changes in intracellular $Ca^{2+}$ level examined when 5.8.11.14-eicosatetraynoic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 4:
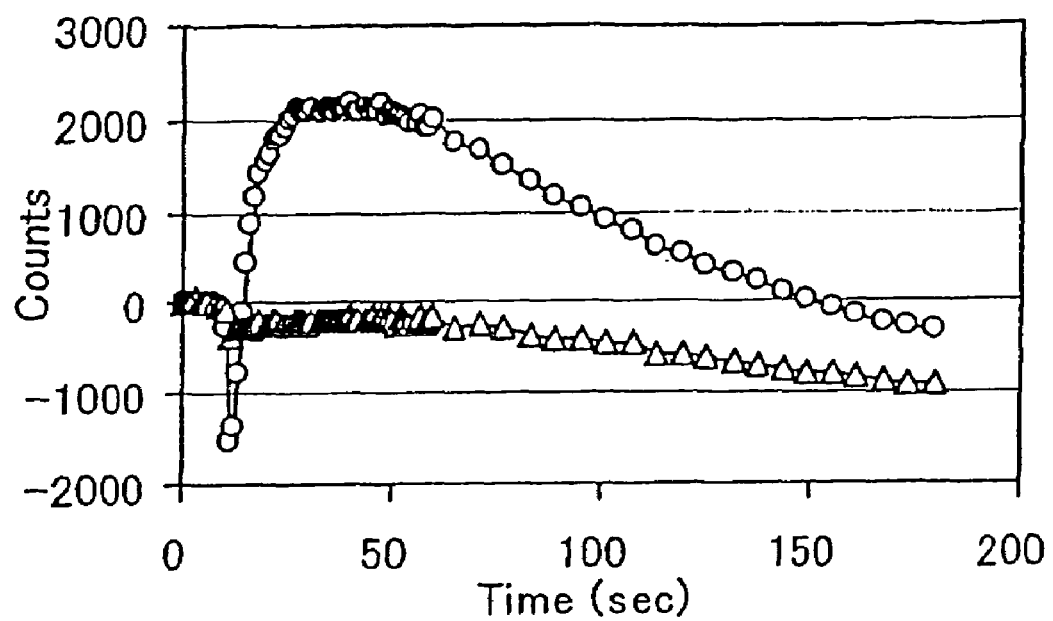
FIG. 4 shows the results of changes in intracellular $Ca^{2+}$ level examined when linoleic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 5:
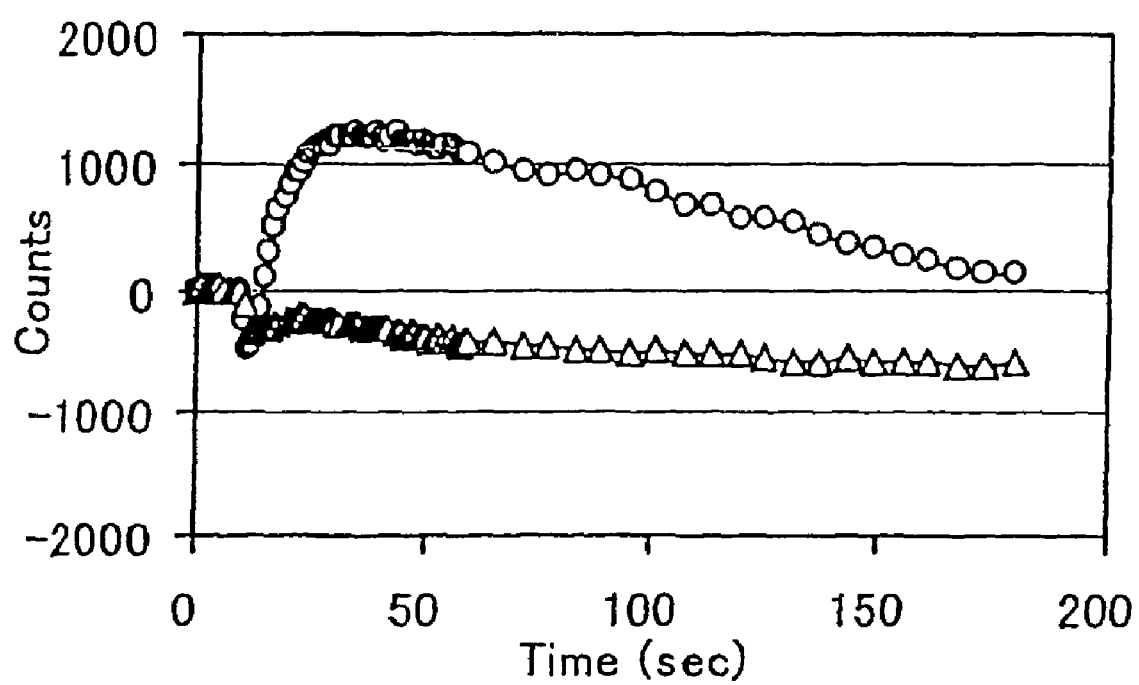
FIG. 5 shows the results of changes in intracellular $Ca^{2+}$ level examined when linolenic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 6:
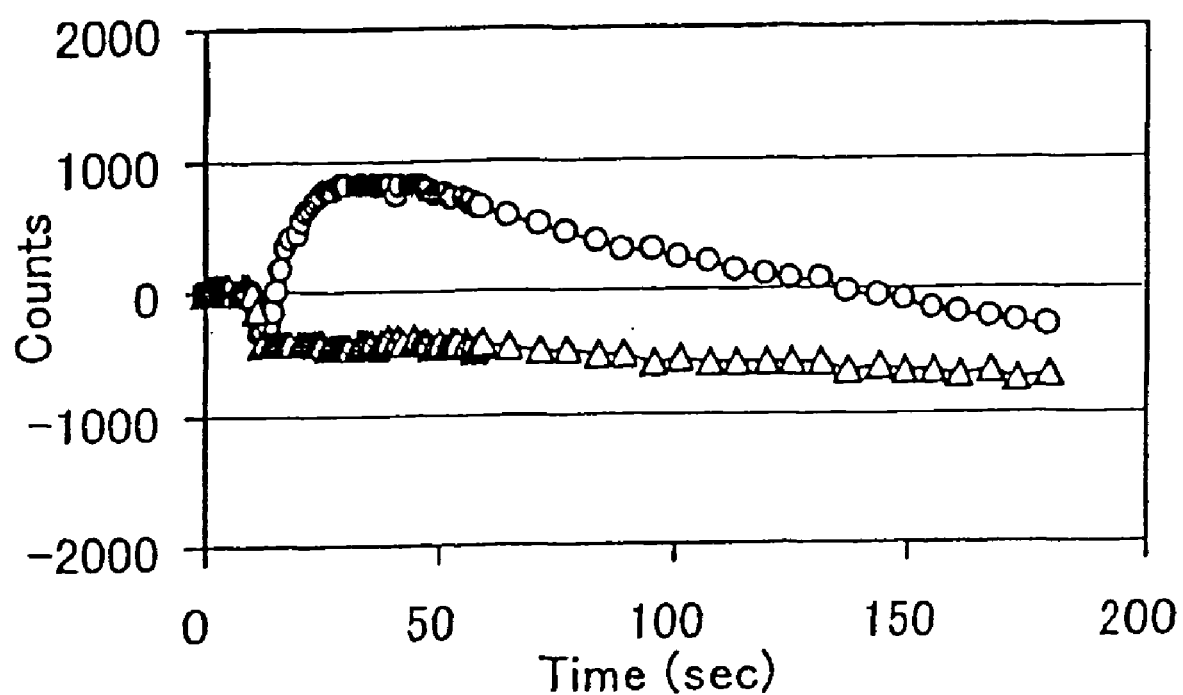
FIG. 6 shows the results of changes in intracellular $Ca^{2+}$ level examined when arachidonic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 7:
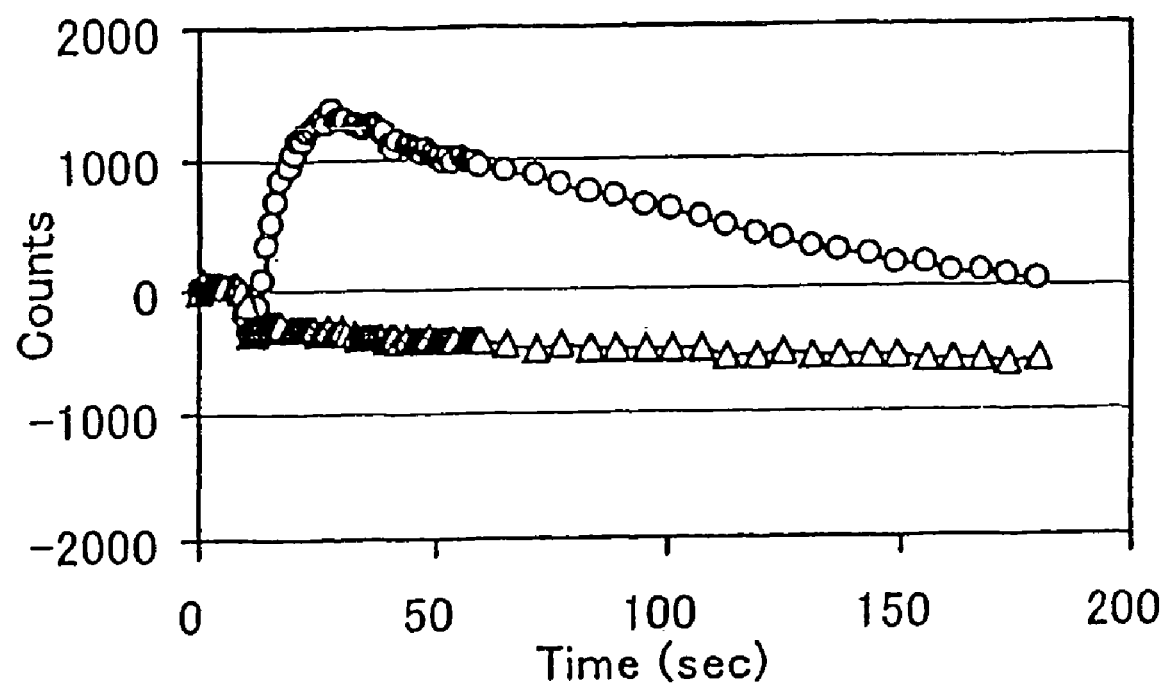
FIG. 7 shows the results of changes in intracellular $Ca^{2+}$ level examined when eicosapentaenoic acid (EPA) was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 8:
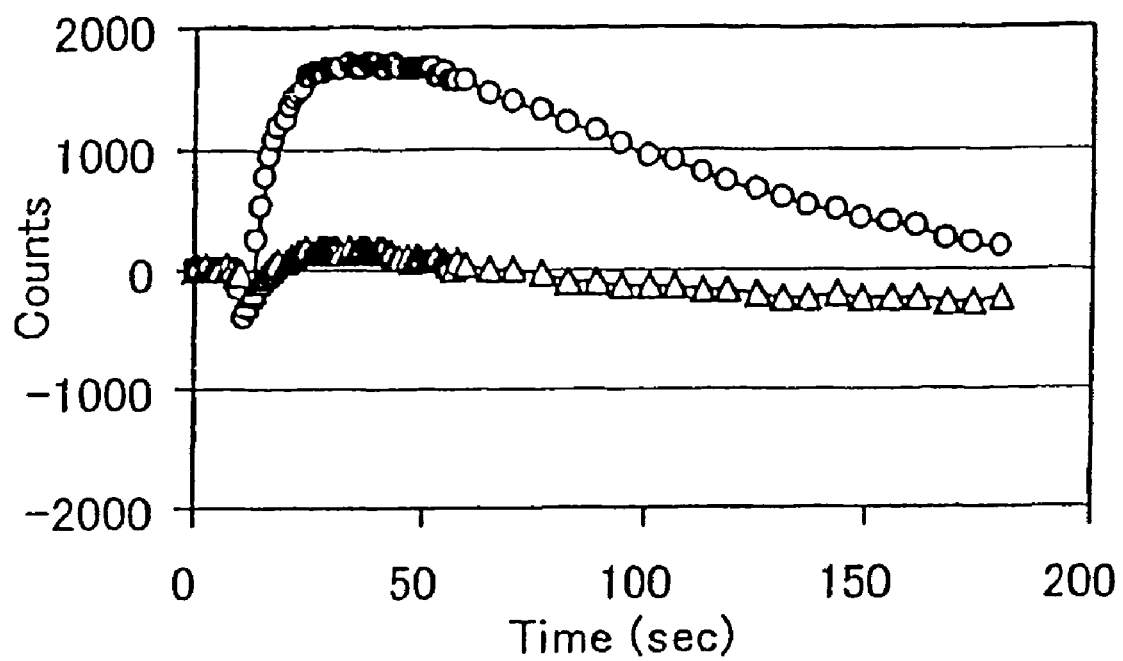
FIG. 8 shows the results of changes in intracellular $Ca^{2+}$ level examined when eicosadienoic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 9:
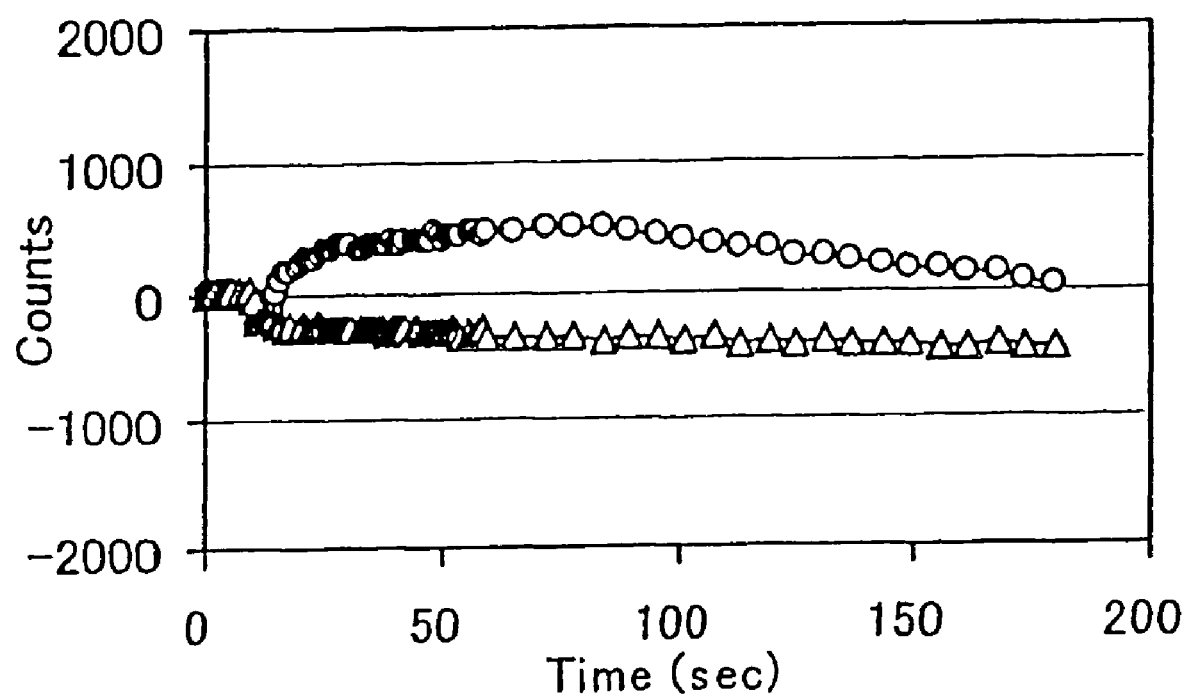
FIG. 9 shows the results of changes in intracellular $Ca^{2+}$ level examined when eicosatrienoic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 10:
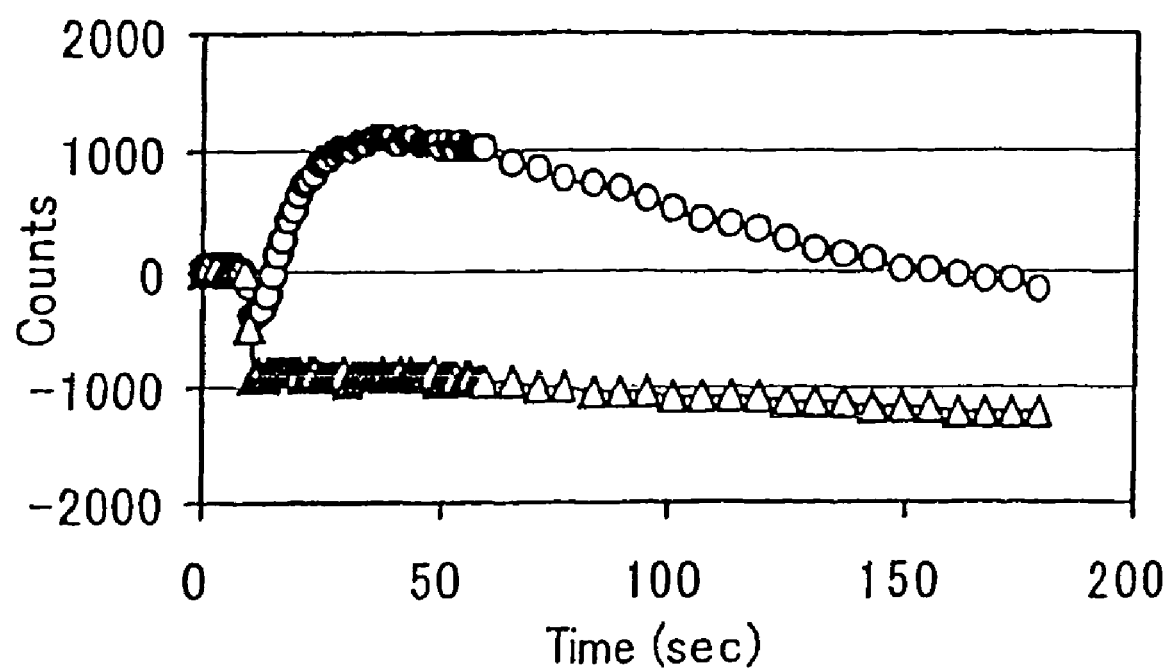
FIG. 10 shows the results of changes in intracellular $Ca^{2+}$ level examined when docosahexaenoic acid (DHA) was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 11:
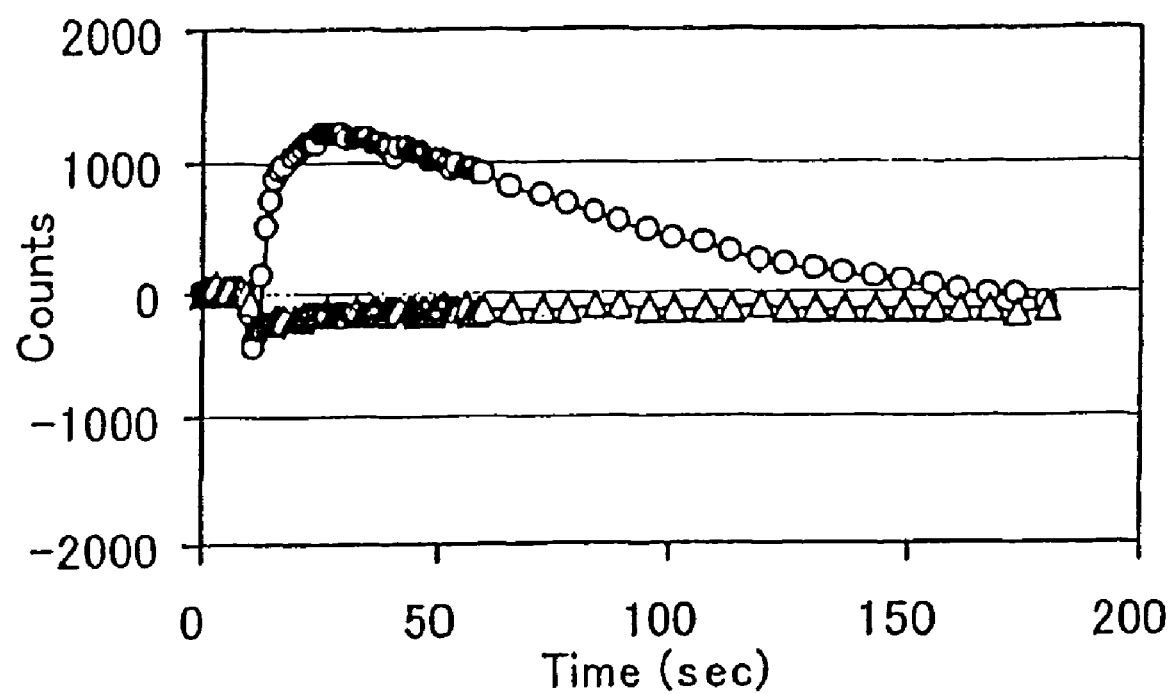
FIG. 11 shows the results of changes in intracellular $Ca^{2+}$ level examined when docosatrienoic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 12:
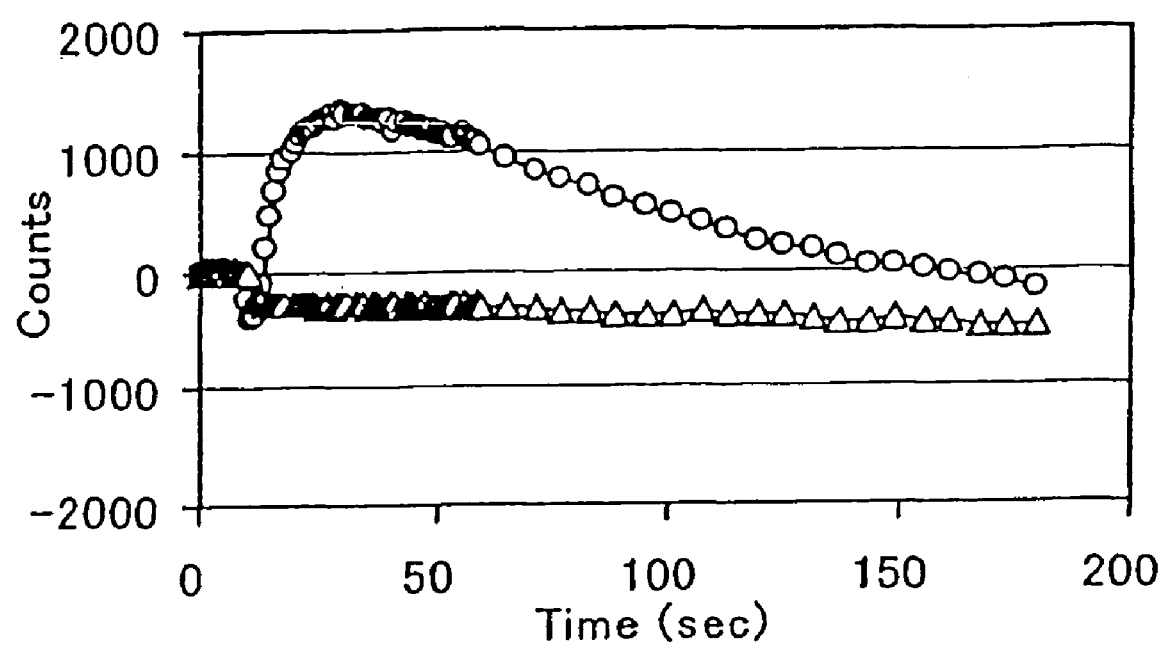
FIG. 12 shows the results of changes in intracellular $Ca^{2+}$ level examined when adrenic acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.
Figure 13:
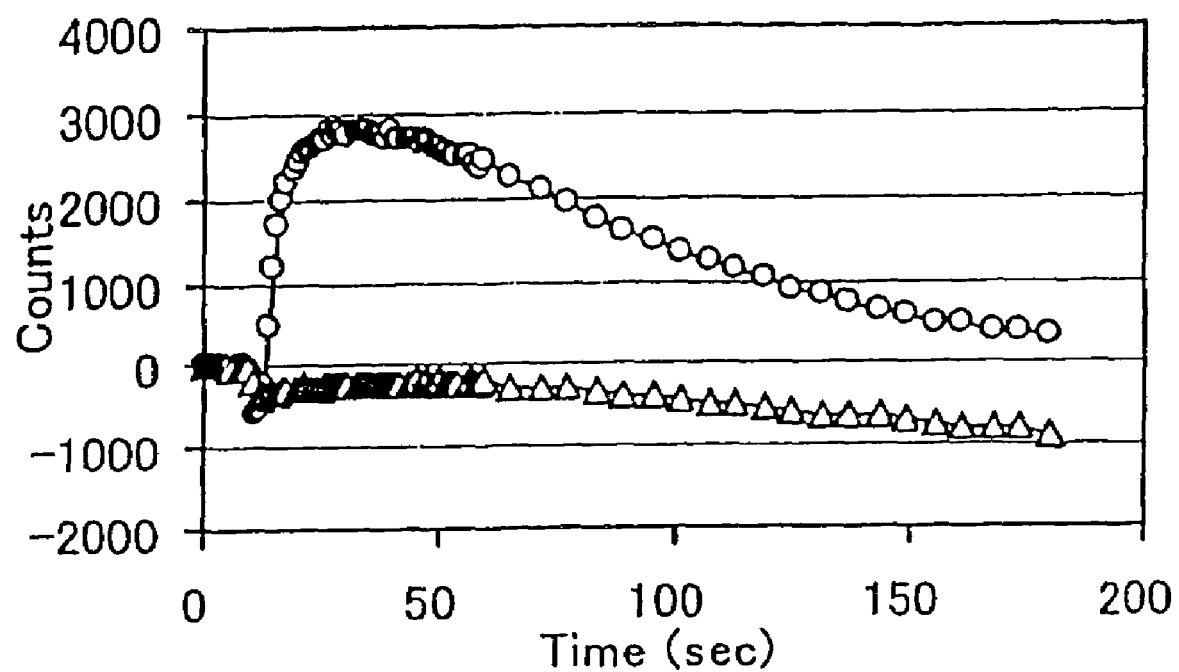
FIG. 13 shows the results of changes in intracellular $Ca^{2+}$ level examined when lauric acid was added. The ordinate designates fluorescence intensity showing the intracellular $Ca^{2+}$ level and the abscissa designates the passage of time after a sample was added, wherein symbols open circle and open triangle denote GPR40-expressed CHO-K1 cells and CHO-K1 cells for control, respectively.

The G protein-coupled receptor protein of the present invention (hereinafter sometimes referred to briefly as GPR40) is a receptor protein containing the same or substantially the same amino acid sequence as the amino acid sequence represented by SEQ ID NO: 1, SEQ ID NO: 3, SEQ ID NO: 5, SEQ ID NO: 17 or SEQ ID NO: 29.

GPR40 may be any protein derived from any cell of human and mammals (e.g., guinea pig, rat, mouse, rabbit, swine, sheep, bovine, monkey, etc.); any cell (e.g., splenocyte, nerve cells, glial cells, β cells of pancreas, pancreatic Langerhans' islet, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testicle, testis, ovary, placenta, uterus, bone, joint, skeletal muscle, etc.; the proteins may also be synthetic proteins. In particular, GPR40 is highly expressed especially in pancreatic Langerhans islets.

The amino acid sequence which has substantially the same amino acid sequence as that represented by SEQ ID NO: 1, SEQ ID NO: 3, SEQ ID NO: 5, SEQ ID NO: 17 or SEQ ID NO: 29 includes an amino acid sequence having at least about 85% homology, preferably at least about 90% homology and more preferably at least about 95% homology, to the amino acid sequence represented by SEQ ID NO: 1, SEQ ID NO: 3, SEQ ID NO: 5, SEQ ID NO: 17 or SEQ ID NO: 29.

Examples of the protein which contains substantially the same amino acid sequence as that shown by SEQ ID NO: 1, SEQ ID NO: 3, SEQ ID NO: 5, SEQ ID NO: 17 or SEQ ID NO: 29 include a protein having substantially the same amino acid sequence as that shown by SEQ ID NO: 1, SEQ ID NO: 3, SEQ ID NO: 5, SEQ ID NO: 17 or SEQ ID NO: 29 and preferably having the activity substantially equivalent to the amino acid sequence represented by SEQ ID NO: 1, SEQ ID NO: 3, SEQ ID NO: 5, SEQ ID NO: 17 or SEQ ID NO: 29, etc.

Examples of the substantially equivalent activity described above include a ligand binding activity, a signal transduction activity, etc. The term substantially equivalent is used to mean that the activities are the same in nature. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of these activities, a molecular weight of the protein, etc. may differ.

The activities such as ligand binding and signal transduction activities or the like can be determined according to publicly known methods with some modifications thereof, for example, by the ligand determination methods or the screening methods that will be later described.

Also, proteins containing the following amino acid sequences are used as GPR40: a) amino acid sequences wherein at least 1 or 2 amino acids (preferably approximately 1 to 30 amino acids, more preferably approximately 1 to 10 amino acids, most preferably several (1 to 5)amino acids) are deleted of the amino acid sequence represented by SEQ ID NO: 1, SEQ ID NO: 3, SEQ ID NO: 5, SEQ ID NO: 17 or SEQ ID NO: 29; b)amino acid sequences wherein at least 1 or 2 amino acids (preferably approximately 1 to 30 amino acids, more preferably approximately 1 to 10 amino acids, and most preferably several (1 to 5) amino acids) are added to the amino acid sequence represented by SEQ ID NO: 1, SEQ ID NO: 3, SEQ ID NO: 5, SEQ ID NO: 17 or SEQ ID NO: 29; c)amino acid sequences wherein at least 1 or 2 amino acids (preferably approximately 1 to 30 amino acids, more preferably approximately 1 to 10 amino acids, and most preferably several (1 to 5) amino acids) in the amino acid sequence represented by SEQ ID NO: 1, SEQ ID NO: 3, SEQ ID NO: 5, SEQ ID NO: 17 or SEQ ID NO: 29 are substituted by other amino acids; or d) combination of these amino acid sequences described above; and the like.

Throughout the present specification, GPR40 is represented in accordance with the conventional way of describing peptides, that is, the N-terminus (amino terminus) at the left hand and the C-terminus (carboxyl terminus) at the right hand. In the GPR40 including GPR40 containing the amino acid sequence shown by SEQ ID NO: 1, the C-terminus may be in any form of a carboxyl group (—COOH), carboxylate (—COO$^-$), an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where GPR40 contains a carboxyl group (or a carboxylate) at a position other than the C-terminus, it may be amidated or esterified and such an amide or ester is also included within the GPR40 of the present invention. The ester group may be the same group as that described with respect to the C-terminus described above.

Furthermore, examples of GPR40 include variants of the above proteins, wherein the amino group at the N-terminal methionine residue of the protein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of the GPR40 of the present invention include mouse-derived GPR40 containing the amino acid sequence represented by SEQ ID NO: 1, rat-derived GPR40 containing the amino acid sequence represented by SEQ ID NO: 3, a human-derived GPR40 containing the amino acid sequence represented by SEQ ID NO: 5, cynomolgus monkey-derived GPR40 containing the amino acid sequence represented by SEQ ID NO: 17, hamster-derived GPR40 containing the amino acid sequence represented by SEQ ID NO: 29, etc. Among them, mouse-derived GPR40, rat-derived GPR40, cynomolgus monkey-derived GPR40 and hamster-derived GPR40 are novel proteins. Human-derived GPR40 is a publicly known protein described in WO2000-22129, Biochem. Biophys. Res. Commun. 1997, Oct. 20; 239(2):543–547.

As partial peptides of GPR40 (hereinafter sometimes referred to as the partial peptides), any partial peptide can be used so long as it can be a partial peptide of the aforesaid GPR40. Among the GPR40 protein molecules, for example, those having a site exposed to the outside of a cell membrane and having substantially the same receptor binding activity can be used.

Specifically, the partial peptide of GPR40 having the amino acid sequence represented by SEQ ID NO: 1, SEQ ID NO: 3, SEQ ID NO: 5, SEQ ID NO: 17 or SEQ ID NO: 29 is a peptide containing the parts analyzed to be extracellular domains (hydrophilic domains) in the hydrophobic plotting analysis. A peptide containing a hydrophobic domain in part can be used as well. In addition, the peptide may contain each domain separately or plural domains together.

In the partial peptides of the present invention, preferred are peptides having at least 20, preferably at least 50, and more preferably at least 100 amino acids, in the amino acid sequence which constitutes the receptor protein of the present invention described above.

The amino acid sequence having substantially the same amino acid sequence includes an amino acid sequence having at least about 85% homology, preferably at least about 90% homology and more preferably at least about 95% homology, to these amino acid sequences.

Herein the term "substantially the same receptor binding activity" has the same significance as described above. The "substantially the same receptor binding activity" can be assayed by the same manner as described above.

In the amino acid sequence described above, the partial peptide of the present invention may contain amino acid sequences, of which at least 1 or 2 amino acids (preferably approximately 1 to 10 amino acids, more preferably several (1 to 5) amino acids) are deleted; to which at least 1 or 2 amino acids (preferably approximately 1 to 20 amino acids, more preferably approximately 1 to 10 amino acids, and most preferably several (1 to 5) amino acids) are added; or, in which at least 1 or 2 amino acids (preferably approximately 1 to 10 amino acids, more preferably several and most preferably approximately 1 to 5 amino acids) are substituted by other amino acids.

In the partial peptide of the present invention, the C-terminus may be in any form of a carboxyl group (—COOH), carboxylate (—COO$^-$), an amide (—CONH$_2$) or an ester (—COOR). Where the partial peptide of the present invention, as has been described with the protein of the present invention. Where GPR40 contains a carboxyl group (or a carboxylate) at a position other than the C-terminus, it may be amidated or esterified and such an amide or ester is also included within the GPR40 of the present invention. In this case, the ester group may be the same group as that described with respect to the C-terminus described above.

As in the GPR40 described above, the partial peptide of the present invention further includes those in which the amino group of the amino acid residue of the N-terminal methionine residue is protected by a protecting group, those in which the N-terminal residue is cleaved in vivo and the produced glutamine residue is pyroglutaminated, those in which substituents on the side chains of amino acids in the molecule are protected by appropriate protecting groups, conjugated peptides such as so-called glycopeptides, to which sugar chains are bound, and the like.

For salts of the GPR40 of the present invention or its partial peptide, preferred are physiologically acceptable salts with acids or bases, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The GPR40 of the present invention or salts thereof may be manufactured by a publicly known method used to purify receptor proteins from human or mammalian cells or tissues described above, or by culturing a transformant that contains the DNA encoding the GPR40 of the present invention, as will be later described. Furthermore, the GPR40 or its salts may also be manufactured by the methods for synthesizing proteins or by modifications thereof, which will also be described hereinafter.

Where the GPR40 or its salts are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the GPR40 of the present invention or its partial peptides, or salts or amides thereof according to the present invention, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the protein is cut out from the resin and at the same time, the protecting groups are removed. Then, intramolecular disulfide bond-forming reaction is performed in a highly diluted solution to obtain the objective protein or its amides.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminoprolyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups used in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids, in which the amino groups are activated in the starting material, for example, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups, activation of functional groups involved in the reaction, or the like may be appropriately selected from publicly known groups and publicly known means.

In another method for obtaining the amides of the protein, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group in the peptide chain has been eliminated from the protein and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. L yophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the ester form of the desired protein.

The partial peptide or its salts in the GPR40 of the present invention can be manufactured by publicly known methods for peptide synthesis, or by cleaving the GPR40 of the present invention with an appropriate peptidase. For the methods for peptide synthesis, for example, either solid phase synthesis or liquid phase synthesis may be used. That is, the partial peptide or amino acids that can construct the GPR40 of the present invention are condensed with the remaining part. Where the product contains protecting groups, these protecting groups are removed to give the desired peptide. Publicly known methods for condensation and elimination of the protecting groups are described in a)–e) below.

a) M. Bodanszky & M. A. Ondetti: Peptide Synthesis, Interscience Publishers, New York (1966)

b) Schroeder & Luebke: The Peptide, Academic Press, New York (1965)

c) Nobuo Izumiya, et al.: *Peptide Gosei-no-Kiso to Jikken* (Basics and experiments of peptide synthesis), published by Maruzen Co. (1975)

d) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

e) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the methods above is in a free form, the peptide can be converted into an appropriate salt by a publicly known method; conversely when the peptide is obtained in a salt form, it can be converted into a free form by a publicly known method.

The polynucleotide encoding the GPR40 of the present invention may be any polynucleotide so long as it contains the base sequence (DNA or RNA, preferably DNA) encoding the GPR40 of the present invention described above. Such a polynucleotide may also be any one of DNA encoding the GPR40 of the present invention, RNA such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the GPR40 of the present invention, mRNA of the GPR40 of the present invention can be quantified by, for example, the publicly known method published in separate volume of *Jikken Igaku* 15 (7) "New PCR and its application" (1997), or by its modifications.

The DNA encoding the GPR40 of the present invention may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding the GPR40 of the present invention may be any DNA, so long as it is, for example, a DNA containing the base sequence represented by SEQ ID NO: 2, SEQ ID NO: 4, SEQ ID NO: 6, SEQ ID NO: 18 or SEQ ID NO: 30, or any DNA having a base sequence hybridizable to the base sequence represented by SEQ ID NO: 2, SEQ ID NO: 4, SEQ ID NO: 6, SEQ ID NO: 18 or SEQ ID NO: 30 under high stringent conditions and encoding a receptor protein which has the activities substantially equivalent to those of GPR40 consisting of the amino acid sequence as the amino acid sequence represented by SEQ ID NO: 1, SEQ ID NO: 3, SEQ ID NO: 5, SEQ ID NO: 17 or SEQ ID NO: 29 (e.g., the ligand-binding activities, the signal transduction activities, etc.).

Examples of the DNA hybridizable to the DNA containing the base sequence represented by SEQ ID NO: 2, SEQ ID NO: 4, SEQ ID NO: 6, SEQ ID NO: 18 or SEQ ID NO: 30 under highly stringent conditions include a DNA containing a base sequence having at least about 85% homology, preferably at least about 90% homology and more preferably at least about 95% homology, to the base sequence represented by SEQ ID NO: 2, SEQ ID NO: 4, SEQ ID NO: 6, SEQ ID NO: 18 or SEQ ID NO: 30.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, for the DNA encoding mouse GPR40 containing the amino acid sequence represented by SEQ ID NO: 1, there may be employed a DNA containing the base sequence represented by SEQ ID NO: 2; etc.

For the DNA encoding mouse GPR40 containing the amino acid sequence represented by SEQ ID NO: 3, there may be employed a DNA containing the base sequence represented by SEQ iD NO: 4; etc.

For the DNA encoding mouse GPR40 containing the amino acid sequence represented by SEQ ID NO: 5, there may be employed a DNA containing the base sequence represented by SEQ ID NO: 6; etc.

For the DNA encoding cynomolgus monkey GPR40 containing the amino acid sequence represented by SEQ ID NO: 17, there may be employed a DNA containing the base sequence represented by SEQ ID NO: 18; etc.

For the DNA encoding hamster GPR40 containing the amino acid sequence represented by SEQ ID NO: 29, there may be employed a DNA containing the base sequence represented by SEQ ID NO: 30; etc.

The term polynucleotide comprising a part of the base sequence of the DNA encoding the GPR40 of the present invention or a part of the base sequence complementary to the DNA is used to mean that the polynucleotide embraces not only the DNA encoding the partial peptide of the present invention described below but also RNA.

According to the present invention, antisense polynucleotides (nucleic acids) that can inhibit the replication or expression of GPR genes can be designed and synthesized based on the base sequence information of the cloned or determined DNA encoding GPR40. Such a polynucleotide (nucleic acid) is capable of hybridizing to RNA of GPR40 gene to inhibit the synthesis or function of said RNA or capable of modulating or controlling the expression of the GPR40 gene via interaction with GPR40-associated RNA. Polynucleotides complementary to the selected sequences of GPR-associated RNA and polynucleotides specifically hybridizable to the GPR-associated RNA are useful in modulating or controlling the expression of the GPR40 gene in vivo and in vitro, and useful for the treatment or diagnosis of diseases. The term "corresponding" is used to mean homologous to or complementary to a particular sequence of the nucleotide, base sequence or nucleic acid including the gene. The term "corresponding" between nucleotides, base sequences or nucleic acids and peptides (proteins) usually refer to amino acids of a peptide (protein) under the order derived from the sequence of nucleotides (nucleic acids) or their complements. In the GPR40 genes, the 5' end hairpin loop, 5' end 6-base-pair repeats, 5' end untranslated region, polypeptide translation initiation codon, protein coding region, ORF translation initiation codon, 3' end untranslated region, 3' end palindrome region, and 3' end hairpin loop, may be selected as preferred target regions, though any other region may be selected as a target in the GPR40 genes.

The relationship between the targeted nucleic acids and the polynucleotides complementary to at least a part of the target, specifically the relationship between the target and the polynucleotides hybridizable to the target, can be denoted to be "antisense". Examples of the antisense polynucleotides include polydeoxyribonucleotide containing 2-deoxy-D-ribose, polyribonucleotide containing D-ribose, any other type of polynucleotides which are N-glycosides of a purine or pyrimidine base, or other polymers containing non-nucleotide backbones (e.g., protein nucleic acids and synthetic sequence-specific nucleic acid polymers commercially available) or other polymers containing nonstandard linkages (provided that the polymers contain nucleotides having such a configuration that allows base pairing or base stacking, as is found in DNA or RNA), etc. They may be double-stranded DNA, single-stranded DNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., α anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain changed or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system of the G protein-coupled receptor protein in vivo and in vitro. The nucleic acid can be applied to cells by a variety of publicly known methods.

The siRNA to the polynucleotide of the present invention is a double-stranded RNA containing a part of the RNA encoding GPR40 and its complementary RNA. Specifically, there are employed a siRNA constructed by a sense strand consisting of the base sequence represented by SEQ ID NO: 34 and an antisense strand consisting of the base sequence represented by SEQ ID NO: 35, a siRNA constructed by a sense strand consisting of the base sequence represented by SEQ ID NO: 36, an antisense strand consisting of the base sequence represented by SEQ ID NO: 37 (FIG. 22), etc.

The siRNA can be designed based on the sequence of the polynucleotide of the present invention and manufactured by modifications of publicly known methods (e.g., Nature, 411, 494, 2001).

The ribozyme containing a part of the RNA encoding GPR40 can be designed based on the sequence of the polynucleotide of the present invention and manufactured by modifications of publicly known methods (e.g., TRENDS in Molecular Medicine, 7, 221, 2001). For example, it can be manufactured by replacing a part of ribozyme publicly known with a part of the RNA encoding GPR40. The part of RNA encoding GPR40 includes a portion in the vicinity of the consensus sequence NUX (wherein N represents all bases and X represents a base other than G), which may be cleaved with by ribozyme publicly known.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using mRNA fraction prepared from the cells and tissues described above.

Specifically, the DNA encoding the partial peptide of the present invention may be any one of, for example, (1) a DNA containing a partial base sequence of the DNA having the base sequence represented by SEQ ID NO: 2, SEQ ID NO: 4, SEQ ID NO: 6, SEQ ID NO: 18 or (2) any DNA containing a partial base sequence of the DNA having a DNA hybridizable to the DNA represented by SEQ ID NO: 2, SEQ ID NO: 4, SEQ ID NO: 6, SEQ ID NO: 18 or SEQ ID NO: 30 under highly stringent conditions and encoding the receptor protein which has the activities (e.g., the ligand-biding activities, the signal transduction activities, etc.) substantially equivalent to those of GPR40 consisting of the amino acid sequence represented by SEQ ID NO: 1, SEQ ID NO: 3, SEQ ID NO: 5, SEQ ID NO: 17 or SEQ ID NO: 29; etc.

Examples of the DNA that is hybridizable to the base sequence represented by SEQ ID NO: 2, SEQ ID NO: 4, SEQ ID NO: 6, SEQ ID NO: 18 or SEQ ID NO: 30 include DNA containing a base sequence having at least about 85% homology, preferably at least about 90% homology and more preferably at least about 95% homology, to the base sequence represented by SEQ ID NO: 2, SEQ ID NO: 4, SEQ ID NO: 6, SEQ ID NO: 18 or SEQ ID NO: 30.

For cloning of the DNA that completely encodes the GPR40 of the present invention or its partial peptide (hereinafter sometimes collectively referred to as the GPR40 of the present invention), the DNA may be amplified by PCR using synthetic DNA primers containing a part of the base sequence of DNA encoding the GPR40 of the present invention, or the DNA inserted into an appropriate vector can be selected by hybridization with a labeled DNA fragment or synthetic DNA that encodes a part or entire region of the GPR40 of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the base sequence of the DNA can be effected by publicly known methods such as the ODA-LA PCR method, the Gapped duplex method or the Kunkel method or its modification by using a publicly known kit available as Mutan™-superExpressKm (manufactured by TaKaRa Shuzo Co., Ltd.), Mutan™-K (manufactured by TaKaRa Shuzo Co., Ltd.), etc.

The cloned DNA encoding GPR40 can be used as it is, depending upon purpose or, if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons may also be added by using an appropriate synthetic DNA adapter.

The expression vector for the GPR40 of the present invention can be manufactured, for example, by (a) excising the desired DNA fragment from the DNA encoding the GPR40 of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV promoter or SRα promoter is preferably used. Where the host is bacteria of the genus *Escherichia*, preferred examples of the promoter include trp promoter, lac promoter, recA promoter, λ$P_L$ promoter, lpp promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker in CHO (dhfr$^-$) cells, selection can also be made on thymidine free media.

If necessary, a signal sequence that matches with a host is added to the N-terminus of the receptor protein of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the GPR40 of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)), JM103 (Nucleic Acids Research, 9, 309 (1981)], JA221 [Journal of Molecular Biology, 120, 517 (1978)], HB101 [Journal of Molecular Biology, 41, 459 (1969)), C600 (Genetics, 39, 440 (1954)], etc.

Examples of the bacteria belonging to the genus *Bacillus* include *Bacillus subtilis* MI114 [Gene, 24, 255 (1983)], 207–21 [Journal of Biochemistry, 95, 87 (1984)], etc.

Examples of yeast include *Saccharomyces cereviseae* AH22, AH22R$^-$, NA87-11A, DKD-5D, 20B-12, *Schizosaccharomyces pombe* NCYC1913, NCYC2036, *Pichia pastoris*, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vivo, 13, 213–217 (1977)).

As the insect, for example, a larva of *Bombyx mori* can be used [Maeda, et al., Nature, 315, 592 (1985)].

Examples of animal cells include monkey cells COS-7, Vero, Chinese hamster cells CHO (hereinafter referred to as CHO cells), dhfr gene deficient Chinese hamster cells CHO (hereinafter simply referred to as CHO (dhfr$^-$) cell), mouse L cells, mouse AtT-20, mouse myeloma cells, rat GH3, human FL cells, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979).

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263–267 (1995), published by Shujunsha, or Virology, 52, 456 (1973).

Thus, the transformant transformed with the expression vector containing the DNA encoding GPR40 can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431–433, Cold Spring Harbor Laboratory, New York, 1972). If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 hours to about 24 hours. If necessary, the culture may be aerated or agitated.

Where the bacteria belonging to the genus *Bacillus* are used as the host, the transformant is cultivated generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the GPR40 of the present invention can be produced into the cell, in the cell membrane or out of the cell of the transformant.

The GPR40 of the present invention can be separated and purified from the culture described above by the following procedures.

When the GPR40 of the present invention is extracted from the culture or cells, after cultivation the transformants or cells are collected by a publicly known method and suspended in a appropriate buffer. The transformants or cells are then disrupted by publicly known methods such as ultrasonication, a treatment with lysozyme and/or freeze-thaw cycling, followed by centrifugation, filtration, etc. Thus, the crude extract of GPR40 can be obtained. The buffer used for the procedures may contain a protein modifier such as urea or guanidine hydrochloride, or a surfactant such as Triton X-100™, etc. When GPR40 is secreted in the culture, after completion of the cultivation the supernatant can be separated from the transformants or cells to collect the supernatant by a publicly known method.

The GPR40 contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

In the case that the GPR40 thus obtained is in a free form, it can be converted into the salt by publicly known methods or modifications thereof. On the other hand, when the GPR40 is obtained in the form of a salt, it can be converted into the free form or in the form of a different salt by publicly known methods or modifications thereof.

The GPR40 produced by the recombinant can be treated, prior to or after the purification, with an appropriate protein modifying enzyme so that the GPR40 can be appropriately modified to partially remove a polypeptide. Examples of the protein-modifying enzyme include trypsin, chymotrypsin, arginyl endopeptidase, protein kinase, glycosidase or the like.

The activity of the thus produced GPR40 of the present invention or salts thereof can be determined by a binding experiment to a labeled ligand, by an enzyme immunoassay using a specific antibody, or the like.

Antibodies to the GPR40 of the present invention may be any of polyclonal antibodies and monoclonal antibodies, as long as they are capable of recognizing the GPR40 of the present invention.

The antibodies to the GPR40 of the present invention may be manufactured by publicly known methods for manufacturing antibodies or antisera, using as antigens the GPR40 of the present invention.

[Preparation of Monoclonal Antibody]

(a) Preparation of Monoclonal Antibody-Producing Cells

The GPR40 of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable mammals are monkeys, rabbits, dogs, guinea pigs, mice, rats, sheep and goats, with mice and rats being preferred.

In the preparation of monoclonal antibody-producing cells, warm-blooded animals, e.g., mice, immunized with an antigen wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled form of the receptor protein, which will be described later, with the antiserum followed by assaying the binding activity of the labeling agent bound to the antibody. The fusion may be operated, for example, by the known Koehler and Milstein method [Nature, 256, 495 (1975)]. Examples of the fusion accelerator are polyethylene glycol (PEG), Sendai virus, etc., of which PEG is preferably employed.

Examples of the myeloma cells are NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to about 40° C., preferably at about 30 to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with an antigen of the receptor protein directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the receptor protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G etc. and dissociating the binding to obtain the antibody].

[Preparation of Polyclonal Antibody]

The polyclonal antibody of the present invention can be manufactured by publicly known methods or modifications thereof. For example, a complex of immunogen (GPR40 antigen) and a carrier protein is prepared, and a mammal is immunized with the complex in a manner similar to the method described above for the manufacture of monoclonal antibodies. The product containing the antibody to the GPR40 of the present invention is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warm-blooded animals either solely or together with carriers or diluents to the site in which the antibody can be produced by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

Specifically, preferred examples of the antibodies to the GPR40 of the present invention are antibodies capable of recognizing the C-terminal peptide of the GPR40 of the present invention (especially monoclonal antibodies), etc. More specifically, a monoclonal antibody capable of recognizing the peptide represented by SEQ ID NO: 33, which is the C-terminal peptide of human GPR40, or its salt, and the like are used.

One of the ligands to the GPR40 of the present invention is the fatty acid or its salt. For example, unsaturated fatty acids or saturated fatty acids present in foods or in the living organism, or their salts are used. Above all, unsaturated fatty acids or saturated fatty acids having approximately 10 to 30 carbon atoms or their salts are preferably used. Specifically, there are used farnesoic acid, 5.8.11-eicosatriynoic acid, 5.8.11.14-eicosatetraynoic acid, oleic acid, linoleic acid, linolenic acid, α-linolenic acid, γ-linolenic acid, arachidonic acid, eicosapentaenoic acid, EPA, eicosadienoic acid, eicosatrienoic acid, docosahexaenoic acid, DHA, docosatrienoic acid, adrenic acid, lauric acid, palmitic acid, or salts thereof, etc.

As salts of the fatty acids, there are used salts with acids (e.g., inorganic acids, organic acids, etc.), bases (e.g., alkali metals such as sodium, potassium, etc.; alkaline earth metals such as calcium, etc.) or the like, with particular preference being bases.

Hereinafter, the fatty acids or salts thereof are merely referred to as "fatty acids" throughout the specification.

Moreover, one of the ligands to the GPR40 of the present invention is the eicosanoid, and there are used, for example, (±)14,15-dihydroxy-5Z,8Z,11Z-eicosatrienoic acid (14,15-DHT), (±)5(6)-epoxy-8Z,11Z,14Z-eicosatrienoic acid (5,6-EET), (±)8(9)-epoxy-5Z,11Z,14Z-eicosatrienoic acid (8,9-

EET), (±)11(12)-epoxy-5Z,8Z,14Z-eicosatrienoic acid (11,12-EET), (±)14(15)-epoxy-5Z,8Z,11Z-eicosatrienoic acid (14,15-EET), etc.

Also, the GPR40 of the present invention is highly expressed especially in pancreatic Langerhans islets.

Thus, the GPR40 of the present invention, the DNA encoding GPR40 (hereinafter sometimes referred to briefly as the DNA of the present invention), the antibody to GPR40 (hereinafter sometimes referred to briefly as the antibody of the present invention), the antisense DNA to the DNA of the present invention (hereinafter sometimes merely referred to as the antisense DNA of the present invention) and the siRNA to the polynucleotide of the invention (hereinafter sometimes merely referred to as the siRNA of the present invention) have the following applications.

(1) Preventive and/or Therapeutic Agent for Diseases Associated with Dysfunction of the GPR40 of the Present Invention a) The GPR40 of the present invention or b) the DNA encoding the GPR40 of the present invention can be used as a preventive and/or therapeutic agent, etc. for diseases associated with dysfunction of the GPR40 of the present invention.

For example, when the physiological activities of the fatty acid or the eicosanoid, which is the ligand, cannot be expected in a patient (deficiency of GPR40) due to a decrease of the GPR40 of the present invention, the amount of GPR40 can be increased in the boy of the patient a) by administering the GPR40 of the present invention to the patient thereby to supplement the amount of the GPR40; or b) (i) by administering the DNA encoding the GPR40 of the present invention to the patient and expressing the same, or (ii) by inserting and expressing the DNA encoding the GPR40 of the present invention in the objective cells and then transplanting the cells to the patient, thus increasing the amount of the GPR40 in the body of the patient, whereby the activities of the ligand can be sufficiently exhibited. That is, the DNA encoding the GPR40 of the present invention is useful as a safe and low toxic preventive and/or therapeutic agent for diseases associated with dysfunction of the GPR40 of the present invention, a pancreatic function regulating agent (e.g., a pancreatic function improving agent), an insulin secretagogue, a hypoglycemic agent, a pancreatic β cell protecting agent, etc.

Specifically, the GPR40 of the present invention or the DNA of the present invention can be used as a preventive/therapeutic agent for, e.g., diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc. Diabetes mellitus includes insulin dependent (type I) diabetes mellitus, insulin non-dependent (type II) diabetes mellitus, etc.

When the GPR40 of the present invention is used as the preventive/therapeutic agent above, the GPR40 can be prepared into a pharmaceutical composition in a conventional manner.

On the other hand, where the DNA of the present invention is used as the preventive/therapeutic agent described above, the DNA itself is administered; alternatively, the DNA is inserted into an appropriate vector such as retrovirus vector, adenovirus vector, adenovirus-associated virus vector, etc. and then administered in a conventional manner. The DNA of the present invention may also be administered as naked DNA, or with adjuvants to assist its uptake by gene gun or through a catheter such as a catheter with a hydrogel.

For example, a) the GPR40 of the present invention or b) the DNA of the present invention can be used orally, for example, in the form of tablets which may be sugar coated if necessary, capsules, elixirs, microcapsules etc., or parenterally in the form of injectable preparations such as a sterile solution and a suspension in water or with other pharmaceutically acceptable liquid. These preparations can be manufactured by mixing a) the GPR40 of the present invention or b) the DNA of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The effective component in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol.

The preventive/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the GPR40 of the present invention varies depending on subject to be administered, organs to be administered, conditions, methods for administration, etc.; in oral administration, e.g., for the patient with diabetes mellitus, the dose is normally about 0.1 mg to about 100 mg, preferably about 1.0 to about 50 mg, and more preferably about 1.0 to about 20 mg per day (as 60 kg). In parenteral administration, the single dose varies depending on subject to be administered, target organ, conditions, methods for administration, etc. but it is advantageous, e.g., for the patient with diabetes mellitus, to administer the active ingredient intravenously in a daily dose of about 0.01 to about 30 mg, preferably about 0.1 to about 20 mg, and more preferably about 0.1 to about 10 mg (as 60 kg). For other animal species, the corresponding dose as converted per 60 kg can be administered.

The dose of the DNA of the present invention varies depending on subject to be administered, organs to be administered, conditions, methods for administration, etc.; in oral administration, e.g., for the patient with diabetes mellitus, the dose is normally about 0.1 mg to about 100 mg, preferably about 1.0 to about 50 mg, and more preferably about 1.0 to about 20 mg per day (as 60 kg). In parenteral administration, the single dose varies depending on subject to be administered, target organ, conditions, methods for administration, etc. but it is advantageous, e.g., for the patient with diabetes mellitus, to administer the active ingredient intravenously in a daily dose of about 0.01 to about 30 mg, preferably about 0.1 to about 20 mg, and more preferably about 0.1 to about 10 mg (as 60 kg). For other animal species, the corresponding dose as converted per 60 kg can be administered.

(2) Gene Diagnostic Agent

By using the DNA, antisense DNA and siRNA of the present invention as probes, an abnormality (gene abnormality) of the DNA or mRNA encoding the GPR40 of the present invention or its partial peptides in human or mammals (e.g., rats, mice, rabbits, sheep, swine, bovine, cats, dogs, monkeys, etc.) can be detected, and are thus useful as gene diagnostic agents for the damage against the DNA or mRNA, its mutation, or its reduced expression, or increased expression or overexpression of the DNA or mRNA.

The gene diagnosis described above using the DNA, antisense DNA or siRNA of the present invention can be performed by, for example, the publicly known Northern hybridization assay or the PCR-SSCP assay (Genomics, 5, 874–879 (1989); Proceedings of the National Academy of Sciences of the United States of America, 86, 2766–2770 (1989)), etc.

Where a reduced expression of the GPR40 of the present invention is detected, e.g., by northern hybridization, it can be diagnosed that one suffers from, for example, diseases associated with dysfunction of the GPR40 of the present invention, or it is highly likely to suffer from these disease in the future.

Also, where the overexpression of the GPR40 of the present invention is detected, e.g., by northern hybridization, it can be diagnosed that one suffers from, for example, diseases caused by overexpression of the GPR40 of the present invention, or it is highly likely to suffer from these disease in the future.

The diseases associated with dysfunction of the GPR40 of the present invention include diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc. Diabetes mellitus includes insulin dependent (type I) diabetes mellitus, insulin non-dependent (type II) diabetes mellitus, etc.

The diseases caused by overexpression of the GPR40 of the present invention include, for example, obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity, cancer, etc.

(3) Pharmaceutical Comprising the Compound that Changes the Expression Level of the GPR40 of the Present Invention By using the DNA of the present invention as a probe, the DNA can be used for screening the compound that changes an expression level of the GPR40 of the present invention.

That is, the present invention provides methods of screening the compound that changes the expression level of the GPR40 of the present invention, which comprises measuring the amount of mRNA in the GPR40 of the present invention contained, for example, in (i) a) blood, b) particular organs, c) tissues or cells isolated from the organs of non-human mammals or in (ii) transformants, etc.

The amount of mRNA in the GPR40 of the present invention can be specifically measured as follows.

(i) Normal or disease models of non-human mammals (e.g., mice, rats, rabbits, sheep, swine, bovine, cats, dogs, monkeys, more specifically, rats with dementia, obese mice, rabbits with arteriosclerosis, tumor-bearing mice, etc.) receive administration of a drug (e.g., anti-dementia agents, hypotensive agents, anticancer agents, antiobestic agents, etc.) or physical stress (e.g., soaking stress, electric shock, light and darkness, low temperature, etc.), and the blood, particular organs (e.g., brain, liver, spleen, etc.), or tissues or cells isolated from the organs are obtained after a specified period of time.

The mRNA of the GPR40 of the present invention contained in the thus obtained cells is extracted from the cells, for example, in a conventional manner and quantified by means of, e.g., TaqManPCR, or may also be analyzed by northern blot technique by publicly known methods.

(ii) Transformants that express the GPR40 of the present invention are prepared according to the methods described above, and the mRNA of GPR40 of the present invention can be quantified and analyzed, as described above.

The compound that changes the expression level of the GPR40 of the present invention can be screened by the following procedures.

(i) To normal or disease models of non-human mammals, a test compound is administered at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of mRNA in the GPR40 of the present invention contained in cells are quantified and analyzed.

(ii) Transformants are cultured in a conventional manner and a test compound is mixed in the culture medium. After a specified time (after 1 day to 7 days, preferably after 1 day to 3 days, more preferably after 2 to 3 days), the amount of mRNA in the GPR40 of the present invention contained in the transformants can be quantified and analyzed.

The compound or its salt, which is obtained by the screening methods of the present invention, is the compound that changes the expression level of the GPR40 of the present invention. Specifically, it is (a) the compound that potentiates the cell stimulating activities mediated by GPR40 (e.g., the activities that promote or suppress arachidonic acid release, acetylcholine release, intracellular $Ca^{2+}$ release, intracellular cAMP production, intracellular cGMP production, inositol phosphate production, alters in cell membrane potential, phosphorylation of intracellular proteins, activation of c-fos, pH reduction, etc.) by increasing the expression level of the GPR40 of the present invention;

and (b) the compound that attenuates the cell-stimulating activities by decreasing the expression level of the GPR40 of the present invention.

The compounds include peptides, proteins, non-peptide compounds, synthetic compounds, fermentation products, etc. They may be novel or known compounds.

The ligand to the GPR40 of the present invention is the fatty acid or the eicosanoid, as described above. Accordingly, the compound that changes the expression level of the GPR40 of the present invention obtained by the screening methods described above can be used as a preventive and/or therapeutic agent for diseases associated with dysfunction of the GPR40 of the present invention.

Specifically, the compound that increases the expression level of the GPR40 of the present invention to potentiate the cell stimulating activities is useful as a safe and low toxic preventive/therapeutic agent for diseases associated with dysfunction of the GPR40 of the present invention, a pancreatic function regulating agent (e.g., a pancreatic function improving agent), an insulin secretagogue, a hypoglycemic agent, a pancreatic β cell protecting agent, etc.

The compound that decreases the expression level of the GPR40 of the present invention to attenuate the cell stimulating activities is useful as a safe and low toxic preventive/therapeutic agent for diseases caused by overexpression of the GPR40 of the present invention, a pancreatic function regulating agent (e.g., a pancreatic function improving agent), an insulin secretion suppressing agent or a hyperglycemic agent.

The diseases associated with dysfunction of the GPR40 of the present invention include diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc. Diabetes mellitus includes insulin dependent (type I) diabetes mellitus, insulin non-dependent (type II) diabetes mellitus, etc.

The diseases caused by overexpression of the GPR40 of the present invention include obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, etc.

As the salts of the compound, there are salts with physiologically acceptable acids (e.g., inorganic acids, organic acids, etc.), or bases (e.g., an alkaline metal such as sodium, potassium, etc.; an alkali earth metal such as calcium, etc.), with particular preference in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Hereinafter, the same are used as the salts.

Where the compound or its salt, which is obtained by the screening methods of the present invention, is used as a pharmaceutical composition, the compound or its salt can be prepared into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

Furthermore, the preventive/therapeutic agent described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. Th e thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salts varies depending on subject to be administered, target organ, conditions, methods for administration, etc.; in oral administration, the dose for a patient with diabetes mellitus (as 60 kg) is normally about 0.1 mg to about 100 mg, preferably about 1.0 to about 50 mg, and more preferably about 1.0 to about 20 mg per day. In parenteral administration, the single dose may vary depending on subject to be administered, target organ, conditions, methods for administration, etc. but it is advantageous to administer the active ingredient intravenously to a patient with diabetes mellitus (as 60 kg) in a daily dose of about 0.01 to about 30 mg, preferably about 0.1 to about 20 mg, and more preferably about 0.1 to about 10 mg. For other animal species, the corresponding dose as converted per 60 kg can be administered.

(4) Quantification of the GPR40 of the Present Invention and a Method for Diagnosis The antibodies of the present invention are capable of specifically recognizing the GPR40 of the present invention. Therefore, the antibodies can be used to quantify GPR40 in a test fluid, especially for quantification by the sandwich immunoassay, etc.

That is, the present invention provides, for example, the following quantification methods:

(i) a method for quantification of GPR40 in a test fluid, which comprises competitively reacting the antibody of the present invention with the test fluid and a labeled form of GPR40, and measuring a ratio of the labeled GPR40 bound to the antibody; and, (ii) a method for quantification of GPR40 in a test fluid, which comprises reacting the test fluid with the antibody of the present invention immobilized on a carrier and a labeled form of the antibody of the present invention simultaneously or sequentially, and measuring the activity of the label on the immobilized carrier.

In the quantification method (ii) described above, it is preferred that one antibody recognizes the N-terminal region of GPR40, and another antibody reacts with the C-terminal region of GPR40.

Using the monoclonal antibodies to GPR40, the GPR40 can be assayed. GPR40 can also be detected by tissue staining or the like. For this purpose, the antibody molecule itself may be used, or F(ab')$_2$, Fab' or Fab fractions of the antibody molecule may also be used.

The quantification methods of GPR40 using the antibodies are not particularly limited. Any quantification method can be used, so long as the amount of antibody, antigen, or antibody-antigen complex corresponding to the amount of antigen (e.g., the amount of GPR40) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the methods using labeled substances, there are employed, for example, radioisotopes, enzymes, fluorescent substances, luminescent substances, etc. For the radioisotope, for example, [$^{125}$I], [$^{131}$I], [$^3$H], [$^{14}$C] and the like are used. As the enzyme described above, stable enzymes with high specific activity are preferred; for example, β-galactosidase, β-glucosidase, alkaline phosphatase, peroxidase, malate dehydrogenase and the like are used. Examples of the fluorescent substance used are fluorescamine and fluorescein isothiocyanate are used. For the luminescent substance, there are used, for example, luminol, luminol derivatives, luciferin, and lucigenin. Furthermore, the biotin-avidin system may be used for binding antibody or antigen to the label.

For immobilization of antigen or antibody, physical adsorption may be used. Chemical binding methods conventionally used for insolubilization or immobilization of GPR40, enzymes or the like may also be used. For the carrier, for example, insoluble polysaccharides such as agarose, dextran, cellulose, etc.; synthetic resin such as polystyrene, polyacrylamide, silicon, etc., and glass or the like are used.

In the sandwich method, the immobilized monoclonal antibody of the present invention is reacted with a test fluid (primary reaction), then with the labeled monoclonal antibody of the present invention (secondary reaction), and the activity of the label on the immobilizing carrier is measured, whereby the amount of the GPR40 of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of assaying GPR40 by the sandwich method, antibodies that bind to different sites of GPR40 are preferably used as the monoclonal antibodies of the present invention for the primary and secondary reactions. That is, in the antibodies used for the primary and secondary reactions are, for example, when the antibody used in the secondary reaction recognizes the C-terminal region of GPR40, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, competitive method, immunometric method, nephrometry, etc.

In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the measurement methods of the present invention, any particular conditions or procedures are not required. Systems for measuring the GPR40 of the present invention are constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As described above, the GPR40 of the present invention can be quantified with high sensitivity, using the antibodies of the present invention.

Where a reduction in the GPR40 level is detected by quantifying the GPR40 level using the antibodies of the present invention, it can be diagnosed that one suffers from, for example, diseases associated with dysfunction of GPR40, or it is highly likely to suffer from these disease in the future.

Where an increase in the GPR40 level is detected, it can be diagnosed that one suffers from, for example, diseases caused by overexpression of GPR40, or it is highly likely to suffer from these disease in the future.

The diseases associated with dysfunction of the GPR40 of the present invention include diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc. Diabetes mellitus includes insulin dependent (type I) diabetes mellitus, insulin non-dependent (type II) diabetes mellitus, etc.

The diseases caused by overexpression of the GPR40 of the present invention include, for example, obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity, cancer, etc.

(5) Methods for Determination of Ligands to GPR40 Other than the Fatty Acid or Eicosanoid The fatty acid or eicosanoid binds to GPR40 so that an increase in intracellular $Ca^{2+}$ level and suppression of intracellular cAMP production is observed. Thus, GPR40 is useful as a reagent for searching or determining ligands to GPR40 other than the fatty acid or eicosanoid, using the intracellular signal as an indicator.

That is, the present invention provides a method of determining a ligand to GPR40, which comprises assaying the intracellular $Ca^{2+}$ level increasing activity or the intracellular cAMP production suppressing activity mediated by GPR40, when a test compound is brought in contact with a cell containing GPR40.

Examples of test compounds include publicly known ligands (for example, angiotensin, bombesin, canavinoid, cholecystokinin, glutamine, serotonin, melatonin, neuropeptide Y, opioids, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, the chemokine superfamily (e.g., the CXC chemokine subfamily such as IL-8, GROα, GROβ, GROγ, NAP-2, ENA-78, GCP-2, PF4, IP-10, Mig, PBSF/SDF-1, etc.; the CC chemokine subfamily such as MCAF/MCP-1, MCP-2, MCP-3, MCP-4, eotaxin, RANTES, MIP-1α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; the C chemokine subfamily such as lymphotactin, etc.; the CX3C chemokine subfamily such as fractalkine, etc.), endothelin, enterogastrin, histamin, neurotensin, TRH, pancreatic polypeptide, galanin, lysophosphatidic acid (LPA), sphingosine 1-phosphate, etc.) as well as other substances, for example, tissue extracts, cell culture supernatants from humans or mammals (e.g., mice, rats, swine, bovine, sheep, monkeys, etc.) or low molecular synthetic compound. For example, the tissue extract, or cell culture supernatant, is added to the receptor protein of the present invention while assaying the cell-stimulating activities and fractionating to finally obtain a single ligand.

Specifically, the ligand determination method of the present invention is a method of determining a compound or its salt having the GPR40-mediated intracellular $Ca^{2+}$ level increasing activities or intracellular cAMP production suppressing activities, which involves constructing the expression system of a recombinant GPR40 and assaying the GPR40-mediated cell stimulating activities by using the receptor-binding assay system using the aforesaid expression system.

More specifically, the present invention provides the following determination methods:

(1) a method of determining a ligand to GPR40, which comprises assaying intracellular $Ca^{2+}$ level increasing activities or intracellular cAMP production suppressing activities in the case where a test compound is brought into contact with cells containing GPR40; and (2) a method of determining a ligand to GPR40, which comprises assaying GPR40-mediated intracellular $Ca^{2+}$ level increasing activities or intracellular cAMP production suppressing activities in the case where a test compound is brought into contact with a receptor protein expressed on the cell membrane by culturing a transformant containing a DNA encoding GPR40.

In particular, it is preferred to carry out the test described above after the test compound binds to GPR40.

Where the cell containing GPR40 is used in the ligand determination methods of the present invention, the cell may be fixed using glutaraldehyde, formalin, etc. The fixation can be made by publicly known methods.

The membrane fraction of the cell containing GPR40 means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in GPR40 expressed and membrane components such as cell-derived phospholipids, membrane proteins, etc.

The amount of GPR40 in the cell or the cell membrane fraction is preferably $10^3$ to $10^8$ molecules per cell, more preferably $10^5$ to $10^7$ molecules per cell. As the level of expression increases, the ligand binding activity per unit of membrane fraction (specific activity) increases so that not only the highly sensitive screening system can be constructed but also large quantities of samples can be assayed with the same lot.

To perform the ligand determination method of the present invention, the GPR40-mediated intracellular $Ca^{2+}$ level increasing activities or intracellular cAMP production suppressing activities can be assayed by publicly known methods or using assay kits commercially available. Specifically, the cells containing GPR40 are first cultured on a multi-well plate, etc. Prior to the ligand determination, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the indicator substance (e.g., $Ca^{2+}$, cAMP, etc.) for the cell-stimulating activities due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production may then be detected.

The kit for ligand determination of the present invention contains the cell containing GPR40 or a membrane fraction of the cell.

The ligand thus determined binds to GPR40 to regulate its physiological functions and thus can be used as a preventive/therapeutic agent for diseases associated with the functions of GPR40.

(6) Method of Screening a Compound (Agonist, Antagonist, etc.) that Changes the Binding Properties of the GPR40 of the Present Invention to its Ligand and Pharmaceuticals Comprising the Compound that Changes the Binding Properties of the GPR40 of the Present Invention to its Ligand By using the GPR40 of the present invention, or by constructing the recombinant GPR40 expression system and using the receptor-binding assay system via the expression system, the compound (e.g., peptide, protein, a non-peptide compound, a synthetic compound, fermentation product, etc.) or salts thereof that change the binding properties of the ligand to the GPR40 of the present invention can be screened efficiently.

Examples of these compounds include (a) a compound showing the cell stimulating activities mediated by GPR40 (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.) (so-called agonists to the GPR40 of the present invention), (b) a compound having no such cell stimulating activities (so-called antagonists to the GPR40 of the present invention), (c) a compound that potentiates the binding properties of the ligand to the GPR40 of the present invention, or (d) a compound that decreases the binding properties of the ligand to the GPR40 of the present invention, and the like.

That is, the present invention provides a method of screening a compound or its salt that changes the binding properties of the GPR40 of the present invention and the ligand, which comprises comparing the following two cases: (i) the case wherein the GPR40 of the present invention is brought in contact with the ligand; and (ii) the case wherein the GPR40 of the present invention is brought in contact with the ligand and a test compound.

According to the screening method of the present invention, the method is characterized by assaying, e.g., the binding amount of the ligand to GPR40, the cell-stimulating activities, etc. in (i) and (ii) and comparing (i) and (ii).

More specifically, the present invention provides the following methods.

a) A method of screening a compound or a salt thereof that changes the binding properties of a ligand to the GPR40 of the present invention, which comprises measuring the binding amount of a labeled ligand to the GPR40 of the present invention in the case wherein the labeled ligand is brought in contact with the GPR40 of the present invention and in the case wherein the labeled ligand and a test compound are brought in contact with the GPR40 of the present invention, and comparing the cases.

b) A method of screening a compound or a salt thereof that changes the binding properties of a ligand to the GPR40 of the present invention, which comprises measuring the binding amount of a labeled ligand to a cell containing the GPR40 of the present invention or a membrane fraction of the cell, in the case wherein the labeled ligand is brought in contact with the cell containing the GPR40 of the present invention or the membrane fraction and in the case wherein the labeled ligand and a test compound are brought in contact with the cell containing the GPR40 or its membrane fraction, and comparing the cases.

c) A method of screening a compound or a salt thereof that changes the binding properties of a ligand to the GPR40 of the present invention, which comprises measuring the amount of a labeled ligand bound to the GPR40 of the present invention, in the case wherein the labeled ligand is brought in contact with the GPR40 expressed on a cell membrane by culturing a transformant containing the DNA of the present invention and in the case wherein the labeled ligand and a test compound are brought in contact with the GPR40 expressed on the cell membrane by culturing a transformant containing the DNA of the present invention, and comparing the cases.

d) A method of screening a compound or its salt that changes the binding properties of a ligand to the GPR40 of the present invention, which comprises assaying the GPR40-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.) in the case wherein a compound (e.g., a ligand, to the GPR40 of the present invention, etc.) that activates the GPR40 of the present invention is brought in contact with a cell containing the GPR40 of the present invention and in the case wherein said compound that activates the GPR40 of the present invention and a test compound are brought in contact with the cell containing the GPR40 of the present invention, and comparing the cell stimulating activities between the two cases.

e) A method of screening a compound or a salt thereof that changes the binding properties of a ligand to the GPR40 of the present invention, which comprises assaying the receptor-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.) in the case wherein a compound (e.g., a ligand to the GPR40 of the present invention) that activates the GPR40 of the present invention is brought in contact with the GPR40 of the present invention expressed on a cell membrane by culturing a transformant containing the DNA of the present invention and in the case wherein said compound that activates the GPR40 of the present invention and a test compound are brought in contact with the GPR40 of the present invention expressed on a cell membrane by culturing a transformant containing the DNA of the present invention, and comparing the cell stimulating activities between the two cases.

As the ligand, the fatty acid or eicosanoid described above is used.

In addition, a compound or its salt that changes the binding properties of the fatty acid or eicosanoid to GPR40 can also be used as the ligand. The compound or its salt that changes the binding properties of the fatty acid or eicosanoid to GPR40 can be obtained by carrying out the screening methods later described, using as the ligand, e.g., the fatty acid or eicosanoid.

The compound or its salt that changes the binding properties of the fatty acid or eicosanoid to GPR40 is preferably a low molecular synthetic compound, which may be novel or publicly known. Especially where the GPR40 antagonist is screened, it is preferred to use a low molecular synthetic compound having an agonist activity, in place of a naturally occurring ligand.

The low molecular synthetic compound is readily labeled as compared to the naturally occurring ligand and thus suitable for screening.

Hereinafter the screening method of the present invention will be described more specifically.

First, the GPR40 of the present invention, which is used for the screening method of the present invention, may be any one so long as it contains the GPR40 of the present invention described above, though membrane fractions from mammalian organs are preferably employed. Since it is very difficult to obtain human-derived organs especially, human-derived GPR40, etc. expressed abundantly by use of recombinants are suitable for use in the screening.

In manufacturing the GPR40 of the present invention, the methods described above can be used, and the DNA of the present invention is preferably expressed on mammalian cells or insect cells. As the DNA fragment encoding the target protein region, a complementary DNA may be used but is not limited thereto. For example, gene fragments or a synthetic DNA may also be used as the DNA fragment. In order to introduce the DNA fragment encoding the GPR40 of the present invention into host animal cells and express the same efficiently, the DNA fragment is preferably incorporated into a polyhedron promoter of nuclear polyhedrosis virus (NPV) belonging to the Baculovirus, an SV40-derived promoter, a promoter of retrovirus, a metallothionein promoter, a human heat shock promoter, a cytomegalovirus promoter, SRα promoter, etc. at the downstream thereof. The quantity and quality of the thus expressed receptors can be examined by a publicly known method, for example, by the method described in the literature [Nambi, P. et al., J. Biol. Chem., 267, 19555–19559, 1992].

Accordingly, in the screening method of the present invention, the substance containing the GPR40 of the present invention may be GPR40 purified by publicly known methods, or a cell containing the said GPR40 or a membrane fraction of the cell containing the GPR40 may be used as well.

Where the cell containing the GPR40 of the present invention is used in the screening method of the present invention, the cell may be fixed with glutaraldehyde, formalin, etc. The fixation may be carried out by a publicly known method.

The cell containing the GPR40 of the present invention refers to a host cell expressing the receptor protein. Examples of such a host cell include *Escherichia coli*, *Bacillus subtilis*, yeast, insect cells, animal cells, etc.

The membrane fraction of the cell containing GPR40 means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in GPR40 expressed and membrane components such as cell-derived phospholipids, membrane proteins, etc.

The amount of GPR40 in the cell or the cell membrane fraction is preferably $10^3$ to $10^8$ molecules per cell, more preferably $10^5$ to $10^7$ molecules per cell. As the level of expression increases, the ligand binding activity per unit of membrane fraction (specific activity) increases so that not only the highly sensitive screening system can be constructed but also large quantities of samples can be assayed with the same lot.

To perform a) through c) above for screening the compound that changes the binding properties of the ligand to the GPR40 of the present invention, an appropriate GPR40 fraction and a labeled ligand are required.

The GPR40 fraction is preferably a fraction of naturally occurring type GPR40 fraction or a recombinant GPR40 fraction having an activity equivalent thereto. Herein, the equivalent activity is intended to mean the ligand binding activity or the signal transduction activity, which is equivalent to the activity possessed by naturally occurring type GPR40.

As the labeled ligand, a labeled ligand, a labeled ligand analogue compound and the like are employed. For example, there are used ligands labeled with [$^3$H], [$^{125}$I], [$^{14}$C] [$^{35}$S], etc.

Specifically, the compound that changes the binding properties of the ligand to the GPR40 of the present invention is screened by the following procedures. First, a GPR40 preparation is prepared by suspending a cell containing the GPR40 of the present invention or a membrane fraction of the cell in a buffer appropriate for use in the screening method. Any buffer can be used so long as it does not interfere the ligand-GPR40 binding, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of the receptor or ligand by a protease, a protease inhibitor such as PMSF, leupeptin, E-64 (manufactured by Peptide Institute, Inc.), pepstatin, etc. may also be added. A given amount (5,000 cpm to 500,000 cpm) of the labeled ligand is added to 0.01 ml to 10 ml of the receptor solution, in which 10–4 M to 10—10 M of a test compound is co-present. To determine the amount of non-specific binding (NSB), a reaction tube containing an unlabeled ligand in a large excess is also provided. The reaction is carried out at approximately 0° C. to 50° C., preferably approximately 4° C. to 37° C. for about 20 minutes to about 24 hours, preferably about 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound.

The method d) or e) described above for screening the compound that changes the binding properties of the ligand to the GPR40 of the present invention can be performed as follows. For example, the GPR40-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.) can be determined by a publicly known method, or using an assay kit commercially available.

Specifically, the cells containing the GPR40 of the present invention are first cultured in a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., $Ca^{2+}$, cAMP, etc.) due to a degrading enzyme contained in the cells, an inhibitor against such as a degrading enzyme may be added prior to the assay. For detecting the activities such as the cAMP production suppression activity, the baseline production in the cells is increased by forskolin or the like and the suppressing effect on the increased baseline production can be detected.

For screening through the assay for the cell stimulating activities, cells, in which an appropriate GPR40 has been expressed, are necessary. P referred cells, in which the GPR40 of the present invention has been expressed, are a naturally occurring type cell line containing the GPR40 of the present invention and the aforesaid cell line, in which recombinant type GPR40 has been expressed.

Examples of the test compounds include peptides, proteins, non-peptide compounds, synthetic compounds, fermentation products, cell extracts, plant extracts, animal tissue extracts, etc. These test compounds may be either novel or publicly known compounds.

The test compound which is preferably used is a compound designed to bind to the ligand-binding pocket, based on the atomic coordinate and the position of the ligand-binding pocket in the active site of GPR40. The atomic coordinate and the position of the ligand-binding pocket in the active site of GPR40 can be determined by publicly known methods or modifications thereof.

Following (i) or (ii) below, it can be specifically assessed whether the compound that changes the binding properties of the ligand to the GPR40 of the present invention is either an agonist or an antagonist.

(i) The screening methods of a) to c) described above are performed to obtain the compound or its salt that changes the binding properties of the ligand to the GPR40 of the present invention (especially inhibits the binding). Then, it is determined whether or not the compound or its salt possesses the cell stimulating activities described above. Specifically, this can be confirmed by using the screening methods of agonists to the GPR40 of the present invention described above, and the compound having the cell stimulating activities or its salt is an agonist, whereas the compound having no cell stimulating activity or its salt is an antagonist.

(ii) (a) A test compound is brought in contact with a cell containing the GPR40 of the present invention to assay the cell stimulating activities described above. The test compound having the cell stimulating activities is an agonist to the GPR40 of the present invention.

(b) The cell stimulating activities are assayed in the case wherein a compound that activates the GPR40 of the present invention (e.g., a ligand) is brought in contact with a cell containing the GPR40 of the present invention and in the case wherein a compound that activates the GPR40 of the present invention and a test compound are brought in contact with a cell containing the GPR40 of the present invention, and comparison is made therebetween. The test compound, which can decrease the cell stimulating activities mediated by the compound that activates the GPR40 of the present invention, is an antagonist to the GPR40 of the present invention.

More specifically, the assessment criterion described in EXAMPLE 35 can be used for the assessment.

The kit for screening the compound or its salt that changes the binding properties of the ligand to the GPR40 of the present invention is a kit comprising the GPR40 of the present invention, a cell containing the GPR40 of the present invention, or a membrane fraction of the cell containing the GPR40 of the present invention, and the like.

Examples of the screening kit of the present invention include the following.

1. Reagent for Screening a) Assay Buffer and Wash Buffer

Hanks' balanced salt solution (manufactured by Gibco, Inc.) supplemented with 0.05% bovine serum albumin (manufactured by Sigma, Inc.)

The solution is sterilized by filtration through a 0.45 μm filter, and stored at 4° C. or may be prepared at use.

b) GPR40 Preparation

CHO cells wherein the GPR40 of the present invention has been expressed are passaged in a 12-well plate at a density of $5×10^5$ cells/well followed by culturing at 37° C. under 5% $CO_2$ and 95% air for 2 days.

c) Labeled Ligand

An aqueous solution of the ligand labeled with commercially available [$^3$H], [$^{125}$I], [$^{14}$C], [$^{35}$S], etc. is stored at 4° C. or −20° C., and diluted to 1 μM with the assay buffer upon use.

d) Standard Ligand Solution

The ligand is dissolved in and adjusted to 1 mM with PBS containing 0.1% bovine serum albumin (manufactured by Sigma, Inc.) and stored at −20° C.

2. Assay Method a) CHO cells wherein the GPR40 of the present invention has been expressed are cultured in a 12-well culture plate and washed twice with 1 ml of the assay buffer, and 490 μl of the assay buffer is added to each well.

b) After adding 5 μl of $10^{-3}$–$10^{-10}$ M test compound solution, 5 μl of a labeled ligand is added to the mixture, and the cells are incubated at room temperature for an hour. To determine the amount of the non-specific binding, 5 μl of the non-labeled ligand is added in place of the test compound.

c) The reaction solution is removed, and the wells are washed 3 times with the washing buffer. The labeled ligand bound to the cells is dissolved in 0.2N NaOH-1% SDS, and mixed with 4 ml of liquid scintillator A (manufactured by Wako Pure Chemical Industries, Ltd.)

d) The radioactivity is measured using a liquid scintillation counter (manufactured by Beckman Co.), and the percent maximum binding (PMB) is calculated by the equation below.

$$PMB=[(B-NSB)/(B_0-NSB)]\times 100$$

| | |
|---|---|
| PMB | Percent maximum binding |
| B | Value obtained in the presence of a test compound |
| NSB | Non-specific binding |
| $B_0$ | Maximum binding |

The compound or its salt, which is obtained by using the screening methods or the screening kits of the present invention, is the compound that changes the binding properties of the ligand to the GPR40 of the present invention. Specifically, the compound is: (a) a compound having the cell-stimulating activities mediated by the G protein-coupled receptor (a so-called agonist to the GPR40 of the present invention); (b) a compound having no cell stimulating activity (a so-called antagonist to the GPR40 of the present invention); (c) a compound that potentiates the binding affinity of the ligand to the G protein-coupled GPR40 of the present invention; or (d) a compound that reduces the binding affinity of the ligand to the G protein-coupled GPR40 of the present invention.

These compounds may be peptides, proteins, non-peptide compounds, synthetic compounds, fermentation products, and may be novel or known compounds.

Also, the compounds may be those designed based on the atomic coordinate and the position of the ligand-binding pocket in the active site of GPR40 described above.

Since the agonists to the GPR40 of the present invention have the same physiological activities as those of the fatty acid or eicosanoid, which is a ligand to the GPR40 of the present invention, the agonists are useful as safe and low toxic pharmaceuticals, correspondingly to the physiological activities possessed by the fatty acid or eicosanoid.

Since the antagonists to the GPR40 of the present invention can suppress the physiological activities possessed by the fatty acid or eicosanoid, which is a ligand to the GPR40 of the present invention, the antagonists are useful as safe and low toxic pharmaceuticals to suppress the physiological activities of the fatty acid or eicosanoid.

The compound that potentiates the binding affinity of the ligand to the G protein-coupled GPR40 of the present invention can potentiate the physiological activities the ligand to the GPR40 of the present invention has. Thus, the compound is useful as a safe and low toxic pharmaceutical correspondingly to the physiological activities the fatty acid or eicosanoid possesses.

The compound that reduces the binding affinity of the ligand to the G protein-coupled GPR40 of the present invention can reduce the physiological activities the ligand to the GPR40 of the present invention has. Thus, the compound is useful as a safe and low toxic pharmaceutical to suppress the physiological activities the fatty acid or eicosanoid possesses.

Specifically, (i) the agonist to GPR40 or (ii) the compound or its salt that potentiates the binding affinity of the ligand to the G protein-coupled GPR40 of the present invention, which is obtained by using the screening methods or screening kits of the present invention, is useful as a preventive/therapeutic agent for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc., a pancreatic function regulating agent (e.g., a pancreatic function improving agent), an insulin secretagogue, a hypoglycemic agent, a pancreatic β cell protecting agent, etc. Diabetes mellitus includes insulin dependent (type I) diabetes mellitus, insulin non-dependent (type II) diabetes mellitus, etc.

(i) The antagonist to GPR40 or (ii) the compound or its salt that reduces the binding affinity of the ligand to the G protein-coupled GPR40 of the present invention, which is obtained by using the screening methods or screening kits of the present invention, is useful as a preventive/therapeutic agent for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity, cancer, etc., a pancreatic function regulating agent (e.g., a pancreatic function improving agent), an insulin secretion suppressing agent or a hyperglycemic agent.

The compound or its salt, which is obtained by using the screening methods or screening kits of the present invention, can be used in combination with the compound or its salt that changes the expression level of GPR40 later described, other drugs for the diseases described above, drugs such as other antidiabetic agents, therapeutic agents for diabetic complications, antihyperlipidemic agents, hypotensive agents, antiobestic agents, diuretic agents, chemotherapeutic agents, immunotherapeutic agents, etc. (hereinafter sometimes referred to briefly as concomitant drugs). On such occasions, the time for administering the compound or its salt obtained by using the screening methods or screening kits of the present invention and concomitant drugs are not limited, and they may be administered simultaneously or at staggered times to the subject to be administered. The dose of the concomitant drug can be appropriately selected based on the dose which is clinically employed. A ratio of the compound or its salt obtained by using the screening methods or screening kits of the present invention to the concomitant drug can be appropriately selected, depending on the subject to be administered, administration route, target disease, clinical conditions, combination, etc. In cases where the subject administered is human, for instance, the concomitant drug may be used, for example, in an amount of 0.01 to 100 parts by weight per part by weight of the agonist.

Examples of the other therapeutic agents for diabetes include insulin preparations (e.g., animal insulin preparations extracted from the bovine or porcine pancreas; human insulin preparations synthesized by a genetic engineering technique using *Escherichia coli* or a yeast; insulin-zinc; protamine-insulin-zinc; insulin fragments or derivatives (e.g., INS-1, etc.) or the like), insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanide preparations (e.g., phenformin, metformin, buformin, etc.), sulfonylurea preparations (e.g., tolbutamide, glibenclamide, gliclazide, chlorpropamide, tolazamide, acetohexamide, glyclopyramide, glimepiride, etc.), and other insulin secretagogues (e.g., repaglinide, senaglinide, mitiglinide or its calcium salt hydrate, GLP-1, nateglinide), dipeptidylpeptidase IV inhibitors (e.g., NVP-DPP-278, PT-100, P32/98, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatse inhibitors, glucagon antagonists, etc.), SGLT (sodium-glucose cotransporter) inhibitors (e.g., T-1095, etc.) and the like.

Examples of the therapeutic agents for diabetic complications include aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, protein kinase C (PKC) inhibitors (e.g., LY-333531, etc.) and the like), AGE inhibitors (e.g., ALT-945, pimagedine, pyratoxathine, N-phenacylthiazolinium bromide (ALT-766), EXO-226, etc.), active oxygen scavengers (e.g., thioctic acid, etc.), cerebral vasodilators (e.g., tiapride), and the like.

Examples of the antihyperlipidemic agents include statin compounds which are cholesterol synthesis inhibitors (e.g., pravastatin, simvastatin, lovastatin, atorvastatin, fluvastatin, cerivastatin or salts thereof (e.g., sodium salts, etc.) and the like), squalene synthase inhibitors or fibrate compounds having a triglyceride lowering action (e.g., bezafibrate, clofibrate, simfibrate, clinofibrate, etc.), and the like.

Examples of the hypotensive agents include angiotensin converting enzyme inhibitors (e.g., captopril, enalapril, delapril, etc.), angiotensin II antagonists (e.g., losartan, candesartan, cilexetil, etc.), calcium antagonist (e.g., manidipine, nifedipine, amlodipine, efonidipine, nicardipine, etc.), clonidine, and the lie.

Examples of the antiobestic agents include antiobestic drugs acting on the central nervous system (e.g., dexfenfluramine, fenfluramine, phentermine, sibutramine, anfepramon, dexamphetamine, mazindol, phenylpropanolamine, clobenzorex, etc.), pancreatic lipase inhibitors (e.g., orlistat, ATL-962, etc.), β3 agonists (e.g., CL-316243, SR-58611-A, UL-TG-307, AJ-9677, AZ40140, etc.), anorectic peptides (e.g., leptin, CNTF (ciliary neurotrophic factor), etc.), cholecystokinin agonists (e.g., lintitript, FPL-15849, etc.), and the like.

Examples of the diuretic agents include xanthine derivatives (e.g., theobromine sodium salicylate, theobromine calcium salicylate, etc.), thiazide type preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide type preparations (e.g., chlorthalidone, mefruside, indapamide, etc.), azosemide, isosorbide, ethacrynic acid, piretanide, bumetanide, furosemide, etc.

Examples of the chemotherapeutic agent include alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, Taxol, etc.), cisplatin, carboplatin, etoposide, etc. Among these, 5-fluorouracil derivatives such as Furtulon and Neo-Furtulon are preferred.

Examples of the immunotherapeutic agent include microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating agents (e.g., granulocyte colony stimulating factor, erythropoietin, etc.) and the like. Among others, IL-1, IL-2, IL-12 and the like are preferred.

Further, agents whose effects of ameliorating cachexia have been confirmed in animal models or clinically, that is, cyclooxygenase inhibitors (e.g., indomethacin, etc.) (Cancer Research, 49, 5935–5939, 1989), progesterone derivatives (e.g., megestrol acetate, etc.) (Journal of Clinical Oncology, 12, 213–225, 1994), glucocorticoids (e.g., dexamethasone, etc.), metoclopramide type pharmaceuticals, tetrahydrocannabinol type pharmaceuticals (the same references are applied to above), fat metabolism ameliorating agents (e.g., eicosapentanoic acid, etc.) (British Journal of Cancer, 68, 314–318, 1993), growth hormones, IGF-1, and antibodies to the cachexia-inducing factor TNF-α, LIF, IL-6 or oncostatin M, can also be used in combination with the preparations of the invention.

Furthermore, glycation inhibitors (e.g., ALT-711, etc.), nerve regeneration stimulators (e.g., Y-128, VX853, prosaptide, etc.), antidepressants (e.g., desipramine, amitriptyline, imipramine, etc.), anticonvulsant (e.g., lamotrigine), antiarrhythmics (e.g., mexiletine), acetylcholine receptor ligands (e.g., ABT-594), endothelin receptor antagonists (e.g., ABT-627), monoamine reuptake inhibitors (e.g., tramadol), narcotic analgesics (e.g., morphine), GABA receptor agonists (e.g., gabapentin), α2 receptor ligands (e.g., clonidine), local analgesics (e.g., capsaicin), anxiolytics (e.g., benzodiazepine), phosphodiesterase inhibitors (e.g., sildenafil), dopamine receptor ligands (e.g., apomorphine), etc. can be used in combination with the preparation of the present invention.

Where the compound or its salt, which is obtained by using the screening methods or screening kits of the present invention, is used as the pharmaceutical composition above, the compound or its salt can be prepared into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, and may be used in combination with a dissolution aid such as benzyl benzoate, benzyl alcohol, etc.

Furthermore, the preventive/therapeutic agent described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salts varies depending on subject to be administered, target organ, conditions, route for administration, etc.; in oral administration, the dose for a patient with diabetes mellitus (as 60 kg) is normally about 0.1 mg to about 100 mg, preferably about 1.0 to about 50 mg, and more preferably about 1.0 to about 20 mg per day. In parenteral administration, the single dose may vary depending on subject to be administered, target organ, conditions, method for administration, etc. but it is advantageous to administer the active ingredient intravenously to a patient with diabetes mellitus (as 60 kg) in a daily dose of about 0.01 to about 30 mg, preferably about 0.1 to about 20 mg, and more preferably about 0.1 to about 10 mg. For other animal species, the corresponding dose as converted per 60 kg can be administered.

(7) Methods for Elucidation of the Action Mechanism of Various Drugs

By using the GPR40 of the present invention, it can be confirmed whether or not various drugs exhibit their pharmacological effects mediated by GPR40.

That is, the present invention provides the following methods.

(1) A method of confirmation that (i) a pancreatic function regulating drug (e.g., a pancreatic function improving drug), (ii) a preventive/therapeutic drug for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, (iii) an insulin secretagogue, (iv) a hypoglycemic drug, (v) a pancreatic β cell protecting drug or (vi) a preventive/therapeutic drug for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer binds to the receptor protein or its salt, which comprises using GPR40.

(2) A method of confirmation that (i) a preventive/therapeutic drug for diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia or deficits in memory, (ii) an insulin secretagogue, (iii) a hypoglycemic drug or (v) pancreatic β cell protection is an agonist to the receptor protein or its salt, which comprises using GPR40.

(3) A method of confirmation that (i) a preventive/therapeutic drug for obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity or cancer, (ii) an insulin secretion suppressing drug or (iii) a hyperglycemic drug is an antagonist to the receptor protein or its salt, which comprises using GPR40.

(4) The screening method according to (1) to (3), wherein the binding amount of each drug to GPR40 is measured when the drug is brought in contact with GPR40.

This confirmation method can be performed by using the drug described above in lieu of the test compound in the aforesaid method of screening the compound that changes the binding properties of the ligand to GPR40.

The kit used for the method of confirmation of the present invention contains the drug described above in place of the test compound, in the aforesaid kit for screening the compound that changes the binding properties of the ligand to GPR40.

By using the method of confirmation of the present invention as such, it can be confirmed that various drugs commercially available or under development exhibit their pharmacological effects mediated by GPR40.

(8) Pharmaceutical Comprising the Compound that Changes the Amount of the GPR40 of the Present Invention or its Partial Peptide in Cell Membrane The antibody of the present invention is capable of specifically recognizing the GPR40 of the present invention and can be used for screening the compound that changes the amount of the GPR40 of the present invention in the cell membrane.

That is, the present invention provides the following methods:

(i) a method of screening the compound that changes the amount of the GPR40 of the present invention in the cell membrane, which comprises measuring the amount of the GPR40 of the present invention contained in a) blood, b) particular organs or c) a cell membrane fraction isolated after disrupting tissues or cells isolated from the organs of non-human mammals;

(ii) a method of screening the compound that changes the amount of the GPR40 of the present invention in the cell membrane, which comprises disrupting transformants, etc. expressing the GPR40 of the present invention, isolating the cell membrane fraction and quantifying the GPR40 of the present invention contained in the cell membrane fraction; and, (iii) a method of screening the compound that changes the amount of the GPR40 of the present invention in the cell membrane, which comprises preparing a slice of a) blood, b) particular organs or c) tissues, cells, etc. isolated from organs of non-human mammals and quantifying the stained receptor protein on the cell surface using immunostaining assay thereby to confirm the protein on the cell membrane.

The present invention provides:

(iv) a method of screening the compound that changes the amount of the GPR40 of the present invention in the cell membrane, which comprises preparing a slice of a transformant expressing the GPR40 of the present invention and quantifying the stained receptor protein on the cell surface using immunostaining assay thereby to confirm the protein on the cell membrane.

Specifically, the GPR40 of the present invention contained in the cell membrane fraction can be measured as follows.

(i) Normal or disease models of non-human mammals (e.g., mice, rats, rabbits, sheep, swine, bovine, cats, dogs, monkeys, more specifically, rats with dementia, obese mice, rabbits with arteriosclerosis, tumor-bearing mice, etc.) receive administration of a drug (e.g., an anti-dementia drug, a hypotensive drug, an anticancer agent, an antiobestic drug, etc.) or physical stress (e.g., soaking stress, electric shock, light and darkness, low temperature, etc.), and the blood, particular organs (e.g., brain, liver, spleen, etc.), or tissues or cells isolated from the organs are obtained after a specified period of time. The obtained organs, tissues, cells or the like are suspended in, for example, an appropriate buffer (e.g., Tris hydrochloride buffer, phosphate buffer, HEPES buffer, etc.), and the organs, tissues or cells are disrupted, and the cell membrane fraction is obtained using surfactants (e.g., Triton-X 100™, Tween 20™) and further using techniques such as centrifugal separation, filtration, column fractionation, etc.

The membrane fraction of the cell containing GPR40 means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in GPR40 expressed and membrane components such as cell-derived phospholipids, membrane proteins, etc.

The GPR40 of the present invention contained in the cell membrane fraction can be quantified by, for example, the sandwich immunoassay, western blot analysis, etc. using the antibody of the present invention.

The sandwich immunoassay can be performed as described above, and the western blot can be performed by publicly known methods.

(ii) Transformants expressing the GPR40 of the present invention are prepared by the method described above, and the GPR40 of the present invention contained in the cell membrane fraction can be quantified.

The compound that changes the amount of the GPR40 of the present invention in cell membranes can be screened as follows.

(i) Normal non-human mammal or disease model of non-human mammal is administered with a test compound at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of the GPR40 of the present invention in the cell membranes can be quantified.

(ii) Transformants are cultured in a conventional manner and a test compound is mixed in the culture medium. After a specified time (after 1 day to 7 days, preferably after 1 day to 3 days, more preferably after 2 to 3 days), the amount of the GPR40 of the present invention in the cell membranes can be quantified.

Specifically, the GPR40 of the present invention contained in cell membrane fractions is confirmed as follows.

(iii) Normal non-human mammals or disease models of non-human mammals (e.g., mice, rats, rabbits, sheep, swine, bovine, cats, dogs, monkeys, etc., more specifically, rats with dementia, obese mice, rabbits with arteriosclerosis, tumor-bearing mice, etc.) are administered with drugs (e.g., anti-dementia agents, hypotensive agents, anticancer agents, antiobestic agents, etc.) or physical stress (e.g., soaking stress, electric shock, light and darkness, low temperature, etc.) or the like, and blood or particular organ (e.g., brain, liver, kidney, etc.), or the tissues or cells isolated from the organ are obtained after a specified period of time. Tissue sections are prepared from the thus obtained organs, tissues, cells, etc. in a conventional manner followed by immunostaining with the antibody of the present invention. The staining intensity of the receptor protein on the cell surface is quantified to confirm the protein on the cell membrane, whereby the amount of the GPR40 of the present invention on the cell membrane can be confirmed quantitatively or qualitatively.

(iv) The confirmation can also be made by the similar method, using transformants expressing the GPR40 of the present invention.

The compounds or its salts obtained by the screening methods of the present invention are the compounds that have the action of changing the amount of the GPR40 of the present invention. Specifically, these compounds are: (a) compounds that increase the amount of the GPR40 of the present invention in cell membranes thereby to potentiate the G protein-coupled receptor-mediated cell-stimulating activities (e.g., the activities that promote or inhibit arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc.); and (b) compounds that decrease the amount of the GPR40 of the present invention thereby to attenuate the cell stimulating-activities.

The compounds may be peptides, proteins, non-peptide compounds, synthetic compounds, fermentation products, and may be novel or publicly known compounds.

The compounds that increase the amount of the GPR40 of the present invention thereby to potentiate the cell-stimulating activities are useful as safe and low toxic preventive/therapeutic agents, pancreatic function regulating drugs, insulin secretagogues, hypoglycemic drugs and pancreatic β cell protecting drugs.

The compound that decreases the expression level of the GPR40 of the present invention thereby to attenuate the cell stimulating activities is useful as a safe and low toxic preventive/therapeutic agent for diseases caused by overexpression of the GPR40 of the present invention, a pancreatic function regulating agent (e.g., a pancreatic function improving agent), an insulin secretion suppressing agent or a hyperglycemic agent.

Specifically, the compound or its salt that increases the amount of the GPR40 of the present invention can be used as a preventive/therapeutic agent for diseases, e.g., diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc. Diabetes mellitus includes insulin dependent (type I) diabetes mellitus, insulin non-dependent (type II) diabetes mellitus, etc.

The compound or its salt that decreases the amount of the GPR40 of the present invention can be used as a preventive/therapeutic agent for diseases, e.g., obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity, cancer, etc.

The preventive/therapeutic agent can be used in combination with the concomitant drugs described above.

Where the compound or its salt, which is obtained by using the screening methods of the present invention, is used as the pharmaceutical composition above, the compound or its salt can be prepared into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

Furthermore, the preventive/therapeutic agent described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. Th e thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salts varies depending on subject to be administered, target organ, conditions, methods for administration, etc.; in oral administration, the dose for a patient with diabetes mellitus (as 60 kg) is normally about 0.1 mg to about 100 mg, preferably about 1.0 to about 50 mg, and more preferably about 1.0 to about 20 mg per day. In parenteral administration, the single dose may vary depending on subject to be administered, target organ, conditions, methods for administration, etc. but it is advantageous to administer the active ingredient intravenously to a patient with diabetes mellitus (as 60 kg) in a daily dose of about 0.01 to about 30 mg, preferably about 0.1 to about 20 mg, and more preferably about 0.1 to about 10 mg. For other animal species, the corresponding dose as converted per 60 kg can be administered.

(9) Pharmaceutical Comprising the Antibody to the GPR40 of the Present Invention The neutralizing activity of the antibody to the GPR40 of the present invention means the activity of inactivating the signal transduction function in which the GPR40 takes part. Thus, when the antibody has the neutralizing activity, the antibody can inactivate signal transduction in which the GPR40 takes part, for example, the GPR40-mediated cell stimulating activities (e.g., the activities that promote or inhibit arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc.).

Therefore, the neutralizing antibody to the GPR40 of the present invention can be used as a preventive/therapeutic agent for diseases caused by overexpression of GPR40, etc. (e.g., obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity, cancer, etc.), a pancreatic function regulating agent (e.g., a pancreatic function improving agent), an insulin secretion suppressing agent or a hyperglycemic agent.

Also, the neutralizing antibody can be used in combination with the concomitant drugs described above.

(10) Pharmaceutical Comprising the Antisense DNA or siRNA of the Present Invention The antisense DNA or siRNA of the present invention can be used as a preventive/therapeutic agent for diseases caused by overexpression of GPR40 (e.g., obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity, cancer, etc.), a pancreatic function regulating agent (e.g., a pancreatic function improving agent), an insulin secretion suppressing agent or a hyperglycemic agent.

The antisense DNA or siRNA can be used in combination with the concomitant drugs described above.

For example, where the antisense DNA or siRNA is used, the antisense DNA or siRNA itself is administered; alternatively, the antisense DNA or siRNA is inserted into an appropriate vector such as retrovirus vector, adenovirus vector, adenovirus-associated virus vector, etc. and then administered in a conventional manner. The antisense DNA may also be administered as naked, or with adjuvants to assist its uptake by gene gun or through a catheter such as a catheter with a hydrogel.

In addition, the antisense DNA may also be used as an oligonucleotide probe for diagnosis to investigate the presence of the DNA of the present invention or the state of its expression in tissues or cells.

(11) Preparation of Animal Bearing the DNA of the Present Invention

The present invention provides a non-human mammal bearing DNA which is exogenous (hereinafter briefly referred to as the exogenous DNA of the present invention) or its variant DNA (sometimes briefly referred to as the exogenous variant DNA of the present invention).

That is, the present invention provides:
[1] A non-human mammal bearing the exogenous DNA of the present invention or its variant DNA;
[2] The mammal according to [1], wherein the non-human mammal is a rodent;
[3] The mammal according to [2], wherein the rodent is mouse or rat; and,
[4] A recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be produced by transferring a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfer the exogenous DNA of the present invention into a somatic cell, a living organ, a tissue cell, or the like by the DNA transfer, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57B1/6 strain, DBA2 strain, etc. for a pure line and for a cross line, B6C3F$_1$, strain, BDF$_1$, strain B6D2F$_1$, strain, BALB/c strain, ICR strain, etc.), rats (Wistar, SD, etc.) or the like, since they are relatively short in ontogeny and life cycle from a standpoint of producing model animals for human disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses the abnormal GPR40 of the present invention and exemplified by the DNA that expresses GPR40 for suppressing the function of the normal GPR40 of the present invention.

The exogenous DNA of the present invention may be any one of those derived from a mammal of the same species as, or a different species from, the mammal as the target animal. In transferring the DNA of the present invention, it is generally advantageous to use the DNA as a DNA construct in which the DNA is ligated downstream a promoter capable of expressing the DNA in the target animal. For example, in the case of transferring the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the GPR40 of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal GPR40 of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal GPR40 obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transferred can be passaged as the DNA-bearing animal under ordinary rearing environment, by confirming that the exogenous DNA is stably retained by crossing.

By transfer of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfer means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygous animals having the transferred DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the GPR40 of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the GPR40 of the present invention and the pathological mechanism of the disease associated with the GPR40 of the present invention and to investigate how to treat these diseases.

Furthermore, since a mammal transferred with the exogenous normal DNA of the present invention exhibits an increasing symptom of the GPR40 of the present invention liberated, the animal is usable for screening of an drug for the treatment of diseases associated with the GPR40 of the present invention.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfer of the abnormal DNA of the present invention at the fertilized egg cell stage is preserved to be present in all of the germinal and somatic cells of the target mammal. The fact that the abnormal DNA of the present invention is present in the germinal cells of the animal after DNA transfer means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the GPR40 of the present invention by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the GPR40 of the present invention and the pathological mechanism of the disease and to investigate how to treat the disease.

More specifically, the transgenic animal of the present invention expressing the abnormal DNA of the present invention at a high level is expected to serve as an experimental model to elucidate the mechanism of the functional inhibition (dominant negative effect) of a normal GPR40 by the abnormal GPR40 of the present invention in the function inactive type inadaptability of the GPR40 of the present invention.

A mammal bearing the abnormal exogenous DNA of the present invention is also expected to serve for screening a candidate drug for the treatment of the function inactive type inadaptability of the GPR40 of the present invention, since a free form of the GPR40 of the present invention is increased in such an animal.

Other potential applications of two kinds of the DNA transgenic animals of the present invention described above further include, for example:

(1) Use as a cell source for tissue culture;
(2) Elucidation of the relation to GPR40 that is specifically expressed or activated by the GPR40 of the present invention, by direct analysis of DNA or RNA in tissues of the DNA transgenic animal of the present invention or by analysis of the GPR40 tissues expressed by the DNA;
(3) Research on the function of cells derived from tissues that are usually cultured only with difficulty, using cells in tissues bearing the DNA cultured by a standard tissue culture technique;
(4) Screening a drug that enhances the functions of cells using the cells described in (3) above; and,
(5) Isolation and purification of the variant GPR40 of the present invention and preparation of an antibody thereto.

Furthermore, clinical conditions of a disease associated with the GPR40 of the present invention, including the function inactive type inadaptability to the GPR40 of the present invention can be determined by using the DNA transgenic animal of the present invention. Also, pathological findings on each organ in a disease model associated with the GPR40 of the present invention can be obtained in more detail, leading to the development of a new method for treatment as well as the research and therapy of any secondary diseases associated with the disease.

It is also possible to obtain a free DNA-transferred cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the GPR40 of the present invention, and to study in association with apoptosis, differentiation or propagation or on the mechanism of signal transduction in these properties to inspect any abnormality therein. Thus, the DNA transgenic animal can provide an effective research material for the GPR40 of the present invention and for investigation of the function and effect thereof.

To develop a drug for the treatment of diseases associated with the GPR40 of the present invention, including the function inactive type inadaptability to the GPR40 of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the GPR40 of the present invention, using the DNA transgenic animal of the present invention or a vector capable of expressing the exogenous DNA of the present invention.

(12) Knockout Animal

The present invention provides a non-human mammalian embryonic stem cell bearing the DNA of the present invention inactivated and a non-human mammal deficient in expressing the DNA of the present invention.

Thus, the present invention provides:

[1] A non-human mammalian embryonic stem cell in which the DNA of the present invention is inactivated;
[2] The embryonic stem cell according to [1], wherein the DNA is inactivated by introducing a reporter gene (e.g., β-galactosidase gene derived from *Escherichia coli*);
[3] The embryonic stem cell according to [1], which is resistant to neomycin;
[4] The embryonic stem cell according to [1], wherein the non-human mammal is a rodent;
[5] The embryonic stem cell according to [4], wherein the rodent is mouse;
[6] A non-human mammal deficient in expressing the DNA of the present invention, wherein the DNA is inactivated;
[7] The non-human mammal according to [5], wherein the DNA is inactivated by inserting a reporter gene (e.g., β-galactosidase derived from *Escherichia coli*) therein and the reporter gene is capable of being expressed under control of a promoter for the DNA of the present invention;
[8] The non-human mammal according to [6], which is a rodent;
[9] The non-human mammal according to [8], wherein the rodent is mouse; and,
[10] A method of screening a compound that promotes or inhibits (preferably inhibits) the promoter activity to the DNA of the present invention, which comprises administering a test compound to the mammal of [7] and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the GPR40 of the present invention (hereinafter sometimes referred to as the knockout DNA of the present invention) by substantially inactivating the activities of the GPR40 of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter simply referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for studying the GPR40 of the present invention in vitro or the GPR40 of the present invention cytologically.

The non-human mammal deficient in expression of the DNA of the present invention can be identified from a normal animal by measuring the mRNA level in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transferring a targeting vector, prepared as described above, to mouse embryonic stem cells or mouse oocytes, and conducting homologous recombination in which a targeting vector DNA sequence, wherein the DNA of the present invention is inactivated by the transfer, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the GPR40 of the present invention. The individuals deficient in homozygous expression of the GPR40 of the present invention can be obtained from offspring of the intercross between those deficient in heterozygous expression of the GPR40 of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygous animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the GPR40 of the present invention, such an animal can be a disease model suspected of inactivated biological activities of the GPR40 of the present invention and thus, offers an effective study to investigate the causes for and therapy for these diseases.

(12a) Method of Screening a Compound Having a Therapeutic/Preventive Effect on Diseases Caused by Deficiency, Damages, etc. of the DNA of the Present Invention The non-human mammal deficient in expression of the DNA of the present invention can be employed for screening of a compound having a therapeutic/preventive effect on diseases caused by deficiency, damages, etc. of the DNA of the present invention.

That is, the present invention provides a method of screening a compound having a therapeutic/preventive effect on diseases caused by deficiency, damages, etc. of the DNA of the present invention, which comprises administering a test compound to a non-human mammal deficient in expression of the DNA of the present invention and, observing and measuring a change occurred in the animal.

As the non-human mammal deficient in expression of the DNA of the present invention, which can be employed for the screening method, the same examples as given hereinabove apply.

Examples of the test compound include peptides, proteins, non-peptide compounds, synthetic compounds, fermentation products, cell extracts, plant extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/preventive effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately selected depending on the administration methods, nature of the test compound, etc.

When a test compound is administered to a test animal in the screening method and blood sugar level of the test animal increases by at least about 10%, preferably at least 30%, more preferably at least about 50%, the test compound can be selected to be a compound having a therapeutic/preventive effect on the diseases described above.

The compound obtained using the above screening method is a compound selected from the test compounds described above and exhibits a preventive/therapeutic effect on diseases caused by deficiencies, damages, etc. of the GPR40 of the present invention (e.g., diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc.), a pancreatic function regulating agent (e.g., a pancreatic function improving agent), an insulin secretagogue, a hypoglycemic agent, a pancreatic β cell protecting agent, etc. In addition, compounds derived from the compound obtained by the screening described above can be used as well.

The compound obtained by the screening method may form salts and may be used in the form of salts with physiologically acceptable acids (e.g., inorganic acids, organic acids, etc.) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The pharmaceutical comprising the compound obtained by the above screening method or salts thereof can be manufactured in a manner similar to the method for preparing the pharmaceutical comprising the GPR40 of the present invention described above.

Since the pharmaceutical preparation thus obtained is safe and low toxic, it can be administered to human or non-human mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound is orally administered to an adult (as 60 kg body weight), the compound is generally administered to the patient with diabetes mellitus in a daily dose of about 0.1 to about 100 mg, preferably about 1.0 to about 50 mg and, more preferably about 1.0 to about 20 mg. In parenteral administration, a single dose of said compound or its salt may vary depending upon target subject, target disease, etc. When the compound or its salt is administered to an adult (as 60 kg body weight) with diabetes mellitus in the form of an injectable preparation, it is advantageous to administer the compound intravenously to the patient in a daily dose of about 0.01 to about 30 mg, preferably about 0.1 to about 20 mg, and more preferably about 0.1 to about 10 mg. For other animal species, the corresponding dose as converted per 60 kg weight can be administered.

(12b) Method of Screening a Compound that Promotes or Inhibits the Activity of a Promoter to the DNA of the Present Invention The present invention provides a method of screening a compound or its salts that promote or inhibit the activity of a promoter to the DNA of the present invention, which comprises administering a test compound to a non-human mammal deficient in expression of the DNA of the present invention and detecting the expression of the reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention, which is selected from the aforesaid non-human mammals deficient in expression of the DNA of the present invention.

The same examples of the test compound apply to specific compounds used for the screening.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the GPR40 of the present invention is substituted with, e.g., β-galactosidase gene (lacZ) derived from *Escherichia coli*, β-galactosidase is expressed in a tissue where the GPR40 of the present invention should originally be expressed, instead of the GPR40 of the present invention. Thus, the expression state of the GPR40 of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the GPR40 of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method described above are compounds that are selected from the test compounds described above and that promote or inhibit the promoter activity to the DNA of the present invention.

The compound obtained by the screening method above may form salts and the same salts as described above are used as the salts of the compound.

The compound or its salt that promotes the promoter activities to the DNA of the present invention can promote expression of the GPR40 of the present invention to promote the functions of the GPR40 and is thus useful as a pharmaceutical such as a preventive/therapeutic agent for, e.g., diseases associated with dysfunction of the GPR40 of the present invention, or as a drug such as a pancreatic function regulating agent (e.g., a pancreatic function improving agent), an insulin secretagogue, a hypoglycemic agent, a pancreatic β cell protecting agent, etc.

The compound or its salt that inhibits the promoter activities to the DNA of the present invention can inhibit expression of the GPR40 of the present invention to inhibit the functions of the GPR40 and is thus useful as a pharmaceutical such as a preventive/therapeutic agent for, e.g., diseases caused by overexpression of the GPR40 of the present invention, or as a drug such as a pancreatic function regulating agent (e.g., a pancreatic function improving agent), an insulin secretion suppressing agent, a hyperglycemic agent, etc.

The diseases associated with dysfunction of the GPR40 of the present invention include diabetes mellitus, impaired glucose tolerance, ketosis, acidosis, diabetic neuropathy, diabetic nephropathy, diabetic retinopathy, hyperlipemia, sexual dysfunction, skin disorders, arthritis, osteopenia, arteriosclerosis, thrombotic disorders, dyspepsia, deficits in memory, etc. Diabetes mellitus includes insulin dependent (type I) diabetes mellitus, insulin non-dependent (type II) diabetes mellitus, etc.

The diseases caused by overexpression of the GPR40 of the present invention include, for example, obesity, hyperlipemia, type II diabetes mellitus, hypoglycemia, hypertension, diabetic neuropathy, diabetic nephropathy, diabetic retinopathy, edema, insulin resistant syndrome, unstable diabetes, fatty atrophy, insulin allergy, insulinoma, arteriosclerosis, thrombotic disorders, lipotoxicity, cancer, etc.

In addition, compounds derived from the compound obtained by the screening described above can be used as well.

The pharmaceutical comprising the compound obtained by the above screening method or salts thereof can be manufactured in a manner similar to the method for preparing the pharmaceutical comprising the compound of changing the binding properties of the GPR40 of the present invention or its salt to the ligand described above.

Since the pharmaceutical preparation thus obtained is safe and low toxic, it can be administered to, for example, human or non-human mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound is orally administered to an adult (as 60 kg body weight), the compound is generally administered to the patient with diabetes mellitus in a daily dose of about 0.1 to about 100 mg, preferably about 1.0 to about 50 mg and, more preferably about 1.0 to about 20 mg. In parenteral administration, a single dose of said compound or its salt may vary depending upon target subject, target disease, etc. When the compound or its salt is administered to an adult (as 60 kg body weight) with diabetes mellitus in the form of an injectable preparation, it is advantageous to administer the compound intravenously to the patient in a daily dose of about 0.01 to about 30 mg, preferably about 0.1 to about 20 mg, and more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that promotes or inhibits the promoter activities to the DNA of the present invention and can greatly contribute to elucidation of causes for various diseases suspected of deficiency in expression of the DNA of the present invention and for the development of preventive/therapeutic drug for these diseases.

Also, a so-called transgenic animal (gene transferred animal) can be prepared by using a DNA containing the promoter region of the GPR40 of the present invention, ligating genes encoding various proteins at the downstream and injecting the same into oocyte of an animal. It is thus possible to synthesize the GPR40 therein specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the GPR40 of the present invention itself.

In the specification and drawings, the codes of bases, amino acids, etc. are denoted in accordance with the IUPAC-IUB Commission on Biochemical Nomenclature or by the common codes in the art, examples of which are shown below. For amino acids that may have the optical isomer, L form is presented unless otherwise indicated.

| | | |
|---|---|---|
| DNA | deoxyribonucleic acid | |
| cDNA | complementary deoxyribonucleic acid | |
| A | adenine | |
| T | thymine | |
| G | guanine | |
| C | cytosine | |
| U | uracyl | |
| RNA | ribonucleic acid | |
| mRNA | messenger ribonucleic acid | |
| dATP | deoxyadenosine triphosphate | |
| dTTP | deoxythymidine triphosphate | |
| dGTP | deoxyguanosine triphosphate | |
| dCTP | deoxycytidine triphosphate | |
| ATP | adenosine triphosphate | |
| EDTA | ethylenediaminetetraacetic acid | |
| SDS | sodium dodecyl sulfate | |
| Gly | glycine | |
| Ala | alanine | |
| Val | valine | |
| Leu | leucine | |
| Ile | isoleucine | |
| Ser | serine | |
| Thr | threonine | |
| Cys | cysteine | |
| Met | methionine | |
| Glu | glutamic acid | |
| Asp | aspartic acid | |
| Lys | lysine | |
| Arg | arginine | |
| His | histidine | |
| Phe | phenylalanine | |
| Tyr | tyrosine | |
| Trp | tryptophan | |
| Pro | proline | |
| Asn | asparagine | |
| Gln | glutamine | |
| pGlu | pyroglutamic acid | |
| * | corresponding to termination codon | |
| Me | methyl group | |
| Et | ethyl group | |
| Bu | butyl group | |
| Ph | phenyl group | |
| TC | thiazolidine-4(R)-carboxamido group | |

Substituents, protecting groups and reagents generally used in this specification are presented as the codes below.

| | |
|---|---|
| Tos | p-toluenesulfonyl |
| CHO | formyl |
| Bzl | benzyl |
| $Cl_2$-Bzl | 2,6-dichlorobenzyl |
| Bom | benzyloxymethyl |
| Z | benzyloxycarbonyl |
| Cl—Z | 2-chlorobenzyloxycarbonyl |
| Br—Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dicyclohexylcarbodiimide |

The sequence identification numbers in the sequence listing of the specification indicates the following sequence, respectively.

SEQ ID NO: 1
This shows the amino acid sequence of mouse spleen-derived GPR40 of the present invention.

SEQ ID NO: 2
This shows the base sequence of cDNA encoding mouse spleen-derived GPR40 of the present invention.

SEQ ID NO: 3
This shows the amino acid sequence of rat spleen-derived GPR40 of the present invention.

SEQ ID NO: 4
This shows the base sequence of cDNA encoding rat spleen-derived GPR40 of the present invention.

SEQ ID NO: 5
This shows the amino acid sequence of human-derived GPR40 of the present invention.

SEQ ID NO: 6.
This shows the base sequence of cDNA encoding human-derived GPR40 of the present invention.

SEQ ID NO: 7
This shows the base sequence of primer 1 used for PCR in EXAMPLE 2 below.

SEQ ID NO: 8
This shows the base sequence of primer 2 used for PCR in EXAMPLE 2 below.

SEQ ID NO: 9
This shows the base sequence of primer 3 used for PCR in EXAMPLE 3 below.

SEQ ID NO: 10
This shows the base sequence of primer 4 used for PCR in EXAMPLE 4 below.

SEQ ID NO: 11
This shows the base sequence of the primer used for TaqMan PCR in EXAMPLE 4 below.

SEQ ID NO: 12
This shows the base sequence of the probe sed for TaqMan PCR in EXAMPLE 4 below.

SEQ ID NO: 13
This shows the base sequence of the primer used for TaqMan PCR in EXAMPLE 4 below.

SEQ ID NO: 14
This shows the base sequence of the primer used for TaqMan PCR in EXAMPLE 4 below.

SEQ ID NO: 15
This shows the base sequence of the probe used for TaqMan PCR in EXAMPLE 4 below.

SEQ ID NO: 16
This shows the base sequence of the primer used for TaqMan PCR in EXAMPLE 4 below.

SEQ ID NO: 17
This shows the amino acid sequence of cynomolgus monkey-derived GPR40 of the present invention.

SEQ ID NO: 18
This shows the base sequence of cDNA encoding cynomolgus monkey-derived GPR40 of the present invention.

SEQ ID NO: 19
This shows the base sequence of the primer used for PCR in EXAMPLE 5 below.

SEQ ID NO: 20
This shows the base sequence of the primer used for PCR in EXAMPLE 5 below.

SEQ ID NO: 21
This shows the base sequence of the probe used for PCR in EXAMPLE 5 below.

SEQ ID NO: 22
This shows the base sequence of the primer used for PCR in EXAMPLE 5 below.

SEQ ID NO: 23
This shows the base sequence of the primer used for PCR in EXAMPLE 7 below.

SEQ ID NO: 24
This shows the base sequence of the primer used for PCR in EXAMPLE 7 below.

SEQ ID NO: 25
This shows the base sequence of the probe used for PCR in EXAMPLE 7 below.

SEQ ID NO: 26
This shows the base sequence of the primer used for PCR in EXAMPLE 8 below.

SEQ ID NO: 27
This shows the base sequence of the probe used for PCR in EXAMPLE 8 below.

SEQ ID NO: 28
This shows the base sequence of the primer used for PCR in EXAMPLE 9 below.

SEQ ID NO: 29
This shows the amino acid sequence of hamster-derived GPR40 of the present invention.

SEQ ID NO: 30
This shows the base sequence of cDNA encoding hamster-derived GPR40 of the present invention.

SEQ ID NO: 31
This shows the base sequence of primer 1 used for PCR in EXAMPLE 9 below.

SEQ ID NO: 32
This shows the base sequence of primer 2 used for PCR in EXAMPLE 9 below.

SEQ ID NO: 33
This shows the amino acid sequence of the C-terminal peptide of human-derived GPR40 of the present invention.

SEQ ID NO: 34
This shows the base sequence of the sense strand of siRNA m40i103.

SEQ ID NO: 35
This shows the base sequence of the antisense strand of siRNA m40i103.

SEQ ID NO: 36
This shows the base sequence of the sense strand of siRNA m40i256.

SEQ ID NO: 37
This shows the base sequence of the antisense strand of siRNA m40i103.

SEQ ID NO: 38
This shows the base sequence of the primer used for PCR in EXAMPLE 20 below.

SEQ ID NO: 39
This shows the base sequence of the primer used for PCR in EXAMPLE 20 below.

SEQ ID NO: 40
This shows the base sequence of the sense strand primer used for PCR in REFERENCE EXAMPLE 1 below.

SEQ ID NO: 41
This shows the base sequence of the antisense strand primer used for PCR in REFERENCE EXAMPLE 1 below.

The transformant, *Escherichia coli* TOP10/Zero Blunt-mGPR40 obtained in EXAMPLE 2 later described has been on deposit since Mar. 18, 2002 under the Accession Number FERM BP-7967 at the National Institute of Advanced Industrial Science and Technology, International Patent Organism Depositary, located at Central 6, 1-1-1 Higashi, Tsukuba, Ibaraki, Japan (postal code 305-8566), and since Feb. 14, 2002 has been on deposit at the Institute for Fermentation (IFO), located at 2-17-85, Juso-honmachi, Yodogawa-ku, Osaka-shi, Osaka, Japan (postal code 532-8686) under the Accession Number IFO 16762.

The transformant, *Escherichia coli* JM109/pCR2.1-rGPR40 obtained in EXAMPLE 3 later described has been on deposit since Mar. 18, 2002 under the Accession Number FERM BP-7968 at the National Institute of Advanced Industrial Science and Technology, International Patent Organism Depositary, and since Feb. 14, 2002 has been on deposit at the Institute for Fermentation (IFO), under the Accession Number IFO 16763.

The transformant, *Escherichia coli* JM109/pCR2.1-monkey GPR40 obtained in EXAMPLE 5 later described has been on deposit since Jul. 23, 2002 under the Accession Number FERM BP-8125 at the National Institute of Advanced Industrial Science and Technology, International Patent Organism Depositary.

The transformant, *Escherichia coli* JM109/pTA hamster GPR40 obtained in EXAMPLE 9 later described has been on deposit as the transformant, *Escherichia coli* JM109/pTA hamster GPR40 since Dec. 11, 2002 under the Accession Number FERM BP-8258 at the National Institute of Advanced Industrial Science and Technology, International Patent Organism Depositary.

The transformant, *Escherichia coli* DH5α/pGT-GPR40 obtained in EXAMPLE 21 later described has been on deposit since Dec. 11, 2002 under the Accession Number FERM BP-8259 at the National Institute of Advanced Industrial Science and Technology, International Patent Organism Depositary.

EXAMPLES

The present invention is described in more detail below with reference to REFERENCE EXAMPLES and EXAMPLES, but is not deemed to limit the scope of the present invention thereto. The genetic manipulation using *Escherichia coli* were performed according to the methods described in the Molecular Cloning.

Reference Example 1

Construction of Human GPR40 Expression Vector

The DNA fragment encoding human GPR40 was acquired by the following PCR procedures. That is, using 20 pmols each of oligo DNA (SEQ ID NO: 40) shown by 5'>CGTC-GACCCGGCGGCCCCATGGACCTGCCCCCG<3' as a sense strand primer and oligo DNA (SEQ ID NO: 41) shown by 5'>CATCGATTAGCAGTGGCGTTACTTCTGG-GACTT<3' as an antisense strand primer, 50 μl of a solution mixture containing 5 μl of 10× Advantage (registered trademark) 2 PCR Buffer (CLONTECH), 1 μl of 50×dNTP mix (CLONTECH), 1 μl of 50× Advantage 2 Polymerase Mix (CLONTECH) and 1 μl of human pancreatic cDNA solution (CLONTECH) as a template DNA was prepared. The reaction was carried out on a thermal cycler (GeneAmp (registered trademark) PCR System model 9700 (Applied Biosystems)), with a program by reacting at 96° C. for 1 minute and then by repeating the following cycle 35 times, one cycle set to include 96° C. for 30 seconds, 61° C. for 30 seconds, and 72° C. for 120 seconds and finally by extension at 72° C. for 10 minutes. After completion of the reaction, the reaction solution was electrophoresed on agarose gel to give a single product. The product was cloned using TA Cloning Kit (Invitrogen) to confirm the gene sequence. A clone free from PCR error was subjected to double digestion with restriction enzymes SalI (Takara Shuzo) and ClaI (Takara Shuzo), the digestion product was electrophoresed on agarose gel to excise the single product. The resulting fragment (ca. 1 kb) was introduced into vector pAKKO-111, which was used for transfection of CHO cells.

Example 1

Confirmation of the Reactivity of Fatty Acid with Human-Derived GPR40

The CHO-K1 cell line was cultured in HAM F-12 medium (Invitrogen) containing 10% fetal calf serum (Invitrogen), unless otherwise indicated. One day before transfection, $4.5 \times 10^5$ cells per 10 cm$^2$ were plated, followed by incubation in a $CO_2$ incubator adjusted to a concentration of 5% $CO_2$ at 37° C. for at least 15 hours. Using Lipofectamine reagent (Invitrogen), transfection procedures were carried out by modifications of the method attached to the reagent. When a 6-well plate was used for the incubator, the following procedures were performed. First, 2 tubes each having a 1.5 ml volume were prepared and 100 μl each of Opti-MEM-I medium (Invitrogen) was dispensed in each tube. Next, 1 μg of the expression vector was charged in one tube and in another tube, 6 μl of Lipofectamine reagent was charged, which were mixed together. The mixture was settled for 20 minutes at room temperature. To the solution, 800 μl of Opti-MEM-I medium was added and the resulting solution mixture for transfection was added to CHO-K1 cells, which had been previously washed with Opti-MEM-I medium. Then, the cells were incubated in a $CO_2$ incubator for 6 hours. After the incubation, the cells were rinsed with PBS (Invitrogen), then scraped using 0.05% trypsin-EDTA solution (Invitrogen) and recovered by centrifugal operation. The cells obtained were counted and diluted to $5 \times 10^4$ cells per 200 μl of the medium. The dilution was dispensed onto a Black walled 96-well plate (Costar) in 200 μl each per well, followed by incubation overnight in a $CO_2$ incubator. Various test samples were added to the CHO-K1 cells in which the receptor was transiently expressed by the transfection operation described above, whereby changes in the intracellular calcium ion level were determined using FLIPR (Molecular Device). In order to determine the changes in the intracellular calcium ion level on FLIPR, the cells were pre-treated by the following procedures. First, for the purpose of adding a fluorescent dye Fluo-3 AM (DOJIN) to the cells or washing the cells immediately before the FLIPR assay, an assay buffer was prepared. A solution obtained by adding 20 ml of 1M HEPES (pH 7.4) (DOJIN) to 1000 ml of HBSS (Invitrogen) was prepared (hereinafter HBSS/HEPES solution), to which 10 ml of a solution mixture obtained by dissolving 710 mg of Probenecid (Sigma) in 5 ml of 1N NaOH and further adding 5 ml of HBSS/HEPES solution was added. The resulting solution was used as the assay buffer. Next, 50 μg of Fluo-3AM was dissolved in 21 μl of DMSO (DOJIN) and an equal volume of 20% Pulronic acid (Molecular Probes) was added to and mixed with the solution. The mixture was then added to 10.6 ml of the assay buffer supplemented with 105 μl of fetal calf serum to prepare a fluorescent dye solution. The medium for the transfection-treated CHO-K1 cells was removed. Immediately thereafter, the fluorescent dye solution was dispensed in 100 μl each/well and the cells were incubated in a $CO_2$ incubator for an hour so that the fluorescent dye was taken up into the cells. The cells after the incubation was washed with the assay buffer described above and set on FLIPR. A test sample added to the receptor-expressed CHO-K1 cells was prepared using the assay buffer and set on FLIPR at the same time. After various test samples were added thereto.

Following the pre-treatment above, changes in intracellular calcium level after addition of various test samples were measured on FLIPR. The results revealed that the CHO-K1 cells expressing the GPR40 receptor were specifically responsive (increase in intracellular calcium level), when farnesoic acid, 5.8.11-eicosatriynoic acid, 5.8.11.14-eicosatetraynoic acid, oleic acid, linoleic acid, linolenic acid, arachidonic acid, eicosapentaenoic acid (EPA), eicosadienoic acid, eicosatrienoic acid, docosahexaenoic acid (DHA), docosatrienoic acid, adrenic acid, lauric acid, etc. were added in $10^{-5}$ M to $10^{-6}$ M [FIGS. 1 to 13]. With the CHO-K1 cells into which the expression vector alone for control was introduced, such response was not observed. That is, it became clear that the endogenous ligand for GPR40 was a fatty acid.

Example 2

Cloning of cDNA Encoding Mouse Spleen-Derived GPR40 and Determination of its Base Sequence Using as a template mouse spleen cDNA (Marathon-Ready™ cDNA; Clontech, Inc.), PCR was carried out using two primers, i.e., primer 1 (SEQ ID NO: 7) and primer 2 (SEQ ID NO: 8). Pyrobest DNA polymerase (Takara Shuzo) was used for PCR, followed by (1) reacting at 98° C. for 1 minute, (2) repeating the reaction at 98° C. for 10 seconds, 55° C. for 30 seconds and 72° C. for 60 seconds 40 times, and (3) extension at 72° C. for 2 minutes. After the reaction, the amplified product was cloned to a plasmid vector, pCR-Blunt (Invitrogen, Inc.) in accordance with the protocol of Zero Blunt PCR Cloning Kit (Invitrogen, Inc.). The vector was transfected to *Escherichia coli* TOP10 (Invitrogen, Inc.) and the plasmid-bearing clones were selected in LB agar medium containing kanamycine. Analysis of the individual clones on base sequences gave the cDNA sequence (SEQ ID NO: 2) encoding a novel G protein-coupled receptor protein. A novel protein containing the amino acid sequence (SEQ ID NO: 1) deduced from this cDNA was named mGPR40. Also, the transformant was named *Escherichia coli* TOP10/Zero Blunt-mGPR40.

Example 3

Cloning of cDNA Encoding Rat Spleen-Derived GPR40 and Determination of its Base Sequence Using as a template rat spleen cDNA (Marathon-Ready™ cDNA; Clontech, Inc.), PCR was carried out using two primers, i.e., primer 3 (SEQ ID NO: 9) and primer 4 (SEQ ID NO: 10). Advantage 2 Polymerase mix (Clontech) was used for PCR, followed by (1) reacting at 96° C. for 1 minute, (2) repeating the reaction at 96° C. for 10 seconds and 72° C. for 2 minutes 5 times, (3) repeating at 96° C. for 10 seconds and 70° C. for 2 minutes 25 times, and then extension at 72° C. for 5 minutes. After the reaction, the amplified product was cloned to a plasmid vector, pCR2.1TOPO (Invitrogen, Inc.) in accordance with the protocol of TOPO TA Cloning Kit (Invitrogen, Inc.). The vector was transfected to *Escherichia coli* JM109 (Takara Shuzo) and the plasmid-bearing clones were selected in LB agar medium containing ampicillin. Analysis of the individual clones on base sequences gave the cDNA sequence (SEQ ID NO: 4) encoding a novel G protein-coupled receptor protein. A novel protein containing the amino acid sequence (SEQ ID NO: 3) deduced from this cDNA was named rGPR40. Also, the transformant was named *Escherichia coli* JM109/pCR2.1-rGPR40.

Example 4

Distribution of Expression (1) Cells and Medium

NIH-3T3 and B104 cells were purchased from ATCC. The mouse spleen β cell line described in the literature (Jun-ichi Miyazaki, et al., Endocrinology, Vol. 127, No. 1, p126–132) was used. The respective cells were incubated in 10% FCS-containing DMEM medium (Invitrogen, Inc.) to a preconfluent stage.

(2) Extraction of RNA and Synthesis of cDNA

The cDNA used for expression distribution in human and mouse tissues was subjected to reverse transcription from 1 µg of polyA+ RNA (Clontech, Inc.) derived from various tissues in human and mouse using random primers. Reverse transcriptase SuperScriptII (GIBCO BRL, Inc.) was used, reacted following the attached protocol, precipitated in ethanol and dissolved in 100 µl of TE.

In the mouse cell-derived cDNA, the cells were scraped in Trypsin-EDTA and the cell number was counted. The total RNA was extracted and purified following the manual for RNeasy mini KIT (QIAGEN, Inc.). After first strand cDNA was synthesized using random in accordance with the manual for SuperScript II (Invitrogen, Inc.), 1 µg of the extracted RNA was precipitated in ethanol and dissolved in 100 µl of TE.

(3) Quantification Using TaqMan

The tissue-derived cDNA (corresponding to 5 ng of RNA) and the cell line-derived cDNA (corresponding to 25 ng of RNA) were made 15 µl in total solution volume, using amplification reagent TaqMan (trade name), Universal PCR Master Mix (Applied Biosystems Japan K.K.), TaqMan for GPR40 detection (trade name) Probe Kit (sequences: 11 through 16, Applied Biosystems Japan K.K.), followed by reacting them. The final concentrations of the respective primers and probes were in accordance with the manual.

TaqMan (trademark) PCR was carried out on ABI PRISM (trademark) 7900HT sequence detection system (Applied Biosystems Japan K. K.). The temperature cycle used was complied with the manual of TaqMan (trademark) Universal PCR Master Mix (Applied Biosystems Japan K. K.).

Quantitative TaqMan analysis of the amplification product was performed using 7900HT SDS software (Applied Biosystems Japan K. K.). The calibration curve used to count the copy number was prepared from $C_T$ values in six logarithms from $10^7$ copies/well to $10^2$ copies/well using cDNA fragment (human GPR40) or Plasmid DNA (mouse GPR40) of known concentrations, including the full length amplification region.

Figure 14:
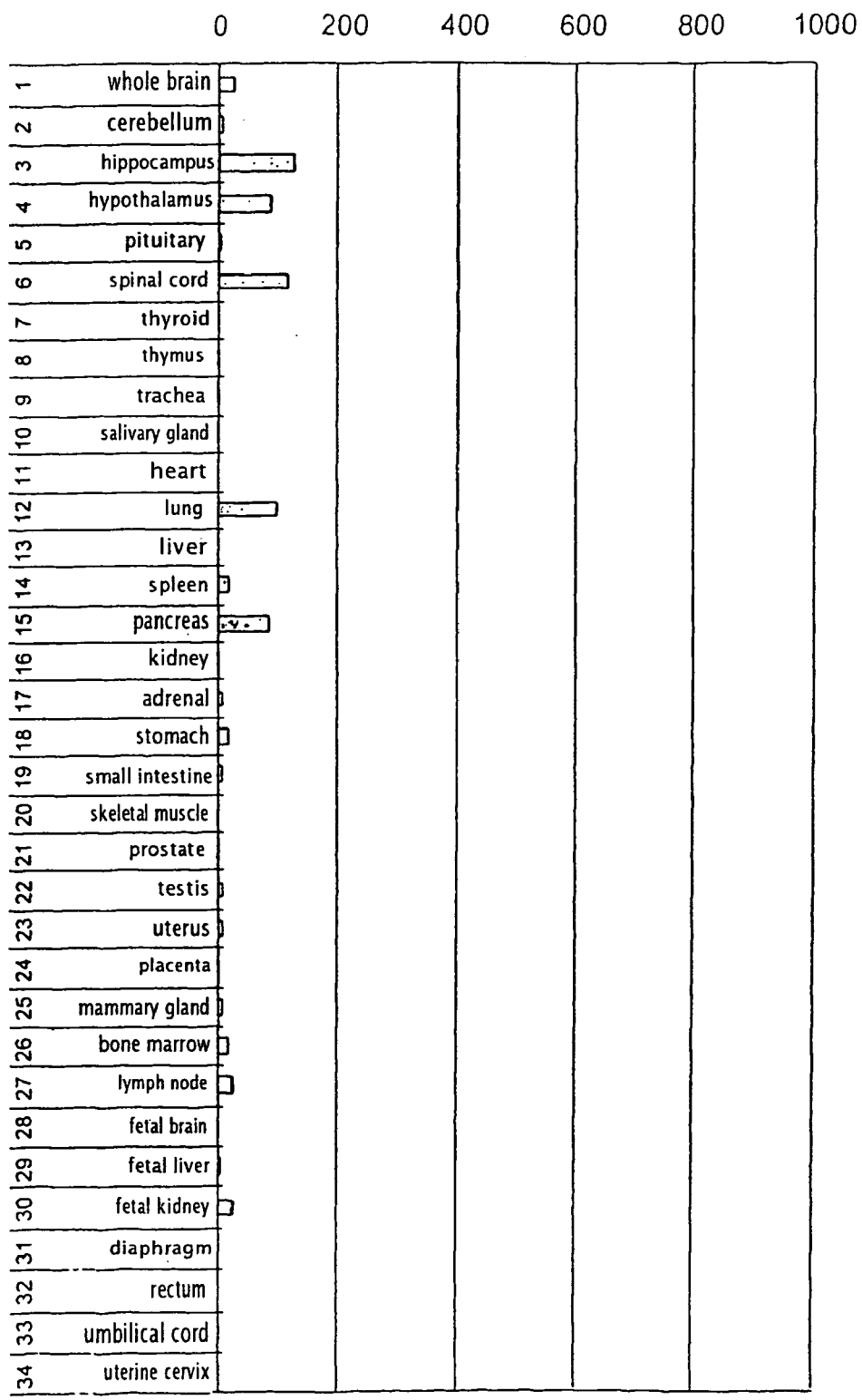
FIG. 14 shows expression distribution of GPR40 mRNA in various human tissues. The abscissa designates the number of copies per poly(A)$^+$ RNA (ng).
Figure 15:
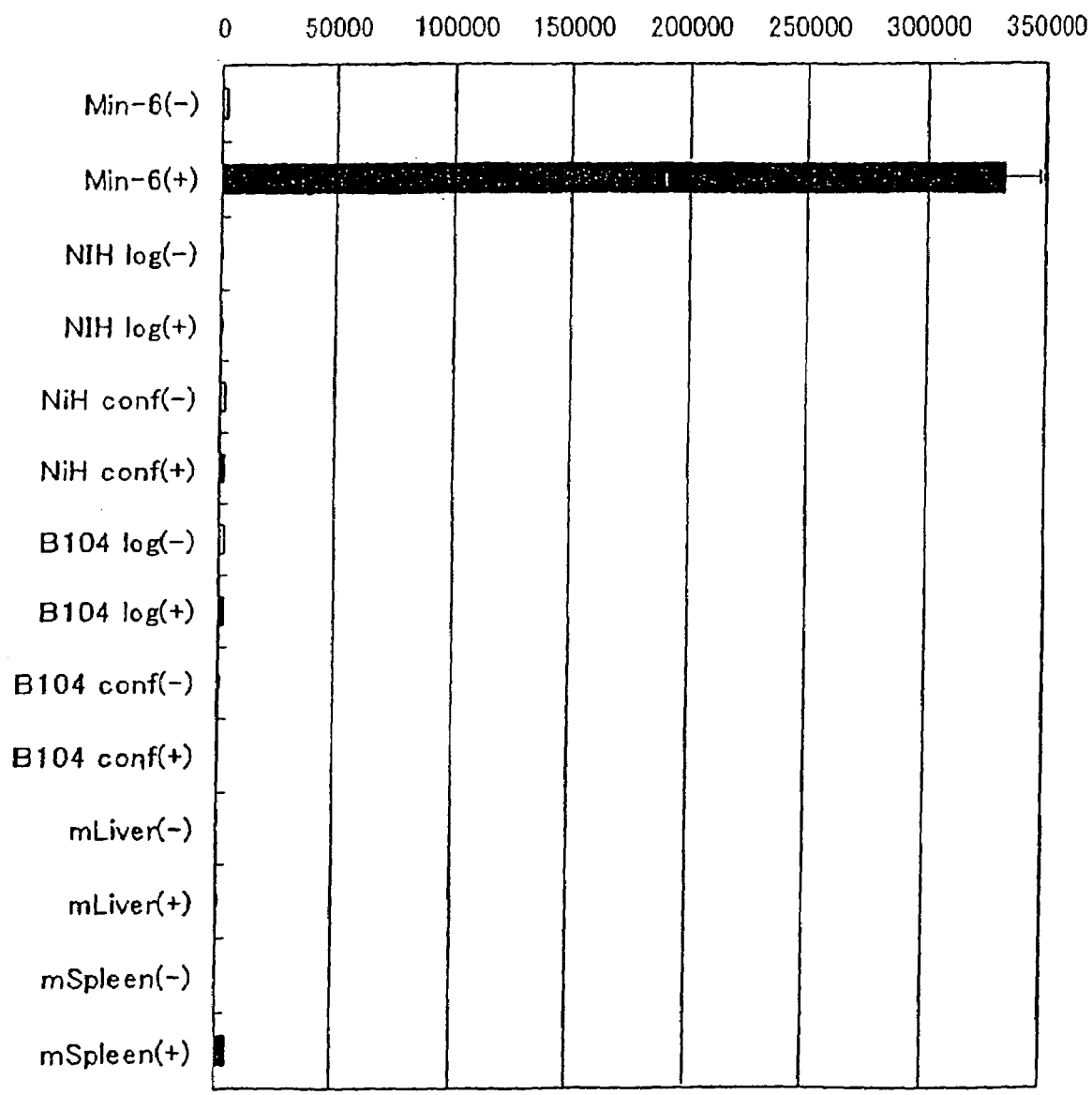
FIG. 15 shows expression distribution of GPR40 mRNA in various mouse tissues, wherein Min-6, NIH log, NiH conf, B104 log, B104 conf, mLiver and mSpleen denote MIN6 cells, the logarithmic growth phase of NIH/3T3, the stationary phase of NIH/3T3, the logarithmic growth phase of NIH/3T3 transformed with neu oncogene, the stationary phase of NIH/3T3 transformed with neu oncogene, mouse liver and mouse spleen, respectively. The abscissa designates the number of copies per total RNA (25 ng), wherein (+) and (−) denote the addition with reverse transcriptase and no reverse transcriptase addition, respectively.

The expression distribution of GPR40 mRNA various human tissues is shown in FIG. 14 and the expression distribution of GPR40 mRNA various mouse cells in FIG. 15. In human tissues, relatively high expression was observed in the pancreas, lung, hippocampus, hypothalamus and bone marrow. In mouse, extremely high expression was observed in pancreatic cancer-derived cells.

Example 5

Cloning of cDNA Encoding Cynomolgus Monkey-Derived GPR40 and Determination of its Base Sequence Using cynomolgus monkey DNA as a template, PCR was carried out using primer (SEQ ID NO: 19) and primer 2 (SEQ ID NO: 20). For PCR, Pyrobest DNA Polymerase (TAKARA) was used, followed by (1) reacting 40 times at 95° C. for 1 minute, (2) repeating the reaction at 95° C. for 10 seconds, 58° C. for 20 seconds and 72° C. for 1 minute and 30 seconds, and then extension at 72° C. for 7 minutes. After the reaction, the amplified product was diluted to 1/50. Using the dilution as a template, nested PCR was carried out using primer (SEQ ID NO: 21) and primer 2 (SEQ ID NO: 22). After the reaction, the amplification product was cloned to a plasmid vector, pCR2.1TOPO (Invitrogen, Inc.) in accordance with the protocol of TOPO TA Cloning Kit (Invitrogen, Inc.). The plasmid was transfected to *Escherichia coli* JM109 (Takara Shuzo) and the plasmid-bearing clones were selected in LB agar medium containing ampicillin. Analysis of the individual clones on base sequences gave the cDNA sequence (SEQ ID NO: 18) encoding a novel G protein-coupled receptor protein. A novel protein containing the amino acid sequence (SEQ ID NO: 17) deduced from this cDNA was named monkey GPR40. Also, the transformant was named *Escherichia coli* JM109/pCR2.1-monkey GPR40.

91

Example 6

Figure 16:
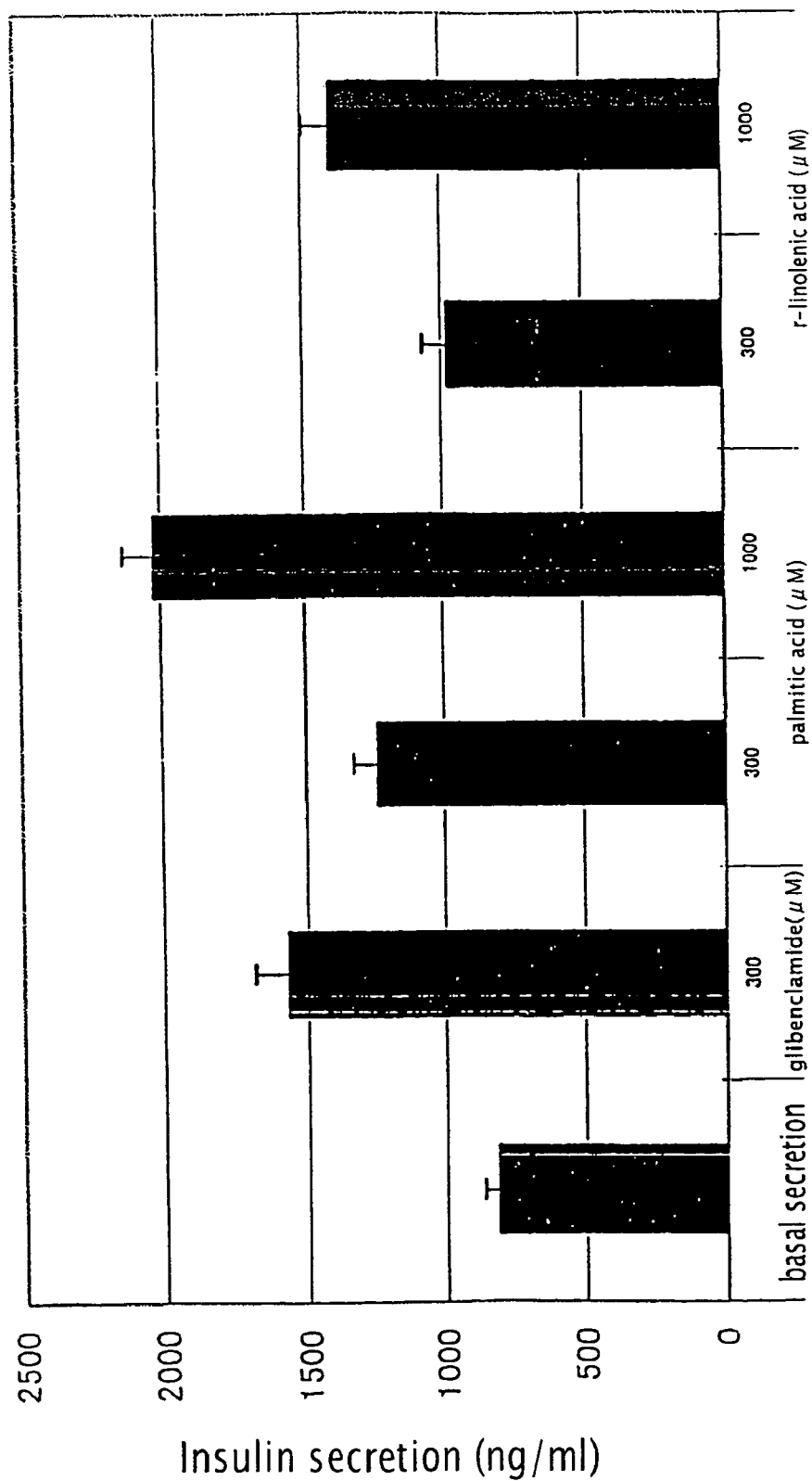
FIG. 16 shows the results of changes in insulin secretion examined when MIN6 cells were stimulated for 90 minutes with palmitic acid, γ-linoleic acid or glibenclamide for positive control. The abscissa designates the compound added and its concentration (μM). The ordinate designates the secreted insulin level (ng/ml).
Figure 17:
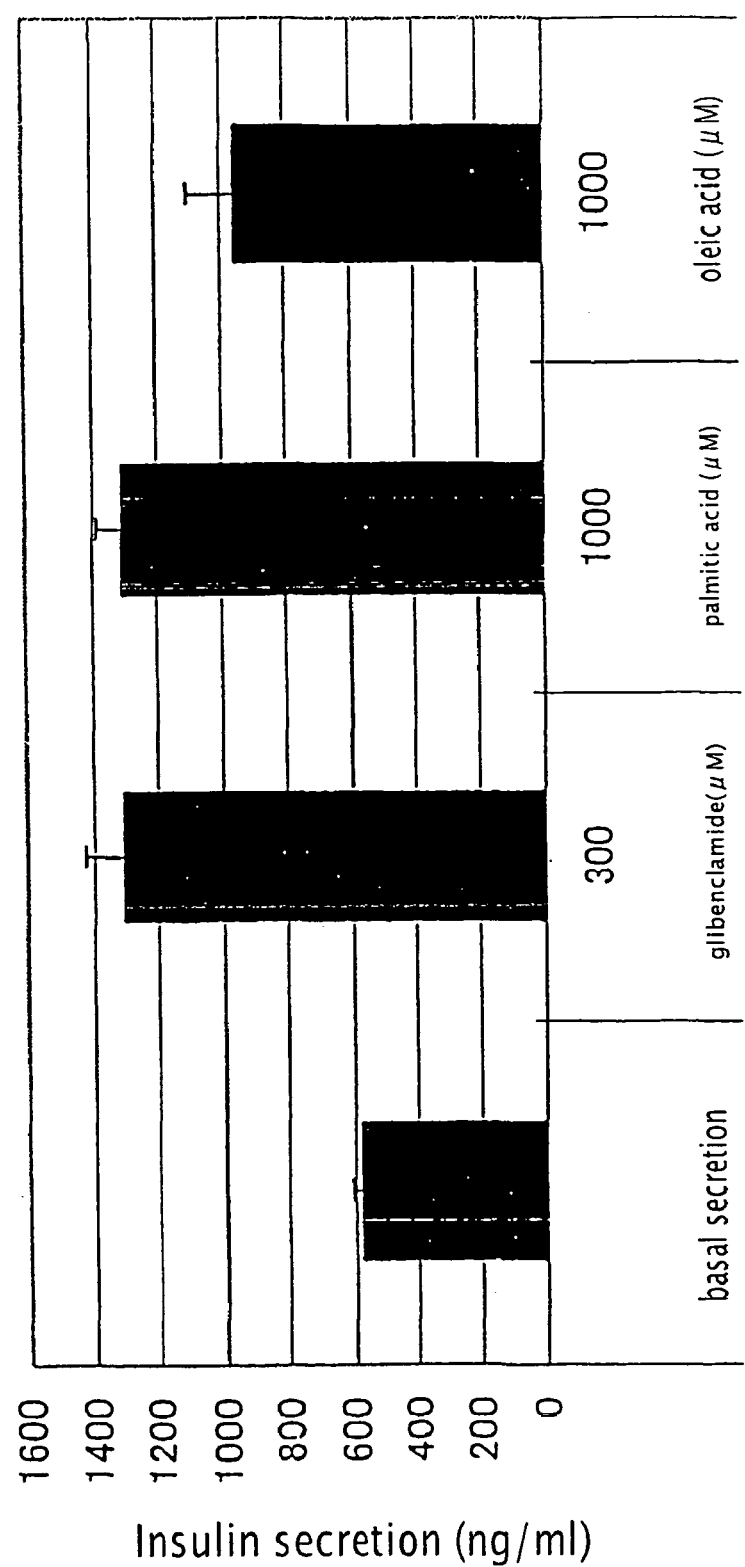
FIG. 17 shows the results of changes in insulin secretion examined when MIN6 cells were stimulated for 60 minutes with palmitic acid, oleic acid or glibenclamide for positive control. The abscissa designates the compound added and its concentration (μM). The ordinate designates the secreted insulin level (ng/ml).

Insulin Secretion Promoting Action of Free Fatty Acids in Mouse Insulinoma MIN6 Cells The MIN6 cells were cultured in DMEM (high glucose, Invitrogen) containing 15% FCS (Trace Scientific Ltd.), 55 μM 2-mercaptoethanol, 100 U/ml penicillin and 100 μg/ml streptomycin, unless otherwise indicated. MIN6 cells were plated in a 96-well plate in $10^5$ cells/well, followed by incubation at 37° C. for 3 days in a $CO_2$ incubator adjusted to a concentration of 5% $CO_2$. The medium was replaced by RPMI1640 (glucose free, Invitrogen) containing 10% FCS (Trace Scientific Ltd.), 5.5 mM glucose, 100 U/ml penicillin and 100 μg/ml streptomycin, followed by incubation for further 24 hours. After the medium was removed by suction, a solution mixture of free fatty acid-bovine serum albumin (BSA) (in a molar ratio of 4:1) diluted with RPMI1640 (glucose free, Invitrogen) containing 10% FCS (Trace Scientific Ltd.), 11 mM glucose, 100 U/ml penicillin and 100 μg/ml streptomycin was added to the cells, followed by reacting in a $CO_2$ incubator adjusted to a 5% $CO_2$ concentration at 37° C. for 90 minutes (or 60 minutes). After the reaction, the 96-well plate was centrifuged at 1500 rpm for 5 minutes and the culture supernatant was then recovered. The amount of insulin secreted into the culture supernatant was determined by radioimmunoassay (RIA) using the rat insulin RIA system (Amersham Pharmacia). The results revealed that insulin secretion by MIN6 cells was promoted when free fatty acids such as palmitic acid (FIG. 16, FIG. 17), γ-linolenic acid (FIG. 16), oleic acid (FIG. 17), etc. were added in 300 μM to 1000 μM. That is, it became clear that free fatty acids had the action of promoting insulin secretion in mouse insulinoma MIN6 cells. Since MIN6 cells abundantly expressed GPR40 specifically as described in EXAMPLE 4 (FIG. 15), it is assessed that the fatty acids added promoted insulin secretion via GPR40.

Example 7

Expression of GPR40 in Rat Pancreatic Langerhans Islets

Isolation of Langerhans islets from the pancreas of rat was performed by the following procedures. Wistar rat (male, 8 weeks old) was decapitated and after blood drawing, underwent a laparotomy with scissors. The common bile duct was ligated with cramps at the duodenal exit. Next, a hole was made at the liver side of the common bile duct with a syringe needle and a cannula was inserted. Through the cannula, 5 ml of 1 mg/ml collagenase XI (Sigma, C-7657) solution, which had been previously dissolved in HBSS and ice-cooled, was infused. The pancreas was excised out of the other tissues and shaken on a water bath at 37° C. for 3 minutes. HBSS (10 ml) was added thereto and after pipetting 5 or 6 times, 10 ml of HBSS was further added followed by pipetting twice. Then, 20 ml of HBSS was added and the mixture was settled for 4 minutes. The supernatant was discarded and 10 ml of HBSS was again added followed by pipetting twice. Furthermore, 10 ml of HBSS was added. After pipetting twice, 20 ml of HBSS was added and the mixture was settled for 3 minutes. The supernatant was discarded and an adequate amount of HBSS was added thereto for suspension. The suspension was transferred to a Petri dish with the black-painted bottom. RPMI1640 (glucose free, Invitrogen) containing 10% FCS (Trace Scientific Ltd.), 5.5 mM glucose, 100 U/ml penicillin and 100 μg/ml streptomycin was charged in another Petri dish and Langerhans islets selected stereomicroscopically were transferred from the Petri dish with the black-painted bottom to this Petri dish using a pipette chip.

92

Figure 18:
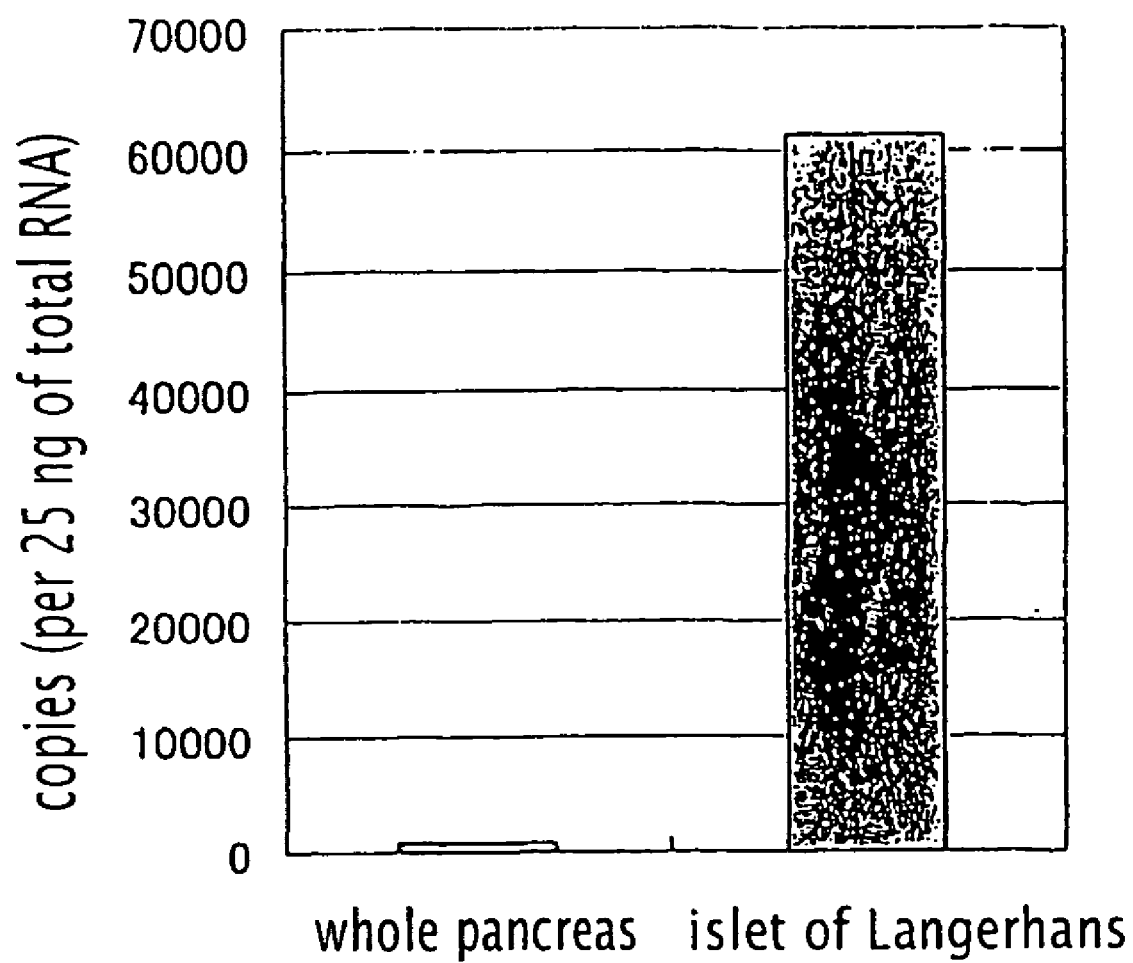
FIG. 18 shows the results of the expression level of GPR40 mRNA in rat pancreas and Langerhans islets, which was determined by RT-PCR. The result obtained in whole pancreas is represented in terms of mean value of two rats.

After the whole pancreas and the Langerhans islets obtained above were added with Isogen (Nippon Gene K. K.), the mixture was homogenized and total RNA was prepared according to the manual. Following the attached manual, the reaction was carried out at 42° C. from 1 μg of the total RNA obtained, using a random primer and SuperScriptII reverse transcriptase (GIBCO BRL, Inc.). After the reaction was completed, ethanol precipitation was performed and the precipitates were dissolved in 40 μl of distilled water. The expression level of GPR40 mRNA was quantified using Sequence Detection System Prism 7700 (ABI, Inc.). As primers for amplification and detection of the target gene, 5'-CACAGCTCTCCTTCGCTCTCTAT-3' (SEQ ID NO: 23) and 5'-CAGTTTCGCGTGGGACACT-3' (SEQ ID NO: 24) were used and as TaqMan probe, 5'-(Fam) TCAGCCTTTGCACTAGGCTTTCCATTGAAC-(Tamra)-3' (SEQ ID NO: 25) was used. For the RT-PCR solution, 0.225 μl each of the 100 μM primer solutions, 1.25 μl of 5 μM TaqMan probe and 1 μl of the cDNA solution prepared above were added to 12.5 μl of TaqMan Universal PCR Master Mix (PE Biosystems, Inc.), and distilled water was added to make the total volume of the reaction solution 25 μl. PCR was carried out by reacting at 50° C. for 2 minutes and 95° C. for 10 minutes, repeating 40 times the cycle set to include 95° C. for 15 seconds and 60° C. for 1 minute. As a result, it was confirmed that GPR40 was highly expressed in the isolated Langerhans islets (FIG. 18).

Example 8

Expression of GPR40 in the Cynomolgus Monkey Pancreatic Langerhans Islets

Isolation of Langerhans islets from the pancreas of cynomolgus monkey was performed by the following procedures. Incision with a scalpel was made at the both sides and the femoral region of cynomolgus monkey (female, weighing 3 kg). After blood drawing, animal underwent a laparotomy with scissors. The common bile duct was ligated with cramps at the duodenal exit. Next, a hole was made at the liver side of the common bile duct with a syringe needle and a cannula was inserted. Through the cannula, 25 ml of 1 mg/ml collagenase V (Sigma, C-9263) solution, which had been previously dissolved in HBSS and ice-cooled, was infused. The pancreas was excised out of the other tissues and minced with scissors to a square of about 5 mm, followed by shaking on a water bath at 37° C. for 20 minutes. After repeating the addition with several tens ml of HBSS and pipetting several times, the mixture was settled for 4 minutes and the supernatant was discarded. To the precipitate, 15 ml of 1.7 mg/ml collagenase XI (Sigma, C-7657) solution, which had previously been dissolved in HBSS, was added, followed by shaking on a water bath at 37° C. for 15 minutes. After repeating the addition with several tens ml of HBSS and pipetting several times, the mixture was settled for 3 minutes and the supernatant was discarded. An adequate amount of HBSS was added to the precipitates for dilution, and the dilution was transferred to a Petri dish with the black-painted bottom. HBSS was charged in another Petri dish and Langerhans islets selected stereomicroscopically were transferred from the Petri dish with the black-painted bottom to this Petri dish using a pipette chip.

In a manner similar to EXAMPLE 7, the total RNA was prepared from the Langerhans islets obtained above and cDNA was synthesized. The expression amount of GPR40 mRNA was determined on Sequence Detection System Prism 7700. For the amplification and detection of monkey GPR40 mRNA, 5'-GCCCGCTTCAGCCTCTCT-3' (SEQ ID NO: 26) and 5'-GAGGCAGCCCACGTAGCA-3' (SEQ ID NO: 27) were used as primers and 5'-(Fam)

Figure 19:
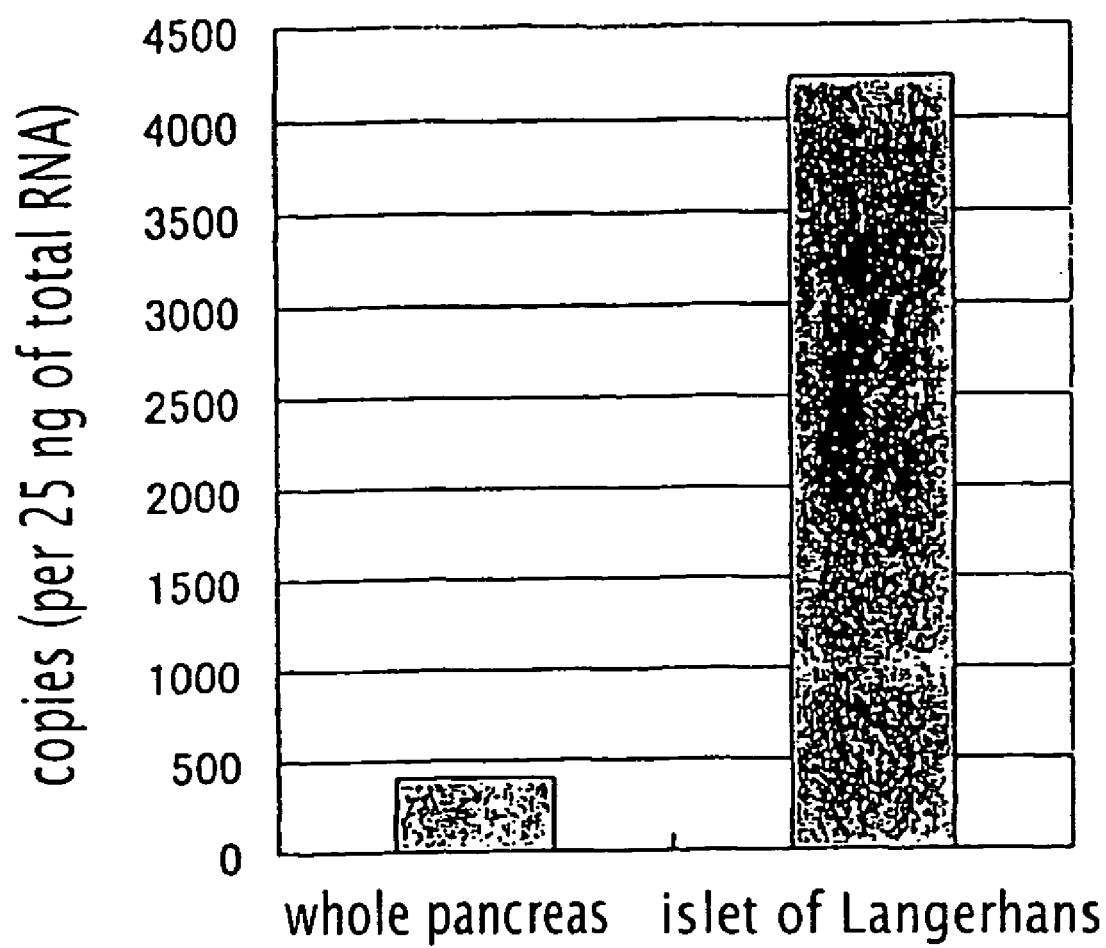
FIG. 19 shows the results of the expression level of GPR40 mRNA in cynomolgus monkey pancreas and Langerhans islets, which was determined by RT-PCR. The result obtained in whole pancreas is represented in terms of mean value of two rats.

CTGCTTTTTTTCCTGCCCTTGGCC-(Tamra)-3' (SEQ ID NO: 28) was used as TaqMan probe. As a result, it was confirmed also in the primate that GPR40 was highly expressed in the Langerhans islets (FIG. 19).

Example 9

Cloning of cDNA Encoding Hamster-Derived GPR40 and Determination of its Base Sequence Using as a template hamster cell line HIT-T15cDNA, PCR was carried out using primer 1 (SEQ ID NO: 31) and primer 2 (SEQ ID NO: 32). Klentaq DNA Polymerase (Clontech) was used for PCR, followed by (1) reacting at 95° C. for 2 minute, (2) repeating the reaction at 98° C. for 10 seconds, 63° C. for 20 seconds and 72° C. for 1 minute 35 times, and then extension at 72° C. for 7 minutes. After the reaction, the amplified product was cloned to a plasmid vector, pCR2.1TOPO (Invitrogen, Inc.) in accordance with the protocol of TOPO TA Cloning Kit (Invitrogen, Inc.). The plasmid was transfected to *Escherichia coli* JM109 (Takara Shuzo) and the plasmid-bearing clones were selected in LB agar medium containing ampicillin. Analysis of the individual clones on base sequences gave the cDNA sequence (SEQ ID NO: 30) encoding a novel G protein-coupled receptor protein. A novel protein containing the amino acid sequence (SEQ ID NO: 29) deduced from this cDNA was named hamstarGPR40. Also, the transformant was named *Escherichia coli* JM109/pTA hamstarGPR40.

Example 10

Production of Immunogen Containing the C-Terminal Peptide of Human GPR40 and Immunization A complex of the C-terminal peptide of human GPR40, Cys Ala Ala Arg Thr Gln Gly Gly Lys Ser Gln Lys (SEQ ID NO: 33; synthesized by a modification of publicly known procedures) and BSA was prepared and used as an immunogen. That is, 20 mg of BSA was dissolved in 2.0 ml of 0.1M phosphate buffer (pH 6.7). The solution was mixed with 200 µl of DMSO solution containing 2.8 mg of N-(γ-maleimidobutyryloxy) succinimide (GMBS) and the mixture was reacted at room temperature for 30 minutes. After an excess of GMBS reagent was removed through Sephadex G-25 column equilibrated with 0.1 M phosphate buffer (pH 6.5) containing 2 mM EDTA, 5 mg of maleimide-introduced BSA was mixed with 0.84 mg of the C-terminal peptide dissolved in 0.1 ml of water. The mixture was reacted overnight at 4° C. After completion of the reaction, the mixture was dialyzed to physiological saline at 4° C. for 2 days. BALB/C female mice of 8 weeks old were subcutaneously injected for immunization with about 0.05 mg/mouse of the C-terminal peptide-BSA complex, together with complete Freund's adjuvant. Two weeks after, the same dose of immunogen was boostered together with incomplete Freund's adjuvant and blood was collected a week later.

Example 11

Production of Horseradish Peroxidase (HRP)-Labeled C-Terminal Peptide

The C-terminal peptide described above (SEQ ID NO: 33) was crosslinked with HRP (for enzyme immunoassay, manufactured by Boehringer Mannheim), which was used as a labeled peptide for enzyme immunoassay (EIA). That is, 23 mg of HRP was dissolved in 2.3 ml of 0.1 M phosphate buffer, pH 6.7. The solution was mixed with 0.23 ml of DMF solution containing 1.6 mg of GMBS. After reacting for 30 minutes at room temperature, the reaction mixture was fractionated through Sephadex G-25 column equilibrated with 0.1 M phosphate buffer, pH 6.5, containing 2 mM EDTA. After 2.3 mg of the thus produced maleimide-introduced HRP was mixed with 1 mg of the C chain N-terminal peptide, the mixture was reacted at 4° C. for a day. After completion of the reaction, the mixture was fractionated through Ultrogel AcA54 (manufactured by Pharmacia) column equilibrated with 0.1 M phosphate buffer, pH 6.5 to give the HRP-labeled C-terminal peptide.

Example 12

Determination of Antibody Titer in Antisera of the C-Terminal Peptide-Immunized mouse.

The antibody titer in mouse antisera was assayed by the following method. In order to prepare an anti-mouse immunoglobulin antibody-bound microplate, first, a 0.1 ml aliquot of 0.1 M carbonate buffer solution, pH 9.6, containing 0.1 mg/ml of goat anti-mouse immunoglobulin antibody (IgG fraction, manufactured by Cappel) was dispensed onto a 96-well microplate, which was allowed to stand at 4° C. for 24 hours. Next, the plate was rinsed with phosphate buffered saline (PBS, pH 7.4). In order to block the excessive binding sites, 0.3 ml each of PBS, pH 7.2, containing 25% Block Ace (manufactured by Snow Brand Milk Products Co., Ltd.) and 0.05% $NaN_3$ was added to the plate, followed by treatment at 4° C. for at least 24 hours.

To each well of the mouse immunoglobulin antibody-bound microplate described above, 0.14 ml of mouse antiserum diluted with buffer EC [0.02 M phosphate buffer, pH 7.0, containing 0.2% BSA, 0.4 M NaCl, 0.4% Block Ace, 0.05% CHAPS [3-[(cholamidopropyl)dimethylammonio] propanesulfonic acid], 2 mM EDTA and 0.05% $NaN_3$] was added, followed by reacting at 4° C. for 16 hours. Next, after the plate was washed with PBS, pH 7.4, 0.1 ml of the HRP-labeled C-terminal peptide prepared in EXAMPLE above and diluted to 100-fold with buffer C [0.02 M phosphate buffer, pH 7.0, containing 1% BSA, 0.4 M NaCl and 2 mM EDTA] was added, followed by reacting at 4° C. for a day. Then, after the plate was washed with PBS, pH 7.4, 0.1 ml of TMB microwell peroxidase substrate system (KIRKEGAARD & PERRY LAB., dealt through Funakoshi Pharmaceutical Co., Ltd.) was added and the mixture was reacted for 20 minutes at room temperature for assay. After 0.1 ml of 1 M phosphoric acid was added to terminate the reaction, absorbance at 450 nm (Abs. 450) was measured on a plate reader (MTP-120, manufactured by Corona Co. or Multiskan Ascent manufactured by Labsystems, Inc.). An increase of the antibody titer to the C-terminal peptide was noted in all of the immunized mice.

Example 13

Production of Anti-C-Terminal Peptide Monoclonal Antibody

Mice, which showed a relatively high antibody titer in EXAMPLE 12, received final immunization by intravenously administering the C-terminal peptide-BSA in a dose of 0.08 to 0.1 mg when calculated as BSA. Three days after the final immunization, the spleen was withdrawn from mice to give the spleen cell suspension. BALB/C mouse-derived myeloma cells P3-X63.Ag 8. U1 (P3U1) were used as cells for cell fusion [Current Topics in Microbiology & Immunology, 81, 1 (1978)]. The cell fusion was carried out by a modification from the original method [Nature, 256, 495 (1975)]. That is, the spleen cells and p3U1 were washed 3 times with serum-free medium, respectively, and mixed to be 6.6:1 in a ratio of the spleen cells to P3U1 count. The cells were precipitated by centrifugation at 750 rpm for 15 minutes. After the supernatant was thoroughly removed, the precipitates were gently loosened and 0.3 ml of 45% polyethylene glycol (PEG) 6000 (manufactured by Kochlight, Inc.). The mixture was settled for 7 minutes on a warm water bath of 37° C. for fusion. After the fusion, 15 ml in total of MEM was gradually added to the cells, followed by centrifugation at 750 rpm for 15 minutes. The supernatant was then removed. The cell sediment was suspended in GIT medium (Wako Pure Chemical Industries, Ltd.) containing 10% fetal calf serum (GIT-10% FCS) in $2\times10^5$ P3U1/ml. The suspension was plated in 192 wells of a 96-well multi-dish (manufactured by Linbro) by 1 ml each/well. After plating, the cells were incubated in a 5% carbon dioxide gas incubator at 37° C. After 24 hours, HAT selective culture was initiated by adding GIT-10% FCS medium (HAT medium) containing HAT ($1\times10^{-4}$ M hypoxanthine, $4\times10^{-7}$ M aminopterin and $1.6\times10^{-3}$ M thymidine) by 1 ml each/well. On Days 5 and 8 after the initiation of the culture, 1 ml of old medium was discarded and 0.1 ml of HAT medium was added to continue the HAT selective culture. On Day 9 after the cell fusion, the supernatant was collected.

The antibody titer in the culture supernatant was assayed by a modification of the method described in EXAMPLE. That is, 0.07 ml of the culture supernatant and 0.07 ml of Buffer EC were added to each well of the anti-mouse immunoglobulin antibody-bound microplate. After reacting at 4° C. overnight, 0.1 ml of the HRP-labeled A chain N-terminal peptide diluted to 1000-fold with buffer C was reacted at room temperature for 7 hours in the presence or absence of 0.002 mM non-labeled C-terminal peptide. After the plate was washed with PBS, the enzyme activity on the solid phase was assayed by the method described in EXAMPLE 13. As a result, wells, on which a specific antibody titer was noted, were selected from 168 wells, and the hybridomas were freeze-stored. Furthermore, hybridomas in the wells were cloned by the dilution method. After cloning, the antibody titer in the culture supernatant was assayed in a similar manner.

The anti-C-terminal peptide monoclonal antibody-producing hybridoma was selected from the positive clones.

Example 14

Purification of Monoclonal Antibody

The monoclonal antibody from the hybridoma was purified through Protein-A column. That is, after about 25 ml of the hybridoma supernatant was diluted with an equal volume of binding buffer (1.5 M glycine, pH 9.0, containing 3.5 M NaCl and 0.05% NaN$_3$), the dilution was passed through recombinant Protein-A agarose (manufactured by Repligen, Inc.) previously equilibrated with the binding buffer. The specific antibody was eluted with an elution buffer (0.1 M citrate buffer, pH 3.0, containing 0.05% NaN$_3$). After dialysis to PBS, pH 7.4, at 4° C. for 2 days, the eluate was subjected to cell-free filtration through a 0.22 μm filter (manufactured by Millipore) and stored at 4° C. or −80° C.

Example 15

Assay for Antibody Titer in Antisera of the C-Terminal Peptide-Immunized Rabbit and Preparation of Polyclonal Antibody The antibody titer in rabbit antisera was assayed by the following method. In order to prepare an anti-rabbit immunoglobulin antibody-bound microplate, first, a 0.1 ml aliquot of 0.1 M carbonate buffer solution, pH 9.6, containing 0.1 mg/ml of goat anti-rabbit immunoglobulin antibody (IgG fraction, manufactured by Cappel) was dispensed onto a 96-well microplate, which was allowed to stand at 4° C. for 24 hours. Next, the plate was washed with phosphate buffered saline (PBS, pH 7.4). In order to block the excessive binding sites, 0.3 ml each of PBS, pH 7.2, containing 25% Block Ace (manufactured by Snow Brand Milk Products Co., Ltd.) and 0.05% NaN$_3$ was added to the plate, followed by treatment at 4° C. for at least 24 hours. To each well of the anti-rabbit immunoglobulin antibody-bound microplate described above, 0.14 ml of the rabbit antiserum diluted with buffer EC [0.02 M phosphate buffer, pH 7.0, containing 0.2% BSA, 0.4 M NaCl, 0.4% Block Ace, 0.05% CHAPS [3-[(cholamidopropyl)dimethylammonio] propanesulfonic acid], 2 mM EDTA and 0.05% NaN$_3$] was added, followed by reacting at 4° C. for 16 hours. Next, after the plate was washed with PBS, pH 7.4, 0.1 ml of the HRP-labeled C-terminal peptide prepared in EXAMPLE above and diluted to 100-fold with buffer C [0.02 M phosphate buffer, pH 7.0, containing 1% BSA, 0.4 M NaCl and 2 mM EDTA] was added, followed by reacting at 4° C. for a day. Then, after the plate was washed with PBS, pH 7.4, 0.1 ml of TMB microwell peroxidase substrate system (KIRKEGAARD & PERRY LAB., dealt through Funakoshi Pharmaceutical Co., Ltd.) was added and the mixture was reacted for 20 minutes at room temperature for assay. After 0.1 ml of 1 M phosphoric acid was added to terminate the reaction, absorbance at 450 nm (Abs. 450) was measured on a plate reader (MTP-120, manufactured by Corona Co. or Multiskan Ascent manufactured by Labsystems, Inc.). An increase of the antibody titer to the C-terminal peptide was noted in two out of the 3 rabbits immunized. In addition, rabbit sera showing an increased antibody titer were collected, and antigen purification was carried out in a conventional manner to give the polyclonal antibody.

Example 16

Setting of the Screening Method for an Agonist and Antagonist to the Receptor Using Intracellular Calcium Level Changes as an Indicator In order to set up the system for searching an agonist and antagonist to GPR40, the assay system was set using palmitic acid identified to be the agonist.

Human GPR40-expressed CHO cell line (CHO-hGPR40 No. 104) prepared by publicly known methods using human GPR40 expression vector prepared in REFERENCE EXAMPLE 1, was diluted so as to contain $3\times10^4$ cells/100 μl. The dilution was dispensed in a Black walled 96-well plate (Costar) in 100 μl/well, followed by incubation overnight in a CO$_2$ incubator. Changes in intracellular calcium level were measured using FLIPR (Molecular Device), which procedures were described below.

In 21 μl of DMSO (DOJIN) 50 μg of Fluo-3AM (DOJIN) was dissolved and an equal volume of 20% Pulronic acid (Molecular Probes) was further added to and mixed with the solution. The mixture was then added to 10.6 ml of the assay buffer [which was prepared by adding 20 ml of 1M HEPES (pH 7.4) (DOJIN) to HBSS (Invitrogen) and further adding thereto 10 ml of a solution mixture, which was obtained by dissolving 710 mg of Probenecid (Sigma) in 5 ml of 1N NaOH and 5 ml of the HBSS/HEPES solution described above] supplemented with 105 μl of fetal calf serum to prepare a fluorescent dye solution. The medium in the cell plate was removed. Immediately thereafter, the fluorescent dye solution was dispensed in 100 μl each/well and the cells were incubated in a CO$_2$ incubator for an hour so that the fluorescent dye was taken up into the cells. The cells after the incubation was washed with the assay buffer described above. Palmitic acid added to the cells was diluted to various concentrations using the assay buffer and the dilution was dispensed onto the plate. For the antagonist determination, 12 µM γ-linolenic acid solution (3 µM in the final concentration upon reaction) was dispensed onto the plate and at the same time, set on FLIPR. After the foregoing pre-treatment, changes in intracellular calcium level after the addition of palmitic acid was measured on FRIPR to examine the agonist action, and then γ-linolenic acid was added to examine the antagonist action. Since palmitic acid is the agonist, the antagonist cannot be assessed in the experiment using palmitic acid, but when a compound having only the antagonist action is added, the activity of suppressing the reaction of γ-linolenic acid will be observed. The $EC_{50}$ value was calculated from the dose-response curve using changes in fluorescent intensity value 30 seconds after the reaction commenced.

Example 17

Figure 20:
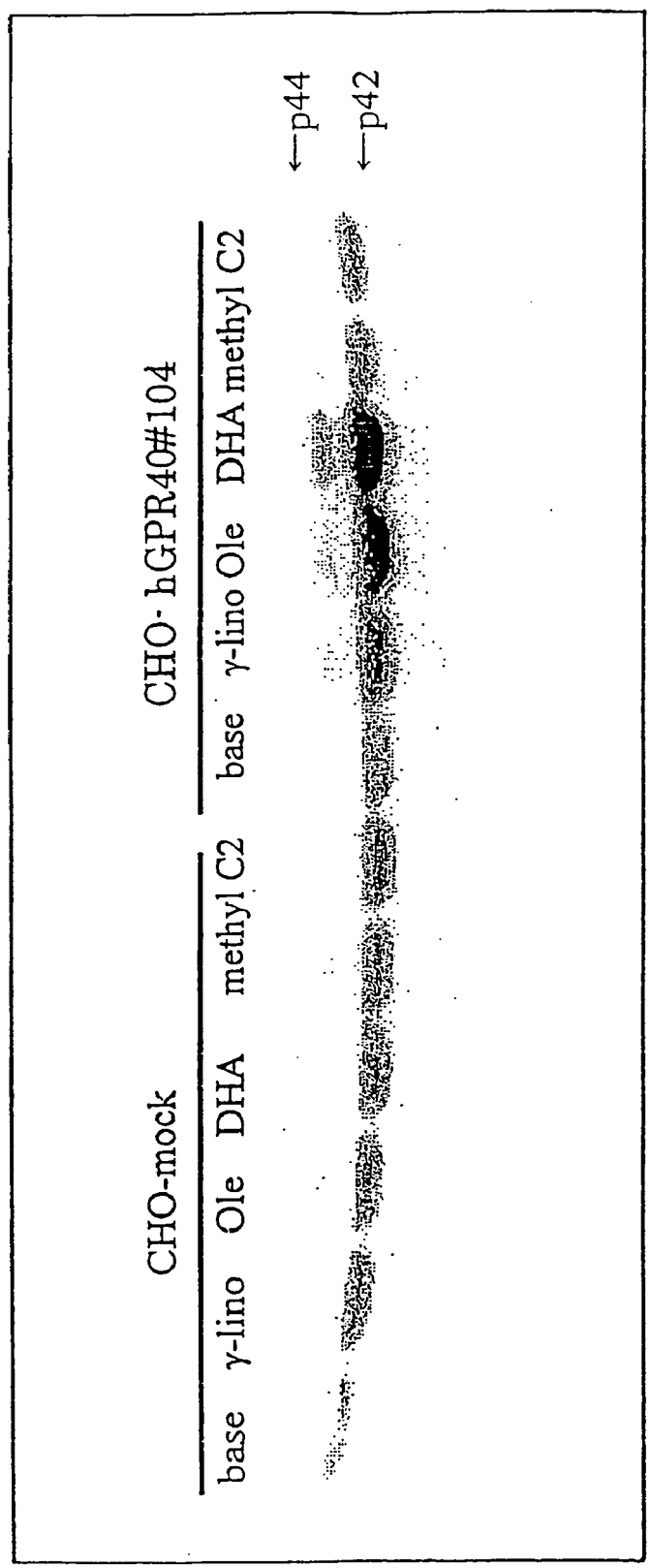
FIG. 20 shows the results of MAP kinase activation by fatty acids detected on CHO-hGPR40 #104. Symbols γ-lino, Ole, DHA, Methyl and C2 denotes γ-linolenic acid, oleic acid, 4Z,7Z,10Z,13Z,16Z,19Z-docosahexaenoic acid, methyl linolate and acetic acid, respectively. CHO-mock denotes CHO cells wherein human GPR40 is not expressed, and CHO-hGPR40 #104 denotes the CHO cell line wherein human GPR40 is expressed. Symbols p44 and p42 denote the bands of p44 MAP kinase and p42 MAP kinase, respectively.

MAP Kinase Activation in hGPR40-Expressed CHO Cells by Addition of the Fatty Acid Human GPR40-expressed CHO cells (CHO-hGPR40 NO. 104) prepared by publicly known methods using the human GPR40 expression vector prepared in REFERENCE EXAMPLE 1 or CHO-mock cells were plated in a 6-well plate at a density of $3\times10^5$/well. The cells were incubated overnight in low serum medium (nucleic acid-free MEMα medium supplemented with 0.5% dialyzed fetal calf serum). The medium was replaced by a serum-free medium (nucleic acid-free MEMα medium) followed by incubation overnight. The medium was replaced by a fresh serum-free medium and after incubation for 4 hours, 10 µM of various fatty acids were added thereto. After incubation for 10 minutes, the cells were lysed/extracted with a sample buffer (TEFCO, Inc.) and separated on SDS-PAGE. Thereafter, western blotting was performed using PhosphoPlus p44/42 MAP kinase (Thr202/Tyr204) Antibody Kit (Cell Signaling Technology, Inc.). As shown in FIG. 20, the results revealed that activation of the protein shown by phosphorylation of MAP kinase after addition of the fatty acid occurred only in human GPR40-expressed CHO cells.

Example 18

Suppressed Expression of Mouse GPR40-GFP Fusion Protein by Introducing siRNA Specific to the Sequence of Mouse GPR40

Figure 21:
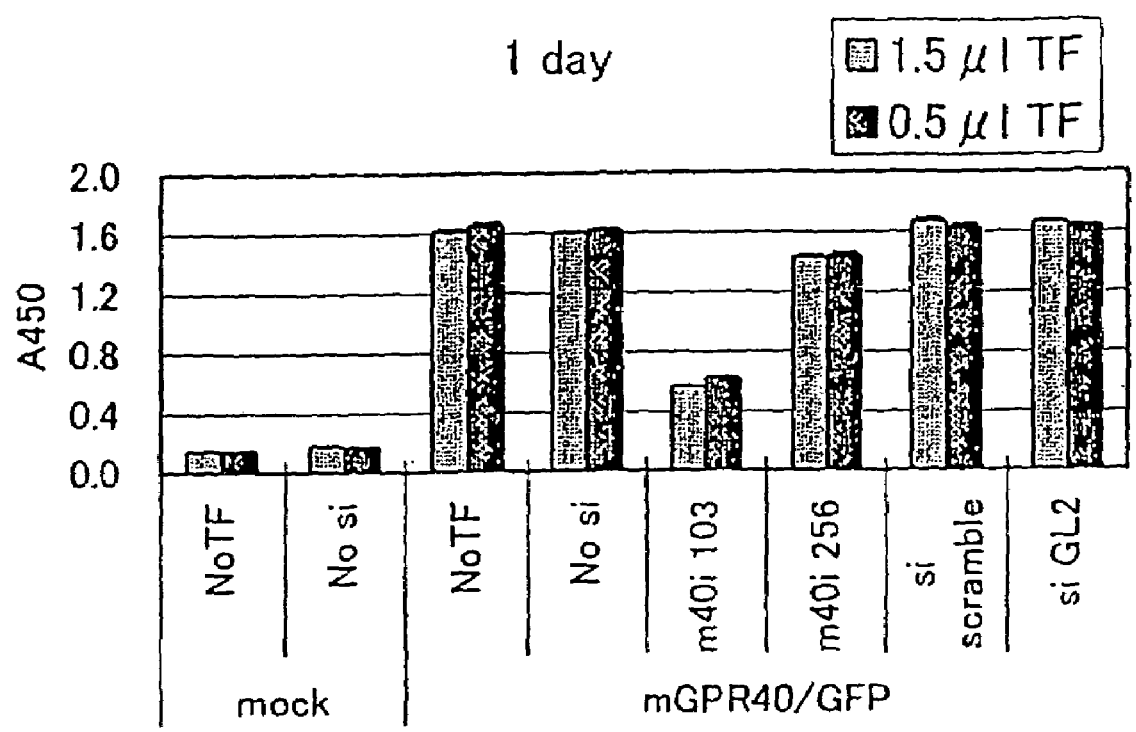
FIG. 21 shows the results of suppressed expression of mouse GPR40-GFP fusion protein by transfecting siRNA specific to the sequence of mouse GPR40. Mock denotes control cells wherein no GPR40-GFP is introduced. NoTF denotes cells with no transfection and No si denotes siRNA-free transfection. Symbols m40i103 and m40i256 denote siRNA specific to the mouse GPR40 sequence, and si scramble and si GL2 denote siRNA have no homology at all to the GPR40 sequence added for negative control. The ordinate designates the expression level of GPR40 (absorbance at 450 nm), which is a mean value+standard deviation when the experiment was conducted in N=3.

Mouse GPR40-GFP fusion protein-expressed CHO cells prepared by publicly known methods were plated in a 96-well plate at a density of $3\times10^4$/well, followed by incubation for a day. The siRNA (Dharmacon, Inc.) having various sequences, which was prepared according to the report by Elbasir et al. (Nature 411 (6836), 494–498 (2001)) using HVJ Envelope VECTOR KIT GenomONE™ (Ishihara Sangyo Kaisha, LTD.), was introduced into the cells (in a concentration of 2.86 pmols/0.5 µl or 8.57 pmols/1.5 µl), incubation followed for further one day. The expression level of mouse GPR40-GFP was detected by enzyme immunoassay as shown below. After the culture supernatant was discarded and the cells were washed with HBSS (Invitrogen), the cells were immobilized on 0.01% glutaraldehyde (Wako Pure Chemical) for 5 minutes, followed by blocking with 2% BSA-containing PBS (Takara Shuzo). Anti-GFP monoclonal antibody 3E6 (Nippon Gene) diluted to 500-fold was added to the cells. After incubation at room temperature for 2 hours, the cells were washed and HRP-labeled anti-mouse IgG antibody (ICN) diluted to 500-fold was added thereto followed by incubation at room temperature for 2 hours. After washing, TMB Microwell peroxidase substrate (Funakoshi) was added to the cells. After incubation for 30 minutes, sulfuric acid was added to stop the color-forming reaction and absorbance was measured at 450 nm. As a result, a reduction in the expression level of GPR40-GFP was noted by adding m40i103 (the sense strand is represented by SEQ ID NO: 34 and the antisense strand by SEQ ID NO: 35) and m40i256 (the sense strand is represented by SEQ ID NO: 36 and the antisense strand by SEQ ID NO: 37), which are mouse GPR40-specific siRNA, to the mouse GPR40-GFP-expressed CHO cells, as shown in FIG. 21. It was noted from the results that m40 i103 and m40i256 specifically suppressed the expression of mouse GPR40. FIG. 22 shows the sequences of m40i103 and m40i256.

Example 19

Construction of DNA Fragment for Preparing Mouse Capable of Expressing Human GPR40 Specifically to Pancreatic β Cells In order to express human GPR40 specifically in the pancreatic β cells of mouse, a DNA fragment transfected with human GPR40 gene containing poly(A)+ addition signal at the downstream of mouse insulin II promoter was prepared. A fragment of human GPR40 gene (SalI-SpeI fragment: 2256 bp) containing from initiation codon to the downstream of poly(A)+ addition signal was inserted at the downstream of mouse insulin II promoter (MluI-SalI fragment: 673 bp) cloned from mouse genome by PCR, which fragment of human GPR40 gene was likewise cloned from human genome by PCR, to prepare the expression unit for expressing human GPR40 gene under control of mouse insulin II promoter. The expression unit thus obtained was subjected to double digestion with MluI and SpeI, whereby the fragment of 2928 bp was excised and made a DNA fragment for microinjection into a fertilized egg of C57BL/6J mouse.

Example 20

Cloning of Mouse GPR40 Gene

Using primers (SEQ ID NO: 38, SEQ ID NO: 39) capable of amplifying the region including mouse GPR40 ORF, mouse 129SvJBAC genome library (Invitrogen, Inc.) was screened to obtain independent 3 positive clones with 384 colonies being mixed up. The independent 3 positive clones with which 384 colonies were mixed up underwent colony hybridization using the DNA fragment (1.6 kbp) obtained in the above PCR by SEQ ID NO: 38 and SEQ ID NO: 39 to finally isolate 3 positive single clones.

Figure 23:
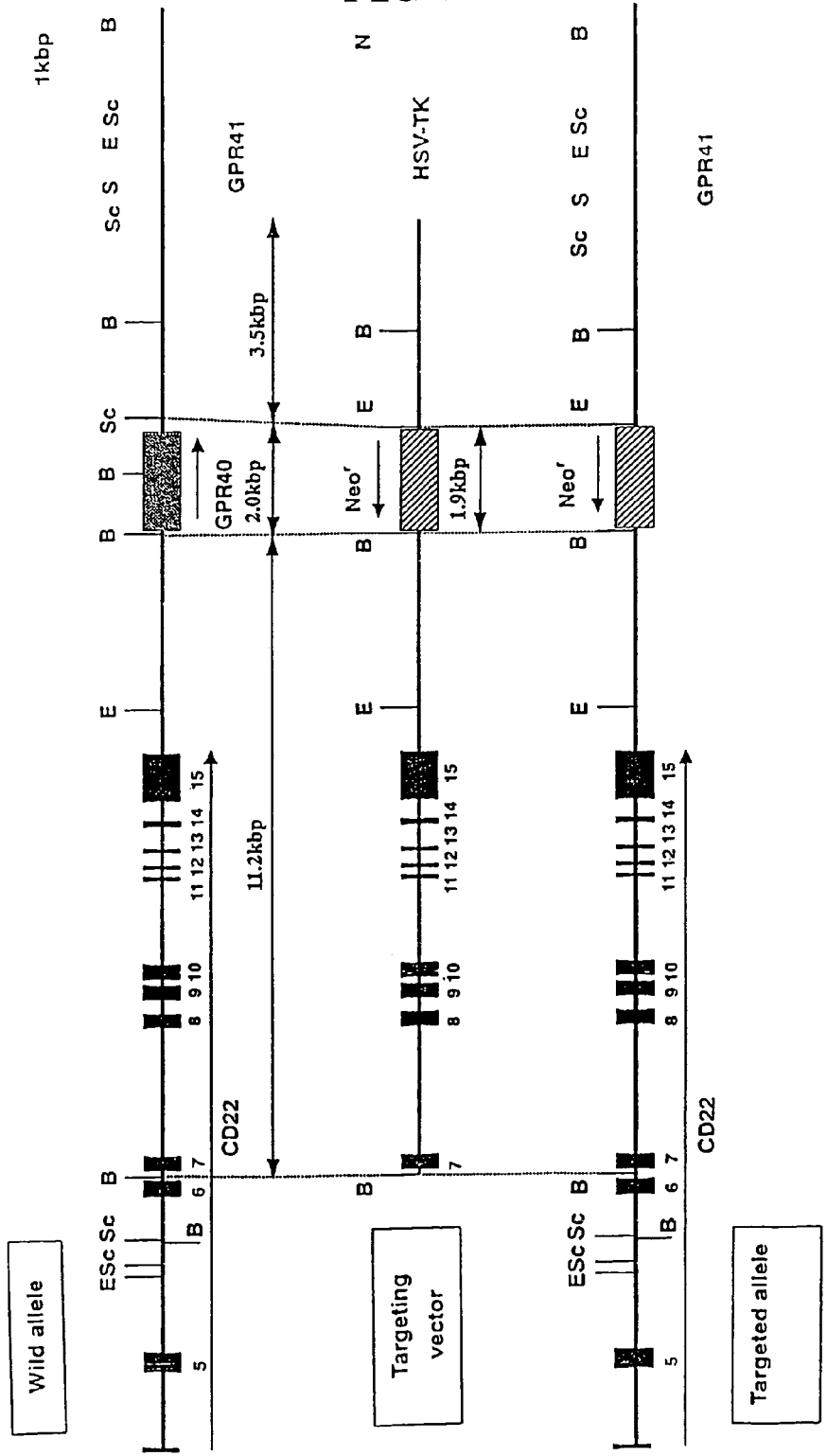
FIG. 23 shows a construction map of the GPR40 targeting vector.

After BAC DNA borne on the clones was isolated in a conventional manner, base sequencing was performed for the region of about 25 kb suspected of the presence of GPR40 gene using a sequencer (Perkin-Elmer, Inc.). Based on this base sequence information, a restriction enzyme map was prepared (FIG. 23).

Example 21

Construction of GPR40 Gene Targeting Vector

Construction of mouse GPR40 gene targeting vector was carried out by introducing into a basic vector pGT-N-28 (New England Biolabs, Inc.) the 11151 bp BamHI fragment of GPR40 gene obtained in EXAMPLE 20 as the 5' downstream arm and the 3458 bp Ecl136II (Sac) fragment as the 3' downstream arm. Thus, mouse GPR40 gene targeting vector pGT-GPR40 bearing neomycin-resistant gene as a positive selection marker and herpes simplex virus thymidine kinase gene as a negative selection marker was constructed (FIG. 23). The vector was introduced into *Escherichia coli* DH5α to obtain *Escherichia coli* DH5α/pGT-GPR40 as the transformant.

Example 22

Confirmation of the Reactivity of Eicosanoid with Human-Derived GPR40

The CHO cell line (CHO-hGPR40 No. 104) wherein human GPR40 prepared by publicly known methods using the human GPR40 expression vector prepared in REFERENCE EXAMPLE 1 was expressed was cultured in MEMα medium (Invitrogen) containing 10% fetal calf serum (Invitrogen), unless otherwise indicated. The cells cultured were rinsed with PBS (Invitrogen), scraped in trypsin/EDTA solution (Invitrogen) and recovered by centrifugal operation. The number of the cells obtained was counted and diluted so as to contain $3 \times 10^4$ cells/100 µl. The dilution was dispensed in a Black walled 96-well plate (Costar) in 100 µl/well, followed by incubation overnight in a $CO_2$ incubator. The changes in intracellular calcium level in this case were measured using FLIPR (Molecular Device). In order to determine the changes in the intracellular calcium ion level on FLIPR, the cells were pre-treated by the following procedures. First, for the purpose of adding a fluorescent dye Fluo-3 AM (DOJIN) to the cells or washing the cells immediately before the FLIPR assay, an assay buffer was prepared. A solution obtained by adding 20 ml of 1M HEPES (pH 7.4) (DOJIN) to 1000 ml of HBSS (Invitrogen) was prepared (hereinafter HBSS/HEPES solution), to which 10 ml of a solution mixture obtained by dissolving 710 mg of Probenecid (Sigma) in 5 ml of 1N NaOH and further adding 5 ml of HBSS/HEPES solution was added. The resulting solution was used as the assay buffer. Next, 50 µg of Fluo-3AM was dissolved in 21 µl of DMSO (DOJIN) and an equal volume of 20% Pulronic acid (Molecular Probes) was added to and mixed with the solution. The mixture was then added to 10.6 ml of the assay buffer supplemented with 105 µl of fetal calf serum to prepare a fluorescent dye solution. The medium for the CHO cell line cultured was removed. Immediately thereafter, the fluorescent dye solution was dispensed in 100 µl each/well and the cells were incubated in a $CO_2$ incubator for an hour so that the fluorescent dye was taken up into the cells. The cells after the incubation was washed with the assay buffer described above and set on FLIPR. A test sample added to the CHO cell line was prepared using the assay buffer and set on FLIPR at the same time. After the pre-treatment above was made, the changes in intracellular calcium level after the addition of various test samples were measured on FLIPR. The results revealed that the CHO cell line expressing the GPR40 receptor were specifically responsive (increase in intracellular calcium level), when (+)14,15-dihydroxy-5Z,8Z,11Z-eicosatrienoic acid (14,15-DHT), (+)5(6)-epoxy-8Z,11Z,14Z-eicosatrienoic acid (5,6-EET), (+)8(9)-epoxy-5Z,11Z,14Z-eicosatrienoic acid (8,9-EET), (+)11(12)-epoxy-5Z,8Z,14Z-eicosatrienoic acid (11,12-EET) and (+)14(15)-epoxy-5Z,8Z,11Z-eicosatrienoic acid (14,15-EET) were added in $10^{-5}$ M to $10^{-6}$ M. With the CHO cell line into which the expression vector alone for control was introduced, such response was not observed. It was thus noted that GPR40 was responsive to these compounds as well.

Example 23

Study on the Expression Disruption of GPR40 mRNA in the Islet by In Situ Hybridization Wistar rat was sacrificed and the bile duct duodenal opening was ligated. Then, 1 mg/ml of chilled collagenase/HBSS was infused through the bile duct. The pancreas infused with collagenase was cut out, transferred to a conical tube and incubated for 10 minutes while infiltrating at 37° C. After HBSS was added thereto and the tissue was thoroughly dispersed by pipetting, the tissue was settled for 3 to 4 minutes to precipitate the tissue containing the islet. The supernatant was removed. After this operation was repeated twice, the precipitate was resuspended in HBSS and the islet was picked up stereomicroscopically. The islet isolated as described above was frozen with liquid nitrogen in O.C.T. compound and stored at −80° C.

GPR40 antisense and sense probe were prepared by the following procedures. First, rat GPR40 cDNA was inserted into plasmid vector pCRII TOPO (Invitrogen, Inc.) by publicly known methods. This cDNA was amplified/linearly stranded by PCR using M13 primer (Invitrogen, Inc.)/Advantage GC2 polymerase (Clontech, Inc.), followed by purification through ethanol precipitation. This cDNA was subjected to in vitro transcription (40 µl scale) by SP6 or T7 using DIG RNA Labelling KIT (SP6/T7) (Roche, Inc.). The resulting DIG-labeled riboprobe was alkali-hydrolyzed further to 400 bp with 40 mM $NaHCO_3$ and 60 mM $Na_2CO_3$, pH 10.2, followed by purification through ethanol precipitation. The purified probe was dissolved in 100 µl of Otsuka purified water. Based on the insertion direction of cDNA, the DIG-labeled riboprobe produced by SP6 and the DIG-labeled riboprobe produced by T7 were identified to be an antisense probe and a sense probe, respectively.

For in situ hybridization, the fresh frozen section of islet isolated was used. First, the isolated islet described above was sliced in a thickness of 16 µm on a silane-coated slide using Cryostat CM3050 (Leica, Inc.). The slice was fixed in 4% paraformaldehyde-containing PBS for 10 minutes, then thoroughly washed with PBS and treated (room temperature, 10 minutes) with 0.1 M triethanolamine (pH 8.0) containing 0.25% acetic anhydride to effect acetylation. For hybridization, the antisense probe or sense probe was diluted to 1000-fold with a hybridization buffer (50% formaldehyde, 10 mM Tris-HCl, pH 7.5, 1× Denhardt's solution, 200 µg/ml tRNA, 10% dextran sulfate, 600 mM NaCl, 0.25% SDS, 1 mM EDTA), denatured at 85° C. for 10 minutes, and then added to the slice, followed by reacting at 50° C. for at least 12 hours. Subsequently, the following procedures were carried out to wash the probe hybridized non-specifically. 1) A treatment with 2×SSC(SSC; 1×SSC=150 mM NaCl, 15 mM sodium citrate, pH 7.0)/50% formamide (60° C. for 30 minutes, once), 2) a treatment with 2×SSC (60° C. for 15 minutes, once) and 3) a treatment with 0.1×SSC (60° C. for 15 minutes, twice). Following the procedures above, immunohistochemistry was effected to detect the DIG-labeled probe. First, after washing with DIG-1 (100 mM Tris-HCl, pH 7.5, 150 mM NaCl, 0.1% Tween 20), non-specific reactions were blocked by a treatment (37° C. for an hour) with DIG-1 containing 1.5% Blocking reagent (Roche, Inc.), and DIG-1 (1:1000) containing anti-DIG fab-fragment antibody conjugated with alkaline phosphatase (Roche, Inc.) was reacted at room temperature for an hour. After thoroughly washing with DIG-1, the islet was rinsed with DIG-3 (100 mM Tris-HCl, pH 9.5, 100 mM NaCl, 50 mM $MgCl_2$) and color-forming reaction was carried out at room temperature in solutions obtained by adding dimethylformamide containing 0.18 mg/ml 5-bromo-4-chloro-3-indolyl-phosphate (BCIP), 70% dimethylformamide containing 0.34 mg/ml 4-nitroblue tetrazolium (NBT) and polyvinyl alcohol in amounts of 0.35 ml, 0.45 ml and 3%, respectively, based on 10 ml of DIG-3. The color formation was appropriately terminated by PBS washing, and the system was moved to insulin-glucagon immunohistochemical operations.

First, non-specific reactions were blocked by 1% BSA-containing PBS, and incubation was performed for 12 hours in 0.5% BSA/PBS containing rabbit anti-insulin serum (H-86: Santa Cruz, 1/200) and anti-glucagon monoclonal antibody (K79bB10: SIGMA, 1/8000). After washing with PBS, the islet was reacted with 0.5% BSA/PBS containing 10 µg/ml Alexa 488-conjugated goat anti-mouse IgG (Molecular Probes, Inc.) and 10 µg/ml Alexa 594-conjugated goat anti-rabbit IgG (Molecular Probe, Inc.) at room temperature for 2 hours. After washing with PBS, the islet was included in PBS containing 90% glycerol, which was observed by an optical microscope and a fluorescence microscope.

A positive signal was observed in the isolate islet by the GPR40 antisense probe. The positive signal was ubiquitously observed over the whole islet. In these regions, color formation was not detected by the sense probe. On the other hand, on the fluorescence microscopic observation, a glucagon immune positive signal was observed in the cells around the islet and an insulin immune positive signal was observed in the remaining parts, as already known. In comparison between the signal by the GPR40 antisense probe and the immune positive signal of insulin/glucagon, the signal by GPR40 was observed in the insulin immune positive cells, whereas any clear signal by GPR40 was not observed in the glucagon immune positive cells. The foregoing results suggested a possibility that GPR40 mRNA would be β cell-specifically expressed in the islet.

Example 24

MAP Kinase Activation in MIN6 Cells by the Addition of Fatty Acids

Figure 24:
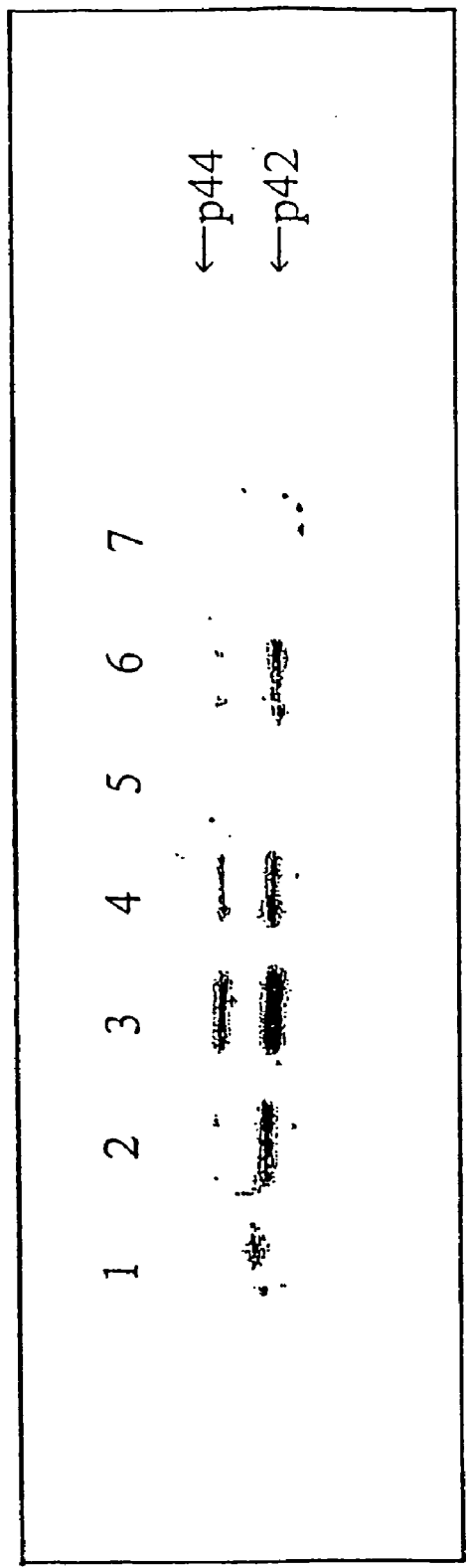
FIG. 24 shows the results of MAP kinase activation by fatty acids detected on MIN6. Lanes 1, 2, 3, 4, 5, 6 and 7 denote control, the addition with oleic acid, with linoleic acid, with γ-linolenic acid, with methyl linolate, with linoleic acid and with linoleic acid+PD98059 (50 μM), respectively, wherein Lanes 1–5 are the results after incubation for 2.5 minutes and Lanes 6–7 are the results after incubation for 5 minutes. The concentration of each fatty acid is 10 μM. Symbols p44 and p42 denote the bands of p44 MAP kinase and p42 MAP kinase, respectively.

The medium used was 4.5 g/l of glucose-containing Dulbecco's Modified Eagle Medium (DMEM, Invitrogen, Inc.) supplemented with 15% fetal calf serum (ThermoTrace, Inc.), 5.5 µM 2-mercaptethanol (Invitrogen, Inc.), 20 mM HEPES pH 7.3, 100 U/ml penicillin and 100 µg/ml streptomycin. The mouse pancreatic β cell line MIN6 cells were plated in a 12-well plate at a density of $2 \times 10^5$/well and incubated overnight. On the following morning, the medium was exchanged and incubation was continued overnight. The medium was again exchanged on the following morning. After incubation for 3 hours, preincubation was carried out in 22 mM glucose-containing KRBH for an hour. Various fatty acids were dissolved in KRBH (22 mM glucose) at a density of 10 µM followed by incubation for 2.5 minutes (or 5 minutes). MAPK inhibitor (PD98059) was added to KRBH in a concentration of 50 µM during the preincubation/incubation. After lysis/extraction in a sample buffer (TEFCO, Inc.), the cells were separated on SDS-PAGE and analyzed by western blotting using PhosphoPlus p44/42 MAP kinase (Thr202/Tyr204) Antibody Kit (Cell Signaling Technology, Inc.). As shown in FIG. 24, the results revealed that activation of the protein noted by phosphorylation of MAP kinase occurred only when the fatty acids having the agonist activity in the FLIPR assay (Lanes 2, 3 and 4) using GPR40-expressed CHO cells were added, and the activation of MAPK was almost suppressed by the addition of PD98059. The activation of MAPK occurred by the fatty acids showing the agonist activity in MIN6 as well as in the GPR40-expressed CHO cells. Thus, it was strongly supported that GPR40 would take part in MIN6 stimulation of fatty acids at least in part.

Example 25

Insulin Secretion Promotion from MIN6 by Various Fatty Acids

Figure 25:
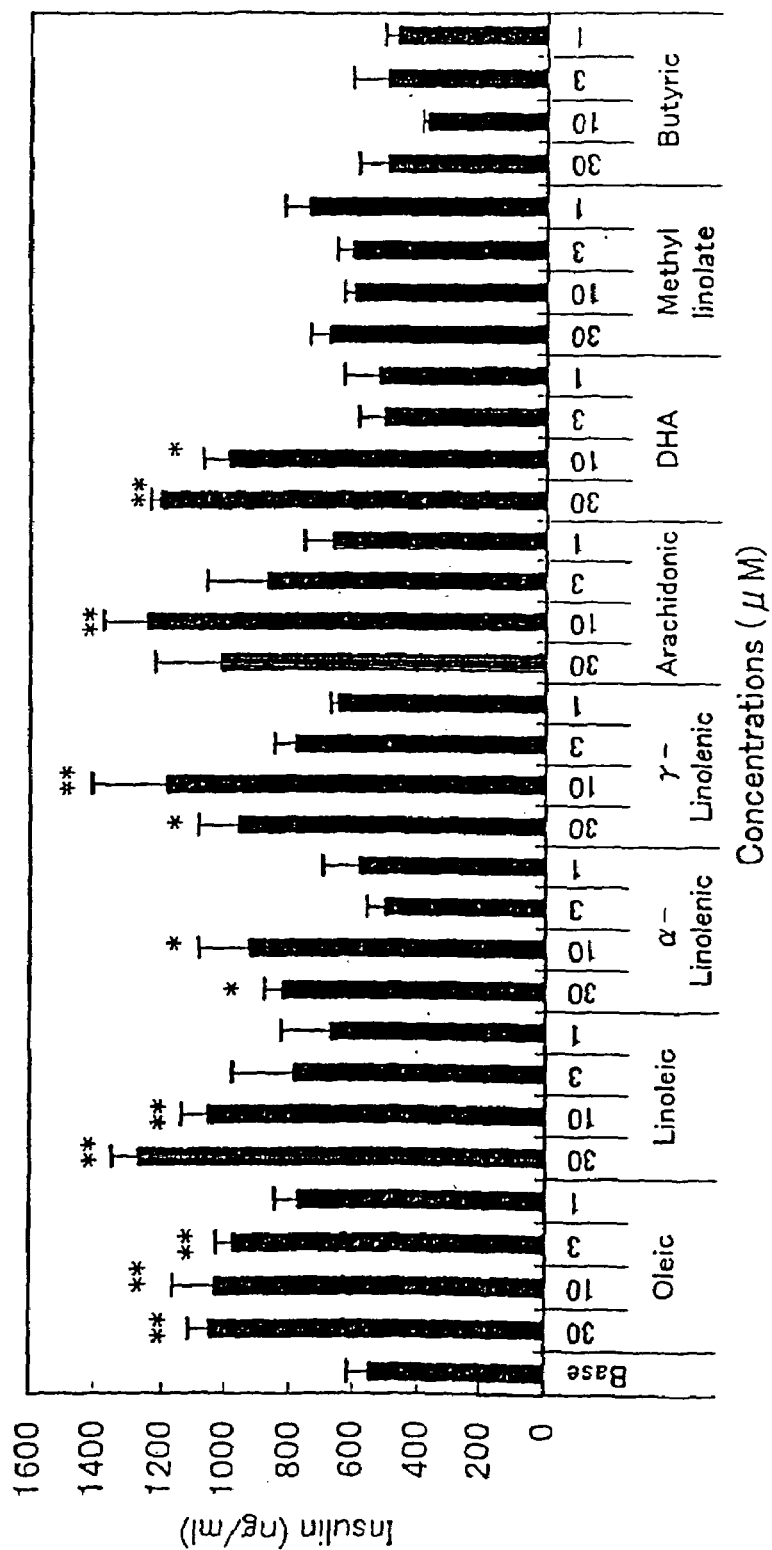
FIG. 25 shows the insulin secretion promoting action from MIN6 by various fatty acids prepared in 22 mM glucose-containing KRBH. Concentrations on the abscissa denote the concentrations of fatty acids (μM), wherein Base, Oleic, Linoleic, α-Linolenic, γ-Linolenic, Arachidonic, DHA, Methyl linolate and Butyric denote no addition, the addition with oleic acid, with linoleic acid, with α-linolenic acid, with γ-linolenic acid, with arachidonic acid, with docosahexaenoic acid, with methyl linolate and with butyric acid, respectively. The ordinate designates the insulin level (ng/ml). The values are the mean+standard deviation (n=4). Symbols ** and * denote $p<0.01$ and $p<0.05$ (Student's t test), respectively.

The mouse pancreatic β cell line MIN6 incubated in a flask was scraped in PBS containing 2.5 mM EDTA and plated in a 96-well plate followed by incubation for 2 days. The medium used was the same as in EXAMPLE 24, namely, 4.5 g/l of glucose-containing Dulbecco's Modified Eagle Medium (DMEM, Invitrogen, Inc.) supplemented with 15% fetal calf serum (ThermoTrace, Inc.), 5.5 µM 2-mercaptethanol (Invitrogen, Inc.), 20 mM HEPES pH 7.3, 100 U/ml penicillin and 100 µg/ml streptomycin. The cells were washed twice with modified Krebs-Ringer bicarbonate buffer (KRBH, 116 mM NaCl, 4.7 mM KCl, 1.2 mM $KH_2PO_4$, 1.2 mM $MgSO_4$, 2.5 mM $CaCl_2$, 25 mM $NaHCO_3$, 24 mM HEPES, pH 7.3), followed by preincubation at 37° C. in 5% $CO_2$ for 30 minutes. The fatty acid diluted/prepared using the aforesaid KRBH buffer added with 22 mM glucose was added to the cells after the preincubation, followed by incubation under the conditions of 37° C. in 5% $CO_2$ for 90 minutes. After the incubation, the supernatant of the cells was recovered and stored in a frozen state. The insulin content in the supernatant was assayed using an insulin immunoassay kit commercially available (Amersham Pharmacia, Inc.). As a result, the insulin secretion enhancing activity was significantly noted with oleic acid, linoleic acid, α-linolenic acid, γ-linolenic acid, arachidonic acid and DHA, which were the fatty acids showing the marked activity in the intracellular calcium ion mobilization assay using the GPR40-expressed CHO cells, as shown in FIG. 25. On the other hand, methyl linolate (linoleic methyl) and butyric acid (Butyric acid) displaying no agonist activity on GPR40 did not show any significant insulin secretion enhancing activity. Since the GPR40 agonist activity was almost co-related to the insulin secretion enhancing activity, it was established that GPR40 is responsible for at least a part of the insulin secretion enhancing activity by fatty acids.

Example 26

Glucose Dependency in the Insulin Secretion Enhancing Activity Mediated by GPR40

Figure 26:
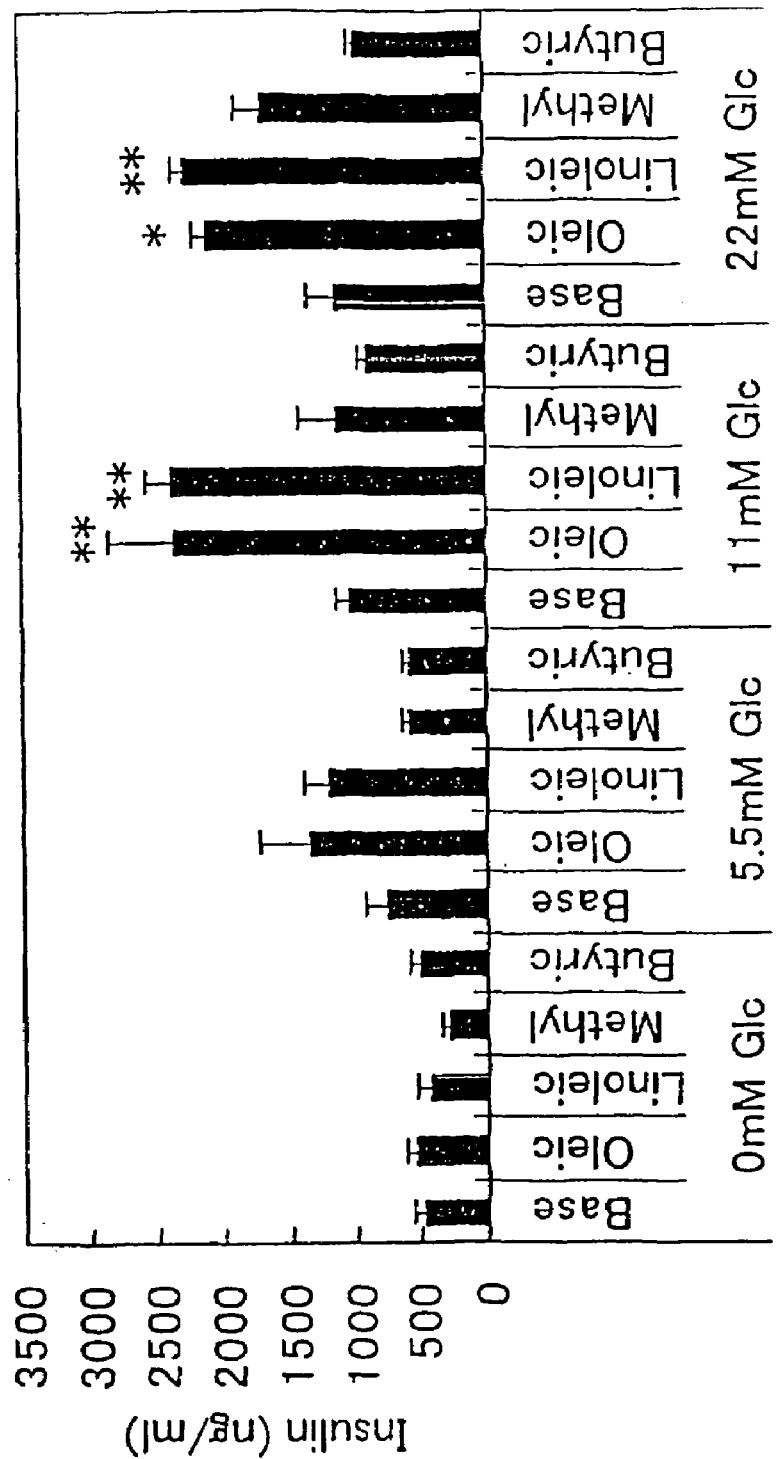
FIG. 26 shows glucose concentration dependency of the insulin secretion promoting activity from MIN6 by fatty acids. The abscissa designates the kinds of fatty acids (10 μM) added, wherein Base, Oleic, Linoleic, Methyl and Butyric denote no addition, the addition with oleic acid, with linoleic acid, with methyl linolate and with butyric acid, respectively. Glc denotes glucose. The values are the mean+standard deviation (n=4). Symbols ** and * denote $p<0.01$ and $p<0.05$ (Student's t test), respectively. Glc denotes glucose. The ordinate designates the insulin level (ng/ml). The values are the mean values+standard deviation (n=4). Symbols ** and * denote $p<0.01$ and $p<0.05$ (Student's t test), respectively.

Based on the method of EXAMPLE 25, effects of glucose level when added with fatty acids were examined. The level of glucose, which was added to KRBH upon the addition of fatty acids, was varied to 0, 5.5, 11 and 22 mM to study the effects. As shown in FIG. 26, the results revealed that the insulin secretion enhancing activity by oleic acid and linoleic acid was remarkable under high glucose level conditions of at least 11 mM. From the results it was expected that the insulin secretion increasing action by fatty acids showing the agonist activity on GPR40 would result in the insulin secretion increasing action/blood sugar action under high blood sugar conditions.

Example 27

Effect of Suppressing the Insulin Secretion Enhancing Activity by Fatty Acids in siRNA-Introduced MIN6

Figure 27:
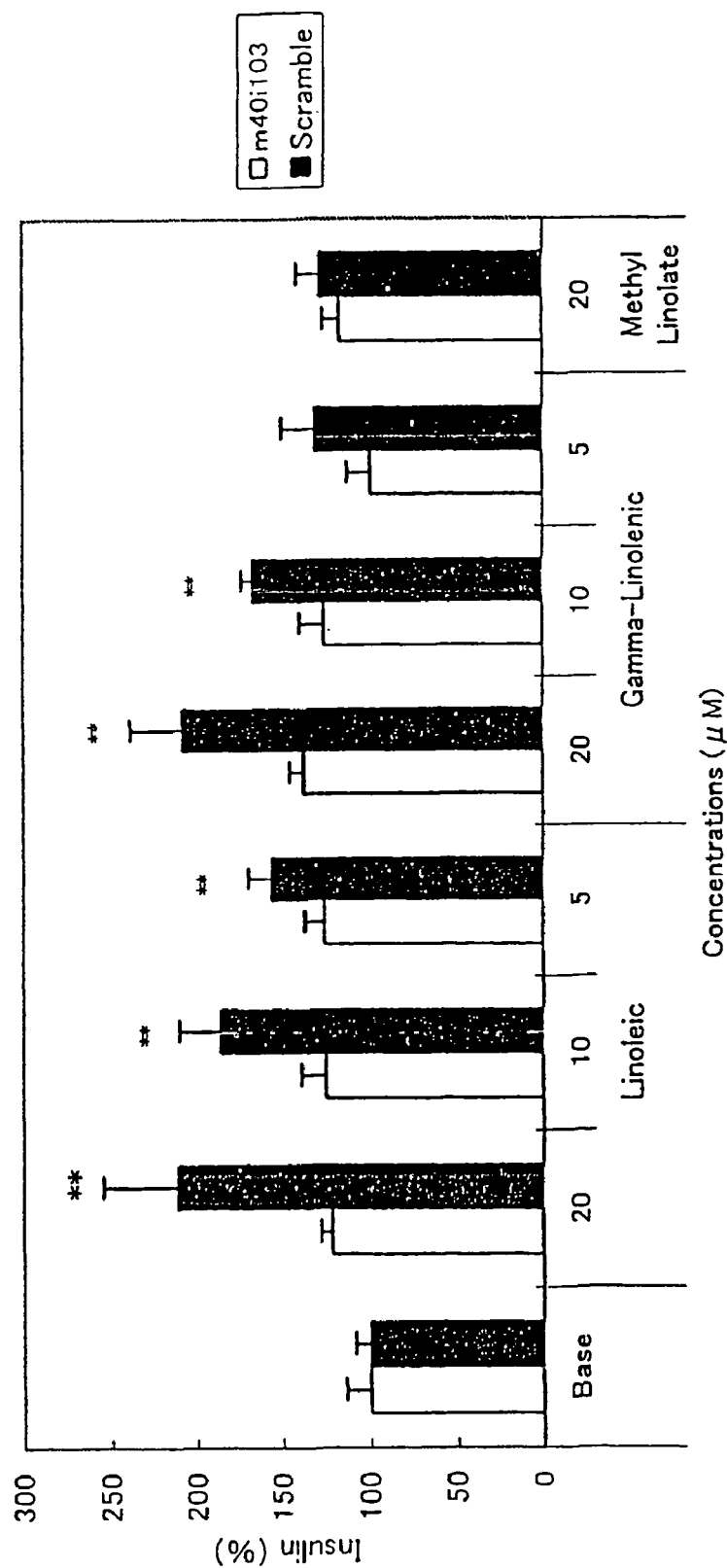
FIG. 27 shows the suppression effects of the insulin secretion enhancing activity by fatty acids on siRNA-transfected MIN6. The abscissa designates the concentrations of fatty acids (μM) added, wherein Base, Linoleic, Gamma-Linolenic and Methyl linolate denote no addition, the addition with linoleic acid, with γ-linolenic acid and with methyl linolate, respectively. The ordinate designates the secreted insulin level, which was expressed in terms of % based on Base. The white column open square and the solid black column closed square denote the cases where m40i103 was transfected and where Scramble II duplex siRNA was transfected, respectively. The values are the mean+standard deviation (n=4). Symbol ** denotes $p<0.01$ (Student's t test vs. Base).

It was already confirmed in EXAMPLE 18 that m40i103, which was a GPR40-specific siRNA, markedly suppressed the expression of mouse GPR40. The insulin secretion enhancing activity in the m40i103-introduced MIN6 cells using HVJ Envelope VECTOR KIT GenomONE based on the method of EXAMPLE 18 was examined. The insulin secretion enhancing activity by fatty acids was examined according to the method of EXAMPLE 25. As shown in FIG. 27, the insulin secretion enhancing activity by linoleic acid and γ-linolenic acid was no longer noted in the m40i103-introduced MIN6. On the other hand, it was noted in MIN6 introduced with random siRNA, i.e., Scramble II duplex siRNA that the insulin secretion enhancing activity by the aforesaid fatty acids was retained. From the results, it was confirmed that GPR40 was responsible at least in part for the mechanism of insulin secretion increased by fatty acids.

Example 28

Figure 28:
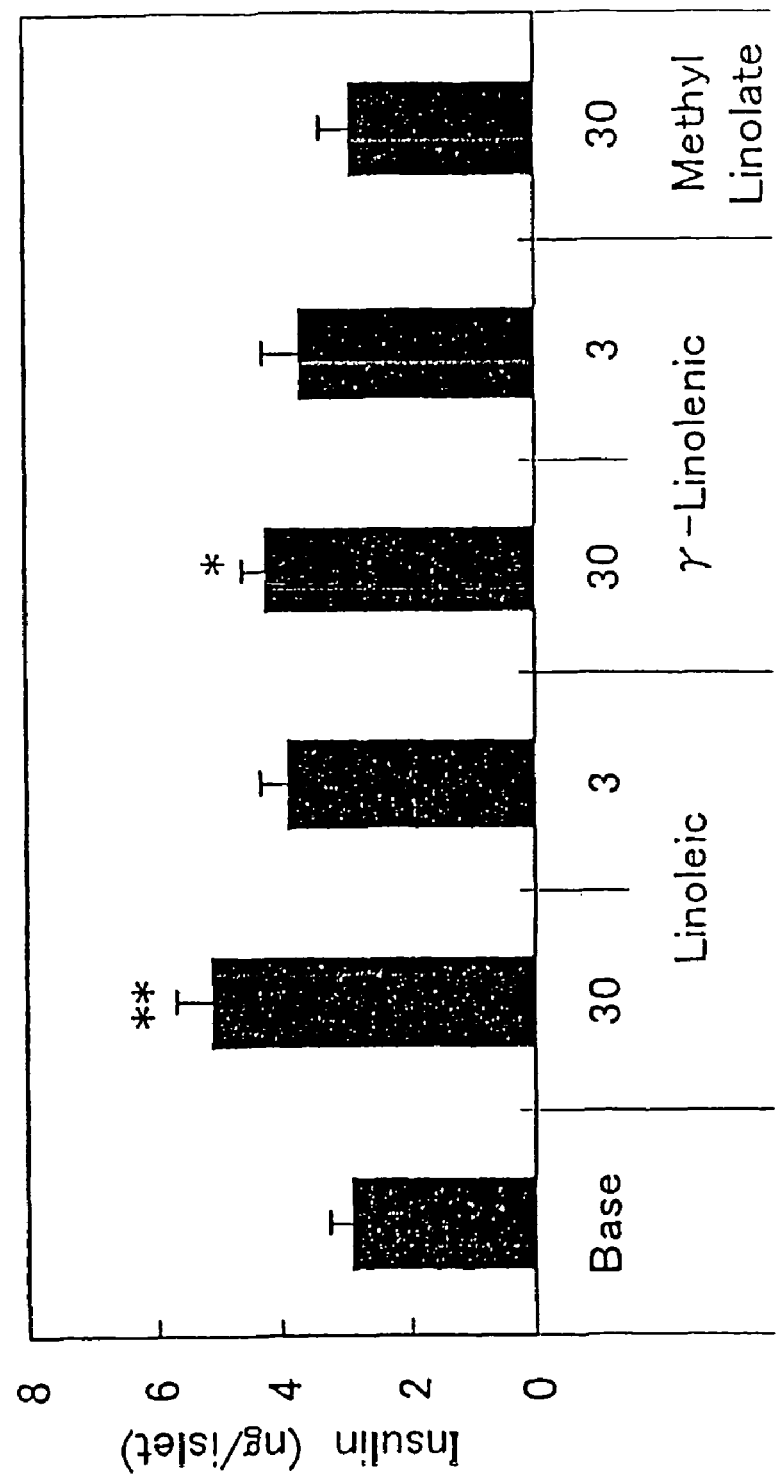
FIG. 28 shows the insulin secretion promoting activity by fatty acids in rat Langerhans islets. The abscissa designates the concentrations of fatty acids (μM) added, wherein Base, Linoleic, γ-Linolenic and Methyl linolate denote no addition, the addition with linoleic acid, with γ-linolenic acid and with methyl linolate, respectively. The ordinate designates the secreted insulin level (ng) per islet. The values are the mean+standard deviation when 3 runs in total were carried out in n=3 and n=4. Symbols ** and * denote p<0.01 and p<0.05 (Student's t test), respectively. The values are the mean values+standard deviation (n=4). Symbols ** and * denote p<0.01 and p<0.05 (Student's t test), respectively.

Insulin Secretion Activity by Fatty Acids in the Primary Culture of Rat Pancreatic Langerhans Islet Langerhans islet was isolated from the pancreas of 8 week-old male Wistar rats (Charles River Japan) by the collagenase digestion method. Approximately 1000 Langerhans islets isolated from 6 animals were washed twice with KRBH (2.8 mM Glucose) and preincubated at 37° C. for 30 minutes in the presence of 5% $CO_2$, as they were. After centrifugation, the supernatant was discarded and the islets were uniformly resuspended in KRBH (2.8 mM Glucose) in a concentration of 140 islets/mL. A 100 μL aliquot of the suspension was dispensed in a 96-well plate. KRBH (finally 16.5 mM Glucose) containing various fatty acid samples including linoleic acid, γ-linolenic acid and methyl linolate (finally 30 μM or 3 μM) was added to the plate in 100 μL each, followed by incubation at 37° C. for 90 minutes in the presence of 5% $CO_2$. The insulin level in the supernatant was determined using a commercially available immunoassay kit (Amersham). As shown in FIG. 28, the insulin secretion promoting activity was confirmed also in the rat pancreatic Langerhans islets by treating with the fatty acids showing the agonist activity to GPR40. It was confirmed that GPR40 was involved in insulin secretion not only in the β cell line MIN6 examined in EXAMPLEs 25 through 27 but in the normal pancreatic Langerhans islets as well.

Example 29

Essential Prerequisite of $Ca^{2+}$ Ions for Insulin Secretion Mediated by GPR40

Figure 29:
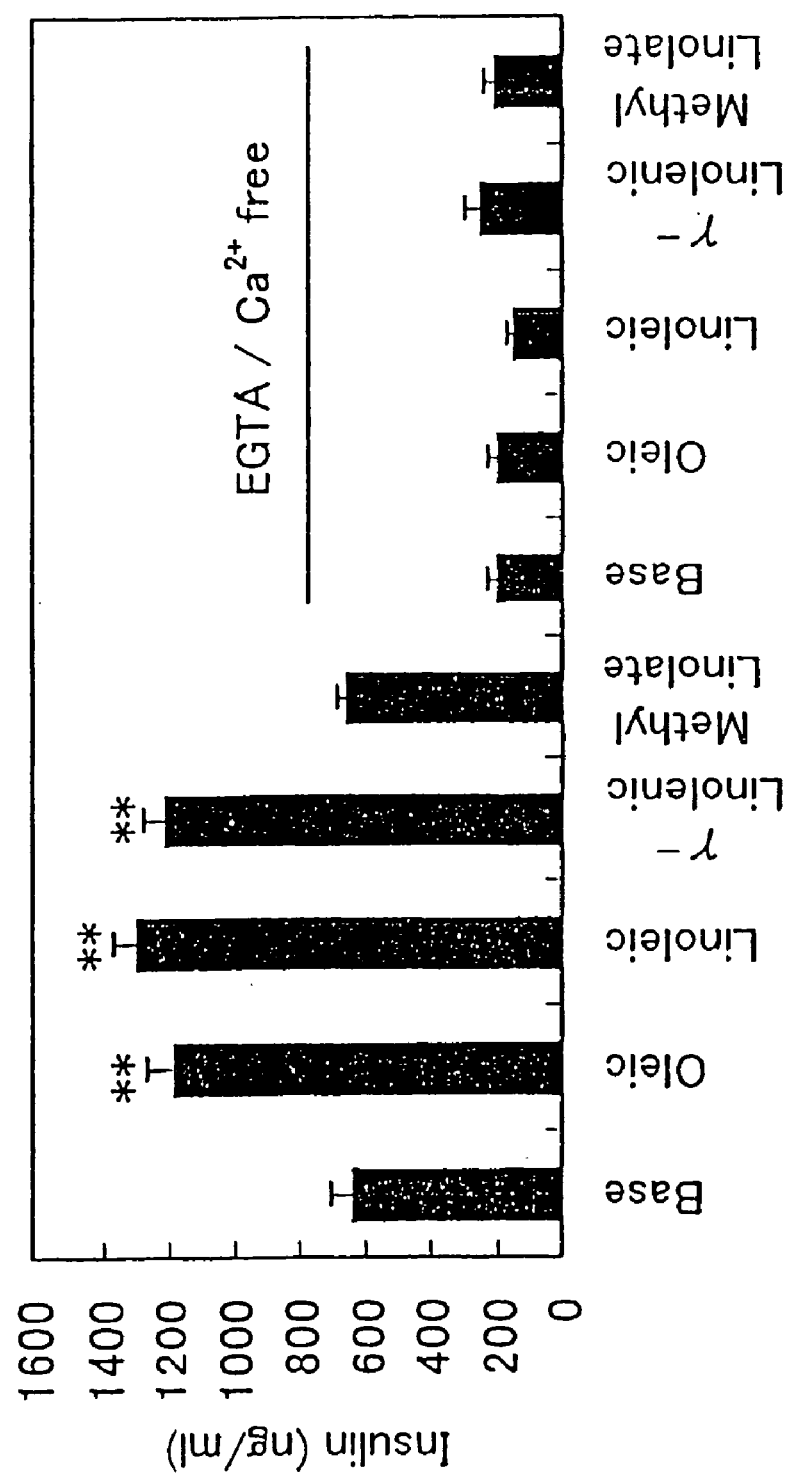
FIG. 29 shows the results obtained by testing the necessity for $Ca^{2+}$ ions in promoting insulin secretion from MIN6 by fatty acids. The abscissa designates the fatty acids added, wherein Base, Oleic, Linoleic, γ-Linolenic and Methyl linolate denote no addition, the addition with oleic acid, with linoleic acid, with γ-linolenic acid and with methyl linolate, respectively. The left group indicates, respectively, the case where the fatty acid (10 μM) prepared from 22 mM glucose-containing KRBH was added, and the right group shown by EGTA/$Ca^{2+}$ free indicates the case where the fatty acid (10 μM) prepared in 0.1 mM EGTA-containing KRBH, from which $Ca^{2+}$ ions were removed with 22 mM glucose-containing KRBH, was added. The ordinate designates the secreted insulin level (ng/ml). The values are the mean+standard deviation (n=4). Symbol ** denotes p<0.01 (Student's t test vs. Base).

Based on the procedures of EXAMPLE 25, an essential prerequisite of $Ca^{2+}$ ions in the extracellular fluid was examined. In preincubation and incubation with a sample, $Ca^{2+}$ ions were removed and 0.1 mM EGTA, which was a reagent for chelating $Ca^{2+}$ ions, was further added, and then the insulin secretion enhancing activity by fatty acids was examined in this case. As a result, it was confirmed as shown in FIG. 29 that the insulin secretion enhancing activity by oleic acid, linoleic acid and γ-linolenic acid noted in ordinary buffer was not observed in the buffer containing no $Ca^{2+}$ ions but containing 0.1 mM EGTA. It was confirmed from the results that $Ca^{2+}$ ions were indispensable for the GPR40-mediated insulin secretion enhancing activity by fatty acids.

Example 30

Effects of Various Inhibitors on Insulin Secretion Mediated by GPR40

Figure 30:
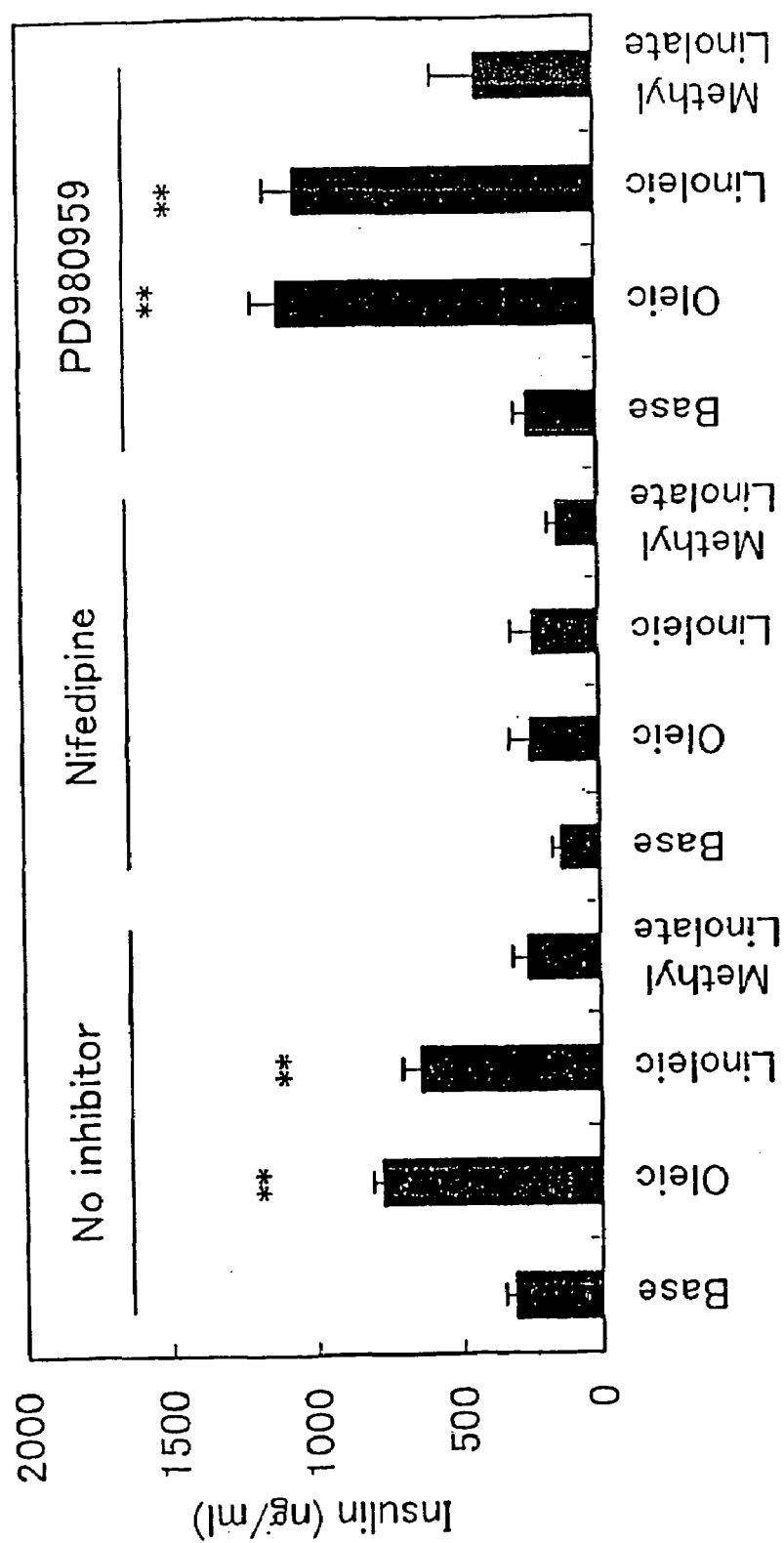
FIG. 30 shows the effects of various inhibitors on insulin secretion promotion from MIN6 by fatty acids. The abscissa designates the fatty acids added, wherein Base, Oleic, Linoleic and Methyl linolate denote no addition, oleic acid, linoleic acid and methyl linolate, respectively. The No inhibitor group indicates the case where the fatty acid (10 μM) prepared using 22 mM glucose-containing KRBH was added, the Nifedipine group indicates the case where the fatty acid (10 μM) prepared using 22 mM glucose-containing KRBH buffer supplemented with 10 μM of Nifedipine was added, and the PD98059 group indicates the case where the fatty acid (10 μM) prepared using 22 mM glucose-containing KRBH buffer supplemented with PD98059 (50 μM) was added. The ordinate designates the secreted insulin level (ng/ml). The values are the mean+standard deviation (n=4). Symbol ** denotes p<0.01 (Student's t test vs. Base).

Based on the method of EXAMPLE 25, effects of $Ca^{2+}$ channel blocker (Nifedipine) and MAP kinase inhibitor (PD98059) were examined. In preincubation and incubation with a sample, the insulin secretion enhancing activity by fatty acids was examined when Nifedipine (10 μM) or PD98059 (50 μM) was added. As shown in FIG. 30, the insulin secretion enhancing activity by oleic acid and linoleic acid, which was noted in ordinary buffer, was not appreciated in a buffer containing Nifedipine. This well matched the results when $Ca^{2+}$ ions were removed in EXAMPLE 29, again confirming that $Ca^{2+}$ ions were indispensable for the GPR40-mediated insulin secretion enhancing activity by the fatty acids. Furthermore, the same results as in ordinary buffer were obtained with PD98059-containing buffer, and this revealed that the insulin secretion enhancing activity occurred even in the state that MAP kinase was not activated, in other words, the MAP kinase activation induced by fatty acid stimulation is not necessarily required for the insulin secretion enhancing activity. It was likely that GPR40 would exert its functions not only for insulin secretion but also growth of β cells, etc.

Example 31

Effects of BSA on GPR40-Mediated Insulin Secretion

Figure 31:
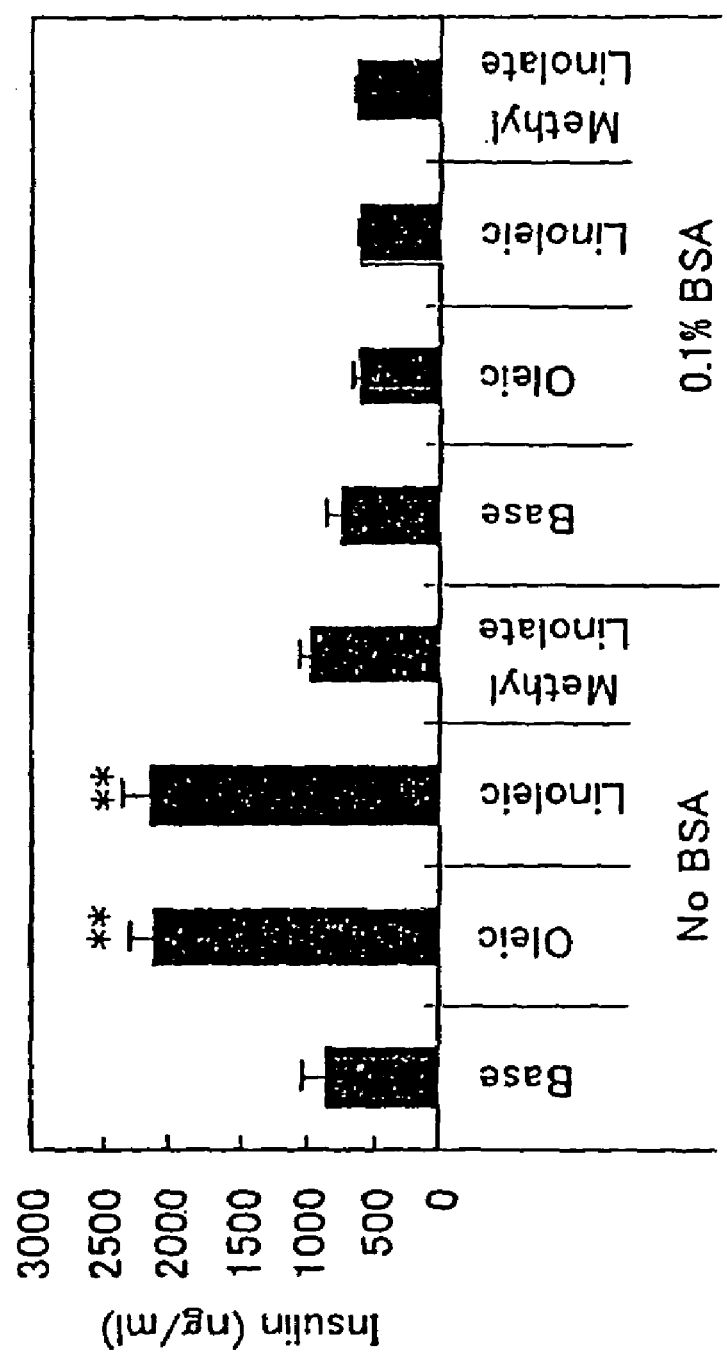
FIG. 31 shows the influence of BSA on insulin secretion promotion from MIN6 by fatty acids. The abscissa designates the fatty acids (10 μM) added, wherein Base, Oleic, Linoleic and Methyl linolate denote no addition, oleic acid, linoleic acid and methyl linolate, respectively. No BSA and 0.1% BSA indicate the conditions where BSA was not added to the buffer and the conditions where 0.1% BSA was added, respectively. The ordinate designates the secreted insulin level (ng/ml). The values are the mean+standard deviation (n=4). Symbol ** denotes p<0.01 (Student's t test vs. Base).

It is known that fatty acids have the property of binding to albumin. Based on the method of EXAMPLE 25, effects were examined when bovine serum albumin (BSA) was present. In preincubation and incubation with a sample, the insulin secretion activity by fatty acids was examined when 0.1% BSA was added to the buffer. As shown in FIG. 31, the insulin secretion activity by oleic acid and linoleic acid, which was noted in ordinary buffer, was almost suppressed in 0.1% fatty acid-free BSA-containing buffer. It was revealed that the insulin secretion activity was induced by the fatty acids which were not bound to BSA, rather than by the fatty acids bound to BSA. This indicates that the property of binding to BSA, which is inherent to fatty acids, is reflected in the reactivity.

Example 32

Determination of of Fatty Acids in Human-, Mouse- and Rat-Derived GPR40

For determination of $EC_{50}$ values, the CHO cell lines in which human-, mouse- and rat-derived GPR40 was stably expressed were used. Unless otherwise indicated, these CHO cell lines were incubated in α-MEM medium (Invitrogen) supplemented with 10% fetal calf serum (Invitrogen).

On the day before assay, the cells incubated to almost confluent stage were rinsed with PBS (Invitrogen), then scraped in 0.05% trypsin-EDTA solution (Invitrogen) and recovered by centrifugal operation. The number of the cells obtained was counted and diluted so as to contain $3 \times 10^5$ cells/1 mL of the medium. The dilution was dispensed in a Black welled 96-well plate (Coster) in 100 μL/well, followed by incubation overnight in a $CO_2$ incubator. To the thus prepared CHO cells, various test samples were added and the changes in intracellular calcium level in this case were measured using FLIPR (Molecular Device). In order to determine the changes in the intracellular calcium ion level on FLIPR, the cells were pre-treated by the following procedures.

First, for the purpose of adding a fluorescent dye Fluo-3 AM (DOJIN) to the cells or washing the cells immediately before the FLIPR assay, an assay buffer was prepared. A solution obtained by adding 20 mL of 1M HEPES (pH 7.4) (DOJIN) to 1000 mL of HBSS (Invitrogen) was prepared (hereinafter HBSS/HEPES solution), to which 10 mL of a solution mixture obtained by dissolving 710 mg of Probenecid (Sigma) in 5 mL of 1N NaOH and further adding 5 mL of HBSS/HEPES solution was added. The resulting solution was used as the assay buffer. Next, 50 μg of Fluo-3AM was dissolved in 21 μL of DMSO (Wako) and an equal volume of 20% Pulronic acid (Molecular Probes) was added to and mixed with the solution. The mixture was then added to 10.6 mL of the assay buffer supplemented with 105 μL of fetal calf serum to prepare a fluorescent dye solution. On the day before the assay, the medium for the CHO cells again plated in a Black welled 96-well plate was removed. Immediately thereafter, the fluorescent dye solution was dispensed in 100 μL each/well and the cells were incubated in a $CO_2$ incubator for an hour so that the fluorescent dye was taken up into the cells. The cells after the incubation was washed with the assay buffer described above and set on FLIPR. Test samples were prepared using the assay buffer, diluted to final concentrations of 30, 10, 3, 1 and 0.3 μM and set on FLIPR at the same time. After the pre-treatment above was made, the changes in intracellular calcium level after the addition of various test samples were measured on FLIPR. From these results, the dose-response curves for the respective fatty acids were prepared and the $EC_{50}$ values were calculated. The results are shown in TABLE 1.

TABLE 1

| Fatty | $EC_{50}$ μM | | |
|---|---|---|---|
| | Human GPR40 | Mouse GPR40 | Rat GPR40 |
| Acetic acid (C2) | inactive | inactive | inactive |
| Butyric acid (C4) | inactive | inactive | inactive |
| Caproic acid (C6) | inactive | inactive | >300 |
| Caprylic acid (C8) | >300 | inactive | >300 |
| Capric acid (C10) | 43 ± 2.2 | >100 | >100 |
| Lauric acid (C12) | 5.7 ± 1.4 | 5.6 ± 1.6 | 13 ± 3.3 |
| Myristic acid (C14) | 7.7 ± 1.4 | 6.0 ± 0.8 | 7.3 ± 0.5 |
| Palmitic acid (C16) | 6.8 ± 0.5 | 4.6 ± 1.2 | 6.6 ± 0.4 |
| Stearic acid (C18) | >300 | >300 | >300 |
| Oleic acid (C18:1) | 2.0 ± 0.3 | 2.7 ± 0.5 | 3.4 ± 0.4 |
| Elaidic acid (C18:1) | 4.7 ± 0.4 | 6.5 ± 1.5 | 11 ± 1.5 |
| Linoleic acid (C18:2) | 1.8 ± 0.1 | 2.9 ± 0.3 | 4.1 ± 0.5 |
| Methyl linolate | inactive | inactive | inactive |
| α-Linolenic acid (C18:3) | 2.0 ± 0.3 | 3.6 ± 0.3 | 4.0 ± 0.7 |
| γ-Linolenic acid (C18:3) | 4.6 ± 1.6 | 5.2 ± 0.6 | 5.4 ± 1.1 |
| Arachidonic acid (C20:4) | 2.4 ± 0.6 | 5.4 ± 0.8 | 8.0 ± 0.6 |
| Eicosapentaenoic acid (C20:5) | 2.3 ± 0.4 | 4.9 ± 0.8 | 9.8 ± 0.6 |
| Docosahexaenoic acid (C22:6) | 1.1 ± 0.3 | 16 ± 4.7 | 13 ± 1.7 |
| 5,6-Epoxyeicosatrienoic acid | 7.7 ± 0.2 | ND | ND |
| 8,9-Epoxyeicosatrienoic acid | 6.1 ± 0.2 | ND | ND |
| 11,12-Epoxyeicosatrienoic acid | 1.4 ± 0.3 | ND | ND |
| 14,15-Dihydroxyeicosatrienoic acid | 1.1 ± 0.4 | ND | ND |

ND is short for not determined.

Example 33

Figure 32:
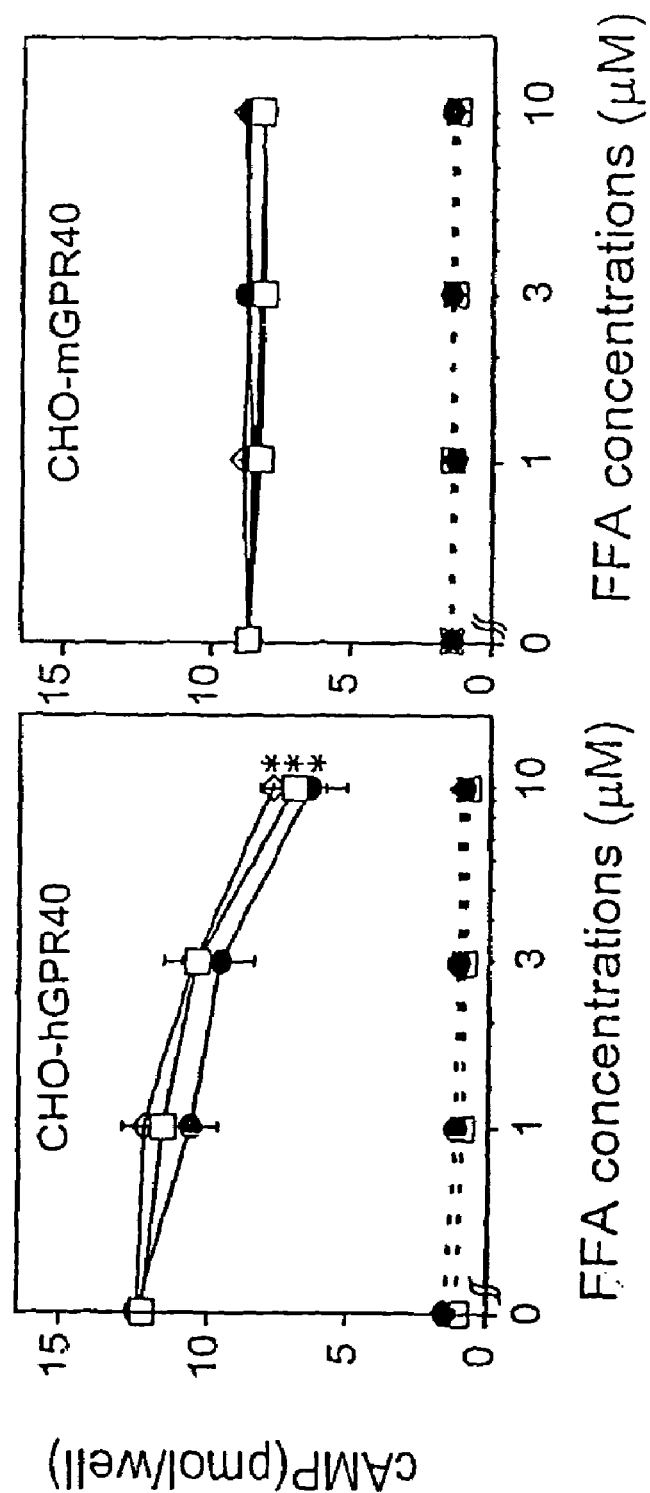
FIG. 32 shows the effects of various fatty acids on cAMP production in human GPR40-expressed CHO cells (CHO-hGPR40; left) and mouse GPR40-expressed CHO cells (CHO-mGPR40; right). FFA concentrations (μM) on the abscissa denote the concentrations of fatty acids added. The ordinate designates the cAMP level per well (pmol/well) in a 96-well plate. The solid line and the dotted line denote in the presence of 2 μM forskolin and in the absence of forskolin, respectively. Symbols closed circle, open diamond and open square denote the cases where docosahexaenoic acid (DHA), linoleic acid and γ-linolenic acid were added, respectively. Symbol * denotes p<0.05 (Student's t test).

Effects of Fatty Acids on cAMP Production in Human and Mouse GPR40-Expressed CHO Cells Human and mouse GPR40-expressed CHO cells were incubated for 20 hours in a 96-well Plate at a density of $1\times10^5$/well. After the cells were washed twice with 100 μl of Assay Buffer (DMEM (Invitrogen) containing 0.1 mM IBMX (Wako Pure Chemical) and 0.1 mM Ro-20-1724 (Biomol)), DHA, solutions of linoleic acid and γ-linoleic acid (both by SIGMA) in Assay Buffer in the presence or absence of 2 μM forskolin (Wako Pure Chemical) were added to the cells, followed by reacting at 37° C. for 10 minutes. After the reaction, the cells were lysed in accordance with the formulation of cAMP Screen (ABI) and the cAMP level in the cells was assayed. As a result, the respective fatty acids did not show any cAMP production activity on the human and mouse GPR40-expressed CHO cells in the absence of forskolin. On the other hand, the cAMP production activity was weakly shown on the human GPR40-expressed CHO cells in the presence of forskolin, whereas no activity was shown on the mouse GPR40-expressed CHO cells (FIG. 32).

Example 34

FLIPR Assay Using MIN6

Figure 33:
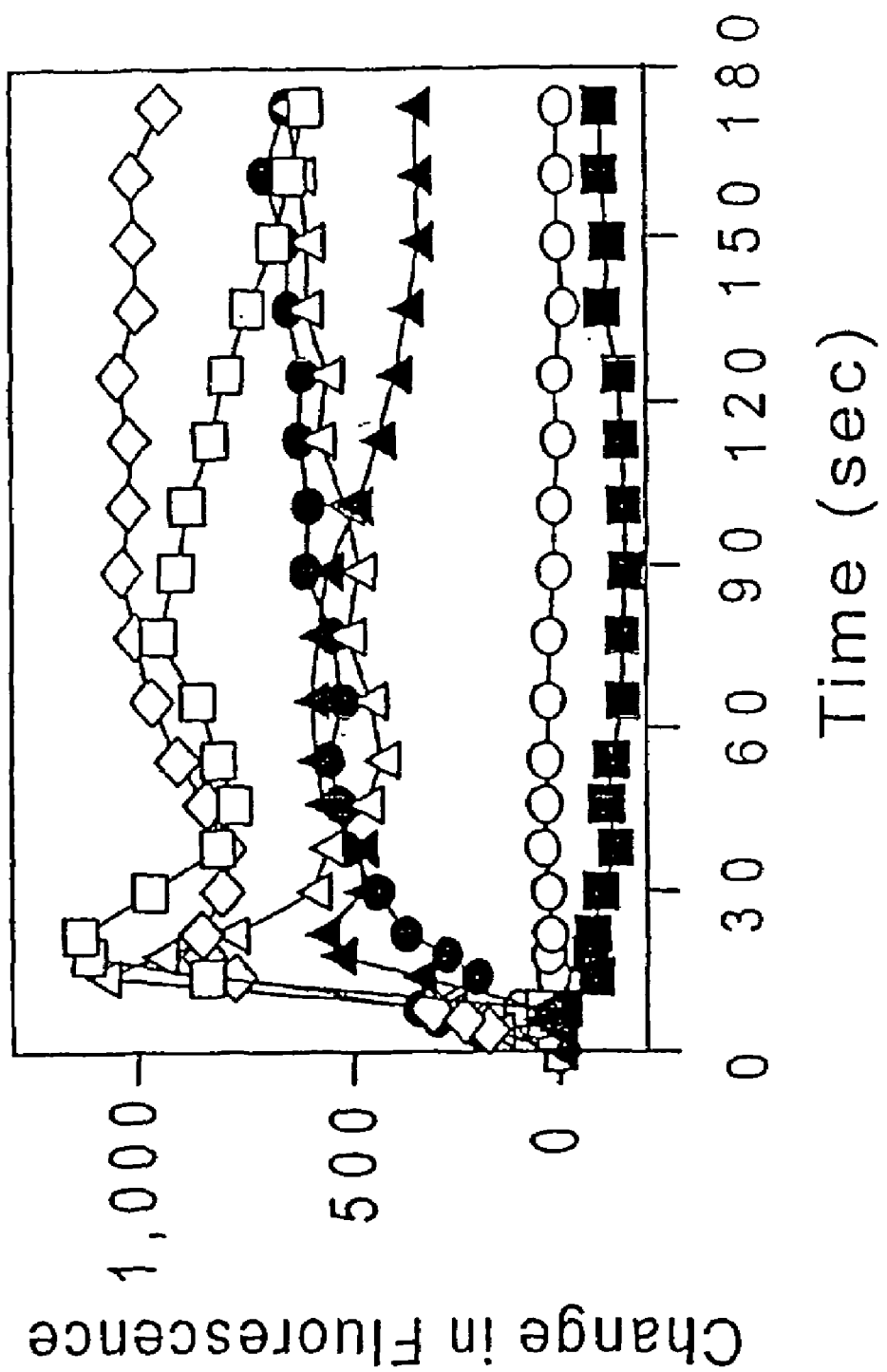
FIG. 33 shows the results of changes in intracellular $Ca^{2+}$ level examined when various fatty acids were added to MIN6 cells. The ordinate designates fluorescence intensity showing the intracellular $Ca^{2+}$ level and the abscissa designates the passage of time after a sample was added, wherein symbols open square, open diamond, closed square, open triangle, closed triangle, closed circle and open circle denote the cases where γ-linolenic acid, linoleic acid, methyl linolate, oleic acid, arachidonic acid, docosahexaenoic acid (DHA) and butyric acid were added, respectively.

Mouse pancreatic β cell line MIN6 incubated in a flask was scraped using PBS containing 2.5 mM EDTA and diluted so as to contain $3\times10^5$ cells/1 mL of the medium. The dilution was dispensed in a Black welled 96-well plate (Coster) in 100 μL/well, followed by incubation in a $CO_2$ incubator for 2 days. The medium used was 4.5 g/l of glucose-containing Dulbecco's Modified Eagle Medium (DMEM, Invitrogen, Inc.) supplemented with 15% fetal calf serum (ThermoTrace, Inc.), 5.5 μM 2-mercaptethanol (Invitrogen, Inc.), 20 mM HEPES pH 7.3, 100 U/ml penicillin and 100 μg/ml streptomycin. To the thus prepared MIN6 cells, various fatty acids (10 μM) were added and the changes in intracellular calcium level in this case were measured using FLIPR (Molecular Device). The changes in the intracellular calcium ion level on FLIPR were assayed in accordance with the procedures described in EXAMPLE 24. As a result, it was confirmed that the intracellular $Ca^{2+}$ level increased in MIN6 when γ-linolenic acid, linoleic acid, oleic acid, arachidonic acid and DHA, which are the ligands for GPR40, were added. On the other hand, such activity was not observed with methyl linolate or butyric acid, which is not the ligand for GPR40 (FIG. 33).

Example 35

Setting of the Screening Method for the Agonist and Antagonist to GPR40 and Criterion for Screening Agonist Candidate (1) Setting of the Screening Method for the Agonist and Antagonist to GPR40 Using the Changes in Intracellular Calcium Level as an Indicator In order to set up the survey system for the agonist and antagonist to GPR40, the assay system was set up using palmitic acid identified to be the agonist.

Human GPR40-expressed CHO cell line (CHO-hGPR40 No. 104) prepared by publicly known methods using human GPR40 expression vector prepared in REFERENCE EXAMPLE 1, was diluted so as to contain $3\times10^4$ cells/100 μl. The dilution was dispensed in a Black walled 96-well plate (Costar) in 100 μl each/well, followed by incubation overnight in a $CO_2$ incubator. Changes in intracellular calcium level were measured using FLIPR (Molecular Device), which procedures were described below.

In 21 μl of DMSO (DOJIN) 50 μg of Fluo-3AM (DOJIN) was dissolved and an equal volume of 20% Pulronic acid (Molecular Probes) was further added to and mixed with the solution. The mixture was then added to 10.6 ml of the assay buffer [which was prepared by adding 20 ml of 1M HEPES (pH 7.4) (DOJIN) to HBSS (Invitrogen) and further adding thereto 10 ml of a solution mixture, which was obtained by dissolving 710 mg of Probenecid (Sigma) in 5 ml of 1N NaOH and 5 ml of the HBSS/HEPES solution described above] supplemented with 105 µl of fetal calf serum to prepare a fluorescent dye solution. The medium in the cell plate was removed. Immediately thereafter, the fluorescent dye solution was dispensed in 100 µl each/well and the cells were incubated at 37° C. in a $CO_2$ incubator for an hour so that the fluorescent dye was taken up into the cells. The cells after the incubation was washed with the assay buffer described above. Palmitic acid added to the cells was diluted to various concentrations using the assay buffer and the dilution was dispensed onto the plate. For assaying the antagonist, 12 µM γ-linolenic acid solution (3 µM in the final concentration upon reaction) was dispensed onto the plate and at the same time, set on FLIPR. After the foregoing pre-treatment, the changes in intracellular calcium level after the addition of palmitic acid was measured on FRIPR to examine the agonist action, and then γ-linolenic acid was added to examine the antagonist action. Since palmitic acid is the agonist, the antagonist cannot be assessed in the experiment using palmitic acid, but when a compound having only the antagonist action is added, the activity of suppressing the reaction of γ-linolenic acid later added is observed. The $EC_{50}$ value was calculated from the dose-response curve using changes in fluorescent intensity value 30 seconds after or 40 seconds after the reaction commenced.

(2) Criterion for Screening the Agonist Candidate Based on the Results of FLIPR Assay Test compounds used to screen the agonist candidate were previously diluted with DMSO (Wako) to become 10 mM, which were used by diluting with the assay buffer described above upon the assay. Using these test compounds, the fluorescence intensity was assayed on the CHO cell line wherein human GPR40 prepared by publicly known methods using the human GPR40 expression vector prepared in REFERENCE EXAMPLE 1 was expressed (CHO-hGPR40 No. 104), the CHO cell line wherein human histamine H1 receptor prepared by publicly known methods using human histamine H1 receptor expression vector was expressed (CHO-H1) and Mock CHO cell line, 30 seconds or 40 seconds after the reaction commenced. In addition, when the fluorescence intensity of 30 µM γ-linolenic acid was made 100%, the relative value was calculated and the test compound showing the value of at least 50 or 100% based on GPR40 and satisfying 25% or less in both CHO cell lines of the human histamine H1 receptor and Mock was made a candidate for human GPR40-specific agonist.

Example 36

Suppressed Expression of Mouse GPR40 mRNA by Introducing siRNA Specific to the Sequence of Mouse GPR40

Figure 34:
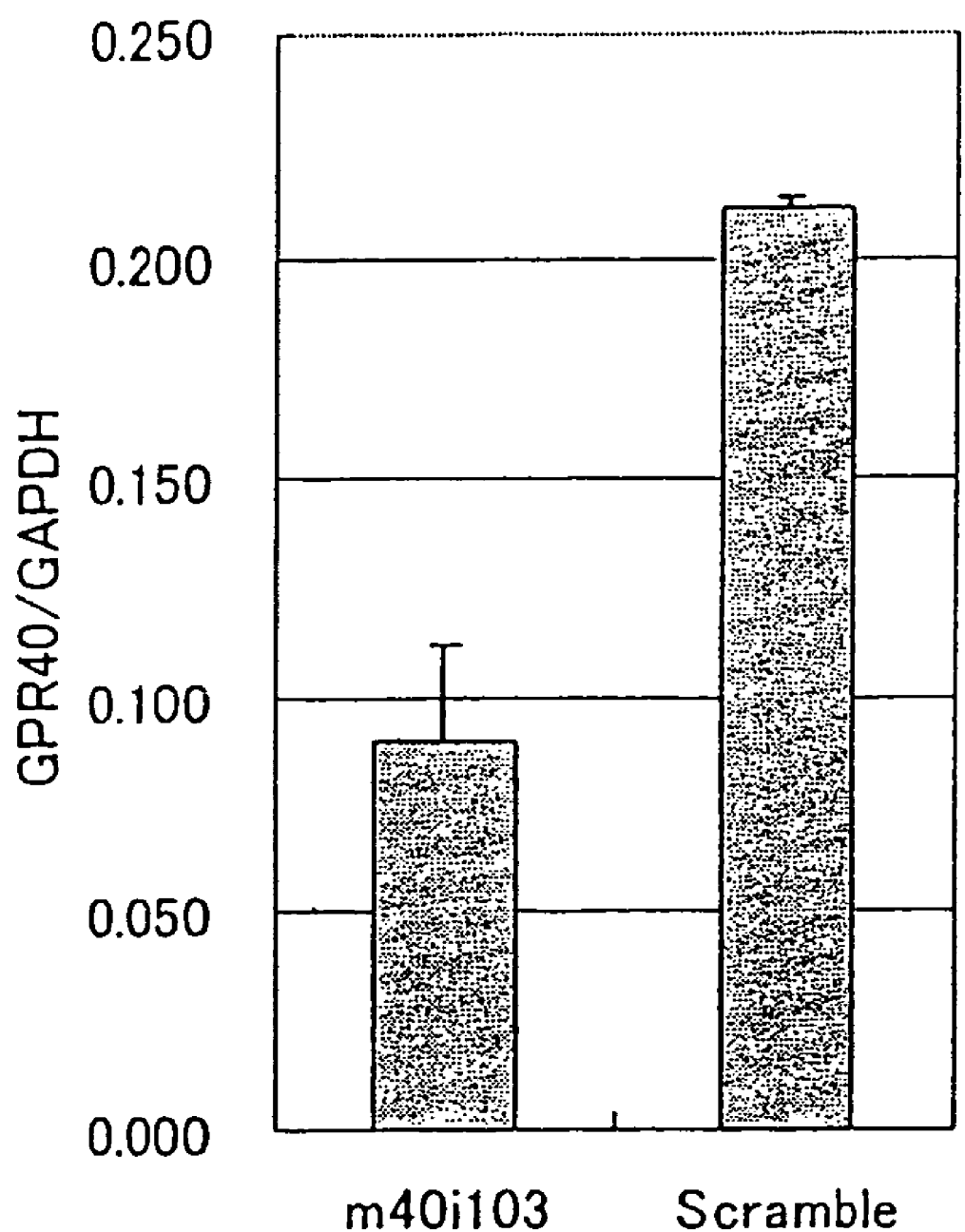
FIG. 34 shows the suppressed expression of mouse GPR40 mRNA by transfecting siRNA specific to the sequence of mouse GPR40. On the abscissa m40i103 denotes siRNA specific to mouse GPR40 and Scramble denotes Scramble II duplex siRNA of random sequence siRNAvfor control. On the ordinate, the expression level of mRNA (GRP40/GAPDH) denotes relative values (n=2+ SEM) of the expression level of GPR40 to GAPDH.

MIN6 cells were plated in a 24-well plate and incubated for a day. Based on the method of EXAMPLE 18, m40i103 or Scramble II duplex siRNA, which was a random sequence siRNA, was then introduced using HVJ Envelope VECTOR KIT GenomONE. After incubation for 2 days, the total RNA of the same cells was prepared in a manner similar to EXAMPLE 7, using Isogen (Nippon Gene K. K.), following the manual attached. Using as a primer 100 ng of random hexamer based on 1 µg of the resulting total RNA, cDNA was synthesized using SuperScriptII reverse transcriptase (Invitrogen, Inc.), which was lysed in 40 µl of TE buffer (pH 8.0). The expression levels of mouse GPR40 and mouse GAPDH mRNA were determined by the method described in EXAMPLE 4. As shown in FIG. 34, the results revealed that the expression of GPR40 mRNA decreased in the MIN6 cells introduced with m40i103, than in the MIN6 cells introduced with the random sequence siRNA.

INDUSTRIAL APPLICABILITY

The GPR40 of the present invention, its partial peptide, or a salt thereof, or the DNA encoding the GPR40 of the present invention or its partial peptide is useful as a preventive/therapeutic agent for diabetes mellitus, etc.

By using the GPR40 of the present invention, its partial peptide, or a salt thereof and a fatty acid which is the ligand, the compound that changes the binding properties of the fatty acid to the GPR40 of the present invention, its partial peptide, or a salt thereof can be screened efficiently.

Free Text for Sequence Identification

SEQ ID NO: 7

Designed oligonucleotide primer to amplify DNA encoding mGPR40

SEQ ID NO: 8

Designed oligonucleotide primer to amplify DNA encoding mGPR40

SEQ ID NO: 9

Designed oligonucleotide primer to amplify DNA encoding rGPR40

SEQ ID NO: 10

Designed oligonucleotide primer to amplify DNA encoding rGPR40

SEQ ID NO: 19

Designed oligonucleotide primer to amplify DNA encoding monkeyGPR40

SEQ ID NO: 20

Designed oligonucleotide primer to amplify DNA encoding monkeyGPR40

SEQ ID NO: 21

Designed oligonucleotide primer to amplify DNA encoding monkeyGPR40

SEQ ID NO: 22

Designed oligonucleotide primer to amplify DNA encoding monkeyGPR40

SEQ ID NO: 31

Designed oligonucleotide primer to amplify DNA encoding hamstarGPR40

SEQ ID NO: 32

Designed oligonucleotide primer to amplify DNA encoding hamstarGPR40

SEQ ID NO: 38

Designed oligonucleotide primer to amplify DNA encoding mouseGPR40

SEQ ID NO: 39

Designed oligonucleotide primer to amplify DNA encoding mouseGPR40.

The invention claimed is:

1. A method of screening insulin secretion promoting drug, which comprises:
   (a) contacting a G protein-coupled receptor protein to (i) a labeled form of a fatty acid or eicosanoid or (ii) a labeled form of a compound or its salt that changes the binding properties of the receptor protein to the fatty acid or eicosanoid;
   (b) contacting a G protein-coupled receptor protein to a test compound and (i) a labeled form of a fatty acid or eicosanoid or (ii) a labeled form of a compound or its salt that changes the binding properties of the receptor protein to the fatty acid or eicosanoid;
   (c) measuring the binding amount of (i) the labeled form of the fatty acid or eicosanoid or (ii) the labeled form of the compound or its salt that changes the binding properties of the receptor protein to the fatty acid or eicosanoid, to the G protein-coupled receptor protein in steps (a) and (b); and
   (d) comparing the level of the binding amount of the labeled form measured in step (c),
wherein, the fatty acid or eicosanoid is selected from farnesoic acid, 5.8.11.14-eicosatetraynoic acid, (+)14,15-dihydroxy-5Z,8Z,11Z-eicosatrienoic acid, (+)5(6)-epoxy-8Z,11Z,14Z-eicosatrienoic acid, (+)8(9)-epoxy-5Z,11Z,14Z-eicosatrienoic acid, (+)11(12)-epoxy-5Z,8Z,14Z-eicosatrienoic acid, (+)14(15)-epoxy-5Z,8Z,11Z-eicosatrienoic acid, Eicosapentaenoic acid, 5,6-Epoxyeicosatrienoic acid, 8,9-Epoxyeicosatrienoic acid, 11,12-Epoxyeicosatrienoic acid, and 14,15-Dihydroxyeicosatrienoic acid, and the test compound is a compound designed to bind, based on the atomic coordinate and the position of the ligand-binding pocket in the active site of a G protein-coupled receptor protein containing the amino acid sequence represented by SEQ ID NO: 5 or its salt, to the ligand-binding pocket.

2. A method of screening insulin secretion promoting drug, which comprises:
   (a) contacting a cell containing a G protein-coupled receptor protein or a membrane fraction of the cell to (i) a labeled form of a fatty acid or eicosanoid or (ii) a labeled form of a compound or its salt that changes the binding properties of the receptor protein to the fatty acid or eicosanoid;
   (b) contacting a cell containing a G protein-coupled receptor protein or a membrane fraction of the cell to a test compound and (i) a labeled form of a fatty acid or eicosanoid or (ii) a labeled form of a compound or its salt that changes the binding properties of the receptor protein to the fatty acid or eicosanoid;
   (c) measuring the binding amount of (i) the labeled form of the fatty acid or eicosanoid or (ii) the labeled form of the compound or its salt that changes the binding properties of the receptor protein to the fatty acid or eicosanoid, to the a cell containing a G protein-coupled receptor protein or a membrane fraction of the cell in steps (a) and (b); and
   (d) comparing the level of the binding amount of the labeled form measured in step (c),
wherein, the fatty acid or eicosanoid is selected from farnesoic acid, 5.8.11.14-eicosatetraynoic acid. (+)14,15-dihydroxy-5Z,8Z,11Z-eicosatrienoic acid, (+)5(6)-epoxy-8Z,11Z,14Z-eicosatrienoic acid, (+)8(9)-epoxy-5Z,11Z,14Z-eicosatrienoic acid, (+)11(12)-epoxy-5Z,8Z,14Z-eicosatrienoic acid, (+)14(15)-epoxy-5Z,8Z,11Z-eicosatrienoic acid, Eicosapentaenoic acid, 5,8-Epoxyeicosatrienoic acid, 8,9-Epoxyeicosatrienoic acid, 11,12-Epoxyeicosatrionoic acid, and 14,15-Dihydroxyeicosatrienoic acid, and the test compound is a compound designed to bind, based on the atomic coordinate and the position of the ligand-binding Pocket in the active site of a G protein-coupled receptor protein containing the amino acid sequence represented by SEQ ID NO: 5 or its salt, to the ligand-binding pocket.

3. A method of screening insulin secretion promoting drug, which comprises:
 (a) contacting a cell containing a G protein-coupled receptor protein or a membrane fraction of the cell to (i) a fatty acid or eicosanoid or (ii) a compound or its salt that changes the binding properties of the receptor protein to the fatty acid or eicosanoid;
 (b) contacting a cell containing a G protein-coupled receptor protein or a membrane fraction of the cell to a test compound and (i) a fatty acid or eicosanoid or (ii) a compound or its salt that changes the binding properties of the receptor protein to the fatty acid or eicosanoid;
 (c) assaying intracellular Ca2+ level increasing activity or the intracellular cAMP production suppressing activity in steps (a) and (b); and
 (d) comparing the intracellular Ca2+ level increasing activity or the intracellular cAMP production suppressing activity assayed in step (c), wherein, the fatty acid or eicosanoid is selected from farnesoic acid, 5.8.11.14-eicosatetraynoic, (+)14,15-dihydroxy-5Z,8Z,11Z-eicosatrienoic, (+)5(6)-epoxy-8Z,11Z, 14Z-eicosatrienoic acid, (+)8(9)-epoxy-5Z,11Z,14Z-eicosatrienoic acid, (+)11(12-epoxy-5Z,8Z,11Z-eicosatrienoic, (+)14(15)-epoxy-5Z,8Z,11Z-eicosatrienoic acid, Eicosapentaenoic acid, 5,6-Epoxyeicosatrienoic acid, 8,9-Epoxyeicosatrienoic acid, 11,12-Epoxyeicosatrienoic acid, and 14,15-Dihydroxyeioosatrienoic acid, and the test compound is a compound designed to bind, based on the atomic coordinate and the position of the ligand-binding pocket in the active site of a G protein-coupled receptor protein containing the amino acid sequence represented by SEQ ID NO: 5 or its salt, to the ligand-binding pocket.

* * * * *

SEQUENCE LISTING

<160> NUMBER OF SEQ ID NOS: 41

<210> SEQ ID NO 1
<211> LENGTH: 300
<212> TYPE: PRT
<213> ORGANISM: Mouse

<400> SEQUENCE: 1

```
Met Asp Leu Pro Pro Gln Leu Ser Phe Ala Leu Tyr Val Ser Ala Phe
                  5                  10                  15

Ala Leu Gly Phe Pro Leu Asn Leu Leu Ala Ile Arg Gly Ala Val Ser
                 20                  25                  30

His Ala Lys Leu Arg Leu Thr Pro Ser Leu Val Tyr Thr Leu His Leu
             35                  40                  45

Gly Cys Ser Asp Leu Leu Leu Ala Ile Thr Leu Pro Leu Lys Ala Val
         50                  55                  60

Glu Ala Leu Ala Ser Gly Ala Trp Pro Leu Pro Leu Pro Phe Cys Pro
 65                  70                  75                  80

Val Phe Ala Leu Ala His Phe Ala Pro Leu Tyr Ala Gly Gly Gly Phe
                 85                  90                  95

Leu Ala Ala Leu Ser Ala Gly Arg Tyr Leu Gly Ala Ala Phe Pro Phe
                100                 105                 110

Gly Tyr Gln Ala Ile Arg Arg Pro Arg Tyr Ser Trp Gly Val Cys Val
            115                 120                 125

Ala Ile Trp Ala Leu Val Leu Cys His Leu Gly Leu Ala Leu Gly Leu
        130                 135                 140

Glu Thr Ser Gly Ser Trp Leu Asp Asn Ser Thr Ser Ser Leu Gly Ile
145                 150                 155                 160

Asn Ile Pro Val Asn Gly Ser Pro Val Cys Leu Glu Ala Trp Asp Pro
                165                 170                 175

Asp Ser Ala Arg Pro Ala Arg Leu Ser Phe Ser Ile Leu Leu Phe Phe
            180                 185                 190

Leu Pro Leu Val Ile Thr Ala Phe Cys Tyr Val Gly Cys Leu Arg Ala
        195                 200                 205

Leu Val Arg Ser Gly Leu Ser His Lys Arg Lys Leu Arg Ala Ala Trp
    210                 215                 220

Val Ala Gly Gly Ala Leu Leu Thr Leu Leu Leu Cys Leu Gly Pro Tyr
225                 230                 235                 240

Asn Ala Ser Asn Val Ala Ser Phe Ile Asn Pro Asp Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Thr Gly Pro Gly Arg Gly Thr Ile
        275                 280                 285

Cys Val Thr Arg Thr Gln Arg Gly Thr Ile Gln Lys
    290                 295                 300
```

<210> SEQ ID NO 2
<211> LENGTH: 900
<212> TYPE: DNA
<213> ORGANISM: Mouse

<400> SEQUENCE: 2
atggacctgc ccccacagct ctccttcgct ctctatgtat ctgcctttgc gctgggcttt    60

```
ccattgaact tgttagccat ccgaggcgca gtgtcccacg ctaaactgcg actcactccc      120
agcttggtct acactctcca tctgggctgc tctgatctcc tactggccat cactctgccc      180
ctgaaggctg tggaggccct ggcttctgga gcctggcccc tgccgctccc cttctgccca      240
gtctttgcct tggcccactt tgctcccctc tacgcaggcg gaggcttcct agctgctctc      300
agcgctggcc gctacctggg ggctgccttc cccttcgggt accaagccat ccggaggccc      360
cgctattcct ggggtgtgtg tgtggctata tgggcccttg tcctctgcca cctggggctg      420
gcccttggct tggagacttc cggaagctgg ctggacaaca gtaccagttc cctgggcatc      480
aacatacccg tgaatggctc cccggtctgc ctggaagcct gggatcccga ctctgcccgc      540
cctgcccgtc tcagtttctc cattctgctc ttctttctgc ccttggtcat cactgccttc      600
tgctatgtgg gctgcctccg ggccctggtg cgctcaggcc tgagccacaa acggaagctc      660
agggcagctt gggtggccgg aggcgctctc ctcacactcc tgctctgcct ggggccctat      720
aatgcctcca atgtggctag tttcataaac ccggacctag gaggctcctg gaggaagttg      780
ggactcatca caggggcctg gagtgtggta ctcaacccac tggtcactgg ctacttggga      840
acaggtcctg gacggggaac aatatgtgtg acgaggactc aaagaggaac aattcagaag      900

<210> SEQ ID NO 3
<211> LENGTH: 300
<212> TYPE: PRT
<213> ORGANISM: Rat

<400> SEQUENCE: 3

Met Asp Leu Pro Pro Gln Leu Ser Phe Ala Leu Tyr Val Ser Ala Phe
                5                  10                  15

Ala Leu Gly Phe Pro Leu Asn Leu Leu Ala Ile Arg Gly Ala Val Ser
             20                  25                  30

His Ala Lys Leu Arg Leu Thr Pro Ser Leu Val Tyr Thr Leu His Leu
         35                  40                  45

Ala Cys Ser Asp Leu Leu Leu Ala Ile Thr Leu Pro Leu Lys Ala Val
     50                  55                  60

Glu Ala Leu Ala Ser Gly Val Trp Pro Leu Pro Leu Pro Phe Cys Pro
 65                  70                  75                  80

Val Phe Ala Leu Ala His Phe Ala Pro Leu Tyr Ala Gly Gly Gly Phe
                 85                  90                  95

Leu Ala Ala Leu Ser Ala Gly Arg Tyr Leu Gly Ala Ala Phe Pro Phe
            100                 105                 110

Gly Tyr Gln Ala Ile Arg Arg Pro Cys Tyr Ser Trp Gly Val Cys Val
        115                 120                 125

Ala Ile Trp Ala Leu Val Leu Cys His Leu Gly Leu Ala Leu Gly Leu
    130                 135                 140

Glu Ala Pro Arg Gly Trp Val Asp Asn Thr Thr Ser Ser Leu Gly Ile
145                 150                 155                 160

Asn Ile Pro Val Asn Gly Ser Pro Val Cys Leu Glu Ala Trp Asp Pro
                165                 170                 175

Asp Ser Ala Arg Pro Ala Arg Leu Ser Phe Ser Ile Leu Leu Phe Phe
            180                 185                 190

Leu Pro Leu Val Ile Thr Ala Phe Cys Tyr Val Gly Cys Leu Arg Ala
        195                 200                 205

Leu Val His Ser Gly Leu Ser His Lys Arg Lys Leu Arg Ala Ala Trp
    210                 215                 220

Val Ala Gly Gly Ala Leu Leu Thr Leu Leu Leu Cys Leu Gly Pro Tyr
```

```
                225                 230                 235                 240
Asn Ala Ser Asn Val Ala Ser Phe Ile Asn Pro Asp Leu Glu Gly Ser
                    245                 250                 255
Trp Arg Lys Leu Gly Leu Ile Thr Gly Ala Trp Ser Val Val Leu Asn
            260                 265                 270
Pro Leu Val Thr Gly Tyr Leu Gly Thr Gly Pro Gly Gln Gly Thr Ile
        275                 280                 285
Cys Val Thr Arg Thr Pro Arg Gly Thr Ile Gln Lys
    290                 295                 300

<210> SEQ ID NO 4
<211> LENGTH: 900
<212> TYPE: DNA
<213> ORGANISM: Rat

<400> SEQUENCE: 4
atggacctgc ccccacagct ctccttcgct ctctatgtat cagcctttgc actaggcttt      60
ccattgaact tgttagccat ccgaggtgca gtgtcccacg cgaaactgcg actcaccccc     120
agcttggtct acactctcca tttggcctgc tctgacctcc tactggccat caccctgccc     180
ctgaaggctg tggaggccct ggcttctggg gtctggcccc tgccactccc cttctgccca     240
gtctttgcct ggcccacttt gcgcccctc tatgcaggtg gaggcttcct ggctgctctc      300
agtgctggcc gctacctggg agctgccttc ccctttggat accaagccat ccggaggccc     360
tgctattcct ggggtgtgtg tgtggctata tgggcccttg tcctttgcca cctgggactg     420
gctcttggct tggaggctcc cagaggctgg gtggataaca ccaccagttc cctgggcatc     480
aacatacccg tgaatggctc cccggtctgc ctggaagcgt gggatcctga ctctgcccgc     540
cctgcccgac tcagtttctc gattctgctc ttctttctgc ccttggttat cactgctttc     600
tgctatgtgg gctgcctccg ggccctggtg cactcgggcc tgagccacaa acggaagctc     660
agggcagctt gggtggctgg aggagcactt ctcacactcc tgctctgcct ggggccctat     720
aatgcttcca atgtggctag tttcataaac ccggacttag aaggctcctg gaggaagttg     780
gggctcatca caggagcctg gagtgtggtg ctcaacccac tggtcactgg ctacttggga     840
acaggtcctg gacaggggac aatatgtgtg accaggactc aagagggac aattcagaag     900

<210> SEQ ID NO 5
<211> LENGTH: 300
<212> TYPE: PRT
<213> ORGANISM: Human

<400> SEQUENCE: 5

Met Asp Leu Pro Pro Gln Leu Ser Phe Gly Leu Tyr Val Ala Ala Phe
                5                   10                  15
Ala Leu Gly Phe Pro Leu Asn Val Leu Ala Ile Arg Gly Ala Thr Ala
            20                  25                  30
His Ala Arg Leu Arg Leu Thr Pro Ser Leu Val Tyr Ala Leu Asn Leu
        35                  40                  45
Gly Cys Ser Asp Leu Leu Thr Val Ser Leu Pro Leu Lys Ala Val
    50                  55                  60
Glu Ala Leu Ala Ser Gly Ala Trp Pro Leu Pro Ala Ser Leu Cys Pro
65                  70                  75                  80
Val Phe Ala Val Ala His Phe Phe Pro Leu Tyr Ala Gly Gly Gly Phe
                85                  90                  95
Leu Ala Ala Leu Ser Ala Gly Arg Tyr Leu Gly Ala Ala Phe Pro Leu
```

```
                    100                 105                 110
Gly Tyr Gln Ala Phe Arg Arg Pro Cys Tyr Ser Trp Gly Val Cys Ala
            115                 120                 125

Ala Ile Trp Ala Leu Val Leu Cys His Leu Gly Leu Val Phe Gly Leu
130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Leu Phe Phe
            180                 185                 190

Leu Pro Leu Ala Ile Thr Ala Phe Cys Tyr Val Gly Cys Leu Arg Ala
            195                 200                 205

Leu Ala Arg Ser Gly Leu Thr His Arg Arg Lys Leu Arg Ala Ala Trp
            210                 215                 220

Val Ala Gly Gly Ala Leu Leu Thr Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
            275                 280                 285

Cys Ala Ala Arg Thr Gln Gly Gly Lys Ser Gln Lys
            290                 295                 300

<210> SEQ ID NO 6
<211> LENGTH: 900
<212> TYPE: DNA
<213> ORGANISM: Human

<400> SEQUENCE: 6
atggacctgc cccgcagct ctccttcggc ctctatgtgg ccgcctttgc gctgggcttc      60
ccgctcaacg tcctggccat ccgaggcgcg acggcccacg cccggctccg tctcaccct     120 agcctggtct acgccctgaa cctgggctgc tccgacctgc tgctgacagt ctctctgccc    180
ctgaaggcgg tggaggcgct agcctccggg gcctggcctc tgccggcctc gctgtgcccc    240
gtcttcgcgg tggcccactt cttcccactc tatgccggcg ggggcttcct ggccgccctg    300
agtgcaggcc gctacctggg agcagccttc ccttgggct accaagcctt ccggaggcc      360 tgctattcct gggggtgtg cgcggccatc tgggccctcg tcctgtgtca cctgggtctg    420
gtctttgggt tggaggctcc aggaggctgg ctggaccaca gcaacacctc cctgggcatc    480
aacacaccgg tcaacggctc tccggtctgc ctggaggcct gggaccgggc tctgccggc     540 ccggcccgct tcagcctctc tctcctgctc ttttttctgc ccttggccat cacagccttc    600
tgctacgtgg gctgcctccg ggcactggcc cgctccggcc tgacgcacag gcggaagctg    660
cgggccgcct gggtggccgg cggggccctc ctcacgctgc tgctctgcgt aggaccctac    720
aacgcctcca acgtggccag cttcctgtac cccaatctag gaggctcctg gcggaagctg    780 ggctcatca cggtgcctg gagtgtggtg cttaatccgc tggtgaccgg ttacttggga     840 agggtcctg gcctgaagac agtgtgtgcg gcaagaacgc aaggggcaa gtcccagaag     900

<210> SEQ ID NO 7
<211> LENGTH: 41
```

```
<212> TYPE: DNA
<213> ORGANISM: Artificial Sequence
<220> FEATURE:
<223> OTHER INFORMATION: Designed oligonucleotide primer to amplify DNA
      encoding mGRP40

<400> SEQUENCE: 7
gtcgaccacc atggacctgc ccccacagct ctccttcgct c                     41

<210> SEQ ID NO 8
<211> LENGTH: 38
<212> TYPE: DNA
<213> ORGANISM: Artificial Sequence
<220> FEATURE:
<223> OTHER INFORMATION: Designed oligonucleotide primer to amplify DNA
      encoding mGRP40

<400> SEQUENCE: 8
actagtctac ttctgaattg ttcctctttg agtcctcg                         38

<210> SEQ ID NO 9
<211> LENGTH: 41
<212> TYPE: DNA
<213> ORGANISM: Artificial Sequence
<220> FEATURE:
<223> OTHER INFORMATION: Designed oligonucleotide primer to amplify DNA
      encoding rGRP40

<400> SEQUENCE: 9
gtcgaccacc atggacctgc ccccacagct ctccttcgct c                     41

<210> SEQ ID NO 10
<211> LENGTH: 38
<212> TYPE: DNA
<213> ORGANISM: Artificial Sequence
<220> FEATURE:
<223> OTHER INFORMATION: Designed oligonucleotide primer to amplify DNA
      encoding rGRP40

<400> SEQUENCE: 10
actagtctac ttctgaattg tccctcttgg agtcctgg                         38

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
gcccgcttca gcctctct                                               18

<210> SEQ ID NO 12
<211> LENGTH: 23
<212> TYPE: DNA
<213> ORGANISM: Artificial Sequence
<220> FEATURE:
<223> OTHER INFORMATION: probe

<400> SEQUENCE: 12
tctgcccttg gccatcacag cct                                         23

<210> SEQ ID NO 13
<211> LENGTH: 18
<212> TYPE: DNA
<213> ORGANISM: Artificial Sequence
<220> FEATURE:
```

-continued

<223> OTHER INFORMATION: primer

<400> SEQUENCE: 13
gaggcagccc acgtagca                                                18

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
ggctttccat tgaacttgtt agc                                          23

<210> SEQ ID NO 15
<211> LENGTH: 27
<212> TYPE: DNA
<213> ORGANISM: Artificial Sequence
<220> FEATURE:
<223> OTHER INFORMATION: probe

<400> SEQUENCE: 15
tgtcccacgc taaactgcga ctcactc                                      27

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
cccagatgga gagtgtagac caa                                          23

<210> SEQ ID NO 17
<211> LENGTH: 300
<212> TYPE: PRT
<213> ORGANISM: Monkey

<400> SEQUENCE: 17

Met Asp Leu Pro Pro Gln Leu Ser Phe Ala Leu Tyr Val Ala Ala Phe
              5                  10                  15

Ala Leu Gly Phe Pro Leu Asn Val Leu Ala Ile Arg Gly Ala Arg Ala
         20                  25                  30

His Ala Arg Arg Arg Leu Thr Pro Ser Leu Val Tyr Ala Leu Asn Leu
     35                  40                  45

Gly Cys Ser Asp Leu Leu Leu Thr Val Ser Leu Pro Leu Lys Ala Val
 50                  55                  60

Glu Ala Leu Ala Ser Gly Ala Trp Pro Leu Pro Ala Ser Leu Cys Pro
 65                  70                  75                  80

Val Phe Gly Val Ala His Phe Ala Pro Leu Tyr Ala Gly Gly Gly Phe
                 85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Val Leu
    130                 135                 140

Glu Ala Pro Gly Gly Trp Leu Asp His Ser Asn Thr Ser Leu Gly Ile
145                 150                 155                 160

```
Asn Thr Pro Val Asn Gly Ser Pro Val Cys Leu Glu Ala Trp Asp Pro
                165                 170                 175
Ala Ser Ala Gly Pro Ala Arg Phe Ser Leu Ser Leu Leu Phe Phe
            180                 185                 190
Leu Pro Leu Ala Ile Thr Ala Phe Cys Tyr Val Gly Cys Leu Arg Ala
        195                 200                 205
Leu Ala His Ser Gly Leu Thr His Arg Arg Lys Leu Arg Ala Ala Trp
    210                 215                 220
Val Ala Gly Gly Ala Leu Leu Thr Leu Leu Cys Val Gly Pro Tyr
225                 230                 235                 240
Asn Ala Ser Asn Val Ala Ser Phe Leu Asn Pro Asn Leu Gly Ser
                245                 250                 255
Trp Arg Lys Leu Gly Leu Ile Thr Gly Ala Trp Ser Val Val Leu Asn
                260                 265                 270
Pro Leu Val Thr Gly Tyr Leu Gly Arg Gly Pro Gly Leu Lys Thr Val
            275                 280                 285
Cys Ala Ala Arg Thr Gln Gly Ser Thr Ser Gln Lys
290                 295                 300

<210> SEQ ID NO 18
<211> LENGTH: 900
<212> TYPE: DNA
<213> ORGANISM: Monkey

<400> SEQUENCE: 18
atggacctgc ccccgcagct ctcctttgcc ctctatgtgg cggcctttgc gctgggcttc      60
ccgctcaacg tcctggccat ccgaggggcg agggcccacg cccggcgccg tctcaccccc     120
agcctggtct acgccctgaa cctgggctgc tccgacctgt tgctgacagt ctccctgccc     180
ctgaaggcgg tggaggcgct ggcctccggg gcctggcctc tgccggcctc actgtgccct     240
gtcttcgggg tggcccactt tgctccactc tatgccggcg ggggcttcct ggccgccctg     300
agtgcaggcc gctacctggg agcggccttc cccttgggct accaagcctt ccggaggccg     360
tgctattcct gggggggtgtg tgcggccatc tgggccctcg tcctgtgtca cctgggtctg     420
gtctttgtgt tggaggctcc gggaggctgg ctggaccaca gcaacacctc actgggcatc     480
aacacaccgg tcaacggctc tcccgtctgc ctggaggcct gggacccggc tctgccggc      540
ccggcccgct tcagcctctc tctcctgctt ttttttcctgc ccttggccat cacagccttc     600
tgctacgtgg gctgcctccg ggcactggcc cactccggcc tgacccacag gcggaagctg     660
agggccgcct gggtagccgg cggggcccctc ctcacgctgc tgctctgcgt aggaccctac     720
aacgcctcca atgtggccag cttctgaac cccaatctgg gaggctcctg gcggaagctg     780
ggctcatca cgggtgcctg gagtgtggtg ctcaacccgc tggtgaccgg ttacttggga     840
aggggtcctg gcctgaagac agtgtgtgcg gcaagaacgc aagggagcac gtcccagaag     900

<210> SEQ ID NO 19
<211> LENGTH: 24
<212> TYPE: DNA
<213> ORGANISM: Artificial Sequence
<220> FEATURE:
<223> OTHER INFORMATION: Designed oligonucleotide primer to amplify DNA
      encoding monkeyGRP40

<400> SEQUENCE: 19
tttctctgtg ggcctcgttt cctc       24
```

<210> SEQ ID NO 20
<211> LENGTH: 23
<212> TYPE: DNA
<213> ORGANISM: Artificial Sequence
<220> FEATURE:
<223> OTHER INFORMATION: Designed oligonucleotide primer to amplify DNA
      encoding monkeyGRP40

<400> SEQUENCE: 20
cgtgctctgg ctcggtgctc ctc                                    23

<210> SEQ ID NO 21
<211> LENGTH: 20
<212> TYPE: DNA
<213> ORGANISM: Artificial Sequence
<220> FEATURE:
<223> OTHER INFORMATION: Designed oligonucleotide primer to amplify DNA
      encoding monkeyGRP40

<400> SEQUENCE: 21
ggcctcgttt cctccctgat                                        20

<210> SEQ ID NO 22
<211> LENGTH: 24
<212> TYPE: DNA
<213> ORGANISM: Artificial Sequence
<220> FEATURE:
<223> OTHER INFORMATION: Designed oligonucleotide primer to amplify DNA
      encoding monkeyGRP40

<400> SEQUENCE: 22
gccctcctgc cccatgctcc ttcc                                   24

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
cacagctctc cttcgctctc tat                                    23

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
cagtttcgcg tgggacact                                         19

<210> SEQ ID NO 25
<211> LENGTH: 30
<212> TYPE: DNA
<213> ORGANISM: Artificial Sequence
<220> FEATURE:
<223> OTHER INFORMATION: probe

<400> SEQUENCE: 25
tcagcctttg cactaggctt tccattgaac                             30

<210> SEQ ID NO 26
<211> LENGTH: 18
<212> TYPE: DNA

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 26
gcccgcttca gcctctct                                               18

<210> SEQ ID NO 27
<211> LENGTH: 18
<212> TYPE: DNA
<213> ORGANISM: Artificial Sequence
<220> FEATURE:
<223> OTHER INFORMATION: probe

<400> SEQUENCE: 27
gaggcagccc acgtagca                                               18

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
ctgctttttt tcctgcccttt ggcc                                       24

<210> SEQ ID NO 29
<211> LENGTH: 300
<212> TYPE: PRT
<213> ORGANISM: Hamster

<400> SEQUENCE: 29

Met Ala Leu Ser Pro Gln Leu Phe Phe Ala Leu Tyr Val Ser Ala Phe
                 5                  10                  15

Ala Leu Gly Phe Pro Leu Asn Leu Leu Ala Ile Arg Gly Ala Val Ala
             20                  25                  30

Arg Ala Arg Leu Arg Leu Thr Pro Asn Leu Val Tyr Thr Leu His Leu
         35                  40                  45

Ala Cys Ser Asp Leu Leu Leu Ala Ile Thr Leu Pro Val Lys Ala Val
     50                  55                  60

Glu Ala Leu Ala Ser Gly Ala Trp Pro Leu Pro Leu Pro Leu Cys Pro
 65                  70                  75                  80

Val Phe Val Leu Val His Phe Ala Pro Leu Tyr Ala Gly Gly Gly Phe
                 85                  90                  95

Leu Ala Ala Leu Ser Ala Gly Arg Tyr Leu Gly Ala Ala Phe Pro Phe
            100                 105                 110

Gly Tyr Gln Ala Val Arg Arg Pro Arg Tyr Ser Trp Gly Val Cys Val
        115                 120                 125

Ala Ile Trp Ala Leu Val Leu Cys His Met Gly Leu Val Leu Gly Leu
    130                 135                 140

Glu Ala Pro Gly Gly Trp Leu Asn Thr Thr Ser Ser Ser Leu Gly Ile
145                 150                 155                 160

Asn Thr Pro Val Asn Gly Ser Pro Val Cys Leu Glu Ala Trp Asp Pro
                165                 170                 175

Asn Ser Ala Arg Pro Ala Arg Leu Ser Phe Ser Ile Leu Leu Phe Phe
            180                 185                 190

Val Pro Leu Val Ile Thr Ala Phe Cys Tyr Val Gly Cys Leu Arg Ala
        195                 200                 205

```
Leu Ala His Ser Gly Leu Ser His Lys Arg Lys Leu Arg Ala Ala Trp
    210                 215                 220
Ala Ala Gly Gly Ala Phe Leu Thr Leu Leu Leu Cys Leu Gly Pro Tyr
225                 230                 235                 240
Asn Ala Ser Asn Val Ala Ser Phe Val Asn Pro Asp Leu Gly Gly Ser
                245                 250                 255
Trp Arg Lys Leu Gly Leu Ile Thr Gly Ser Trp Ser Val Val Leu Asn
            260                 265                 270
Pro Leu Val Thr Gly Tyr Leu Gly Ala Ser Pro Gly Arg Gly Thr Val
        275                 280                 285
Cys Thr Thr Arg Thr Gln Gly Gly Thr Ile Gln Lys
    290                 295                 300

<210> SEQ ID NO 30
<211> LENGTH: 900
<212> TYPE: DNA
<213> ORGANISM: Hamstar

<400> SEQUENCE: 30
atggccctgt ctccccaact cttcttcgcc ctctatgtgt ctgccttcgc gctgggcttc      60
ccgctgaacc tgttggccat ccgaggcgcc gtggcccgtg caaggctgcg gctcaccccc     120
aacctggtct atacactcca cctggcctgc tctgacctgc tcctggccat cacgctaccc     180
gtgaaggccg tggaggccct ggcttctggg gcctggcccc tgccgctccc cttgtgccct     240
gtctttgtct tggtgcactt cgccccactc tatgcgggcg gaggcttcct ggcggctctc     300
agtgctggcc gctacctggg ggctgccttc cccttcgggt accaagccgt tcggcggccc     360
cgctactcct ggggcgtgtg tgtggctata tgggcccttg tcctctgcca catggggctg     420
gtcctcggct tggaggctcc cggaggctgg ctgaacacca ccagcagctc cctgggaatc     480
aacacaccgg tgaatggttc cccggtgtgc ctggaagcct gggatcccaa ctctgcccgg     540
cctgcccgcc tcagtttctc catcctgctc ttcttcgtgc cctggtcat caccgccttc     600
tgctacgtgg gctgcctgcg ggctctggcc cactcgggcc tgagccacaa acggaagctc     660
agggcagcct gggcggccgg aggggccttt ctcacactcc tgctctgctt ggggccctac     720
aatgcctcca atgtggcgag tttcgtaaac ccggacctgg gaggctcctg aggaagctg     780
gggctcatca cagggtcctg gagtgtggta ctcaacccgc tggtcaccgg ttacttggga     840
gcaagtcctg gccgagggac agtatgtacg acaaggactc aaggaggaac aattcagaag     900

<210> SEQ ID NO 31
<211> LENGTH: 33
<212> TYPE: DNA
<213> ORGANISM: Artificial Sequence
<220> FEATURE:
<223> OTHER INFORMATION: primer 1

<400> SEQUENCE: 31
gtcgacgacg agaggcaccc actcggcccc atg                                    33

<210> SEQ ID NO 32
<211> LENGTH: 33
<212> TYPE: DNA
<213> ORGANISM: Artificial Sequence
<220> FEATURE:
<223> OTHER INFORMATION: primer 2

<400> SEQUENCE: 32
gctagcctac ttctgaattg ttcctccttg agt                                    33
```

```
<210> SEQ ID NO 33
<211> LENGTH: 12
<212> TYPE: PRT
<213> ORGANISM: Human

<400> SEQUENCE: 33

Cys Ala Ala Arg Thr Gln Gly Gly Lys Ser Gln Lys
 1               5                  10

<210> SEQ ID NO 34
<211> LENGTH: 21
<212> TYPE: RNA
<213> ORGANISM: Artificial Sequence
<220> FEATURE:
<221> NAME/KEY: misc_feature
<222> LOCATION: (20), (21)
<223> OTHER INFORMATION: n stands for deoxy ribothymidine

<400> SEQUENCE: 34
cgccaguugu gacauucuun n                                         21

<210> SEQ ID NO 35
<211> LENGTH: 21
<212> TYPE: RNA
<213> ORGANISM: Artificial Sequence
<220> FEATURE:
<221> NAME/KEY: misc_feature
<222> LOCATION: (1), (2)
<223> OTHER INFORMATION: n stands for deoxy ribothymidine

<400> SEQUENCE: 35
nngcggucaa cacuguaaga a                                         21

<210> SEQ ID NO 36
<211> LENGTH: 21
<212> TYPE: RNA
<213> ORGANISM: Artificial Sequence
<220> FEATURE:
<221> NAME/KEY: misc_feature
<222> LOCATION: (20), (21)
<223> OTHER INFORMATION: n stands for deoxy ribothymidine

<400> SEQUENCE: 36
cuuguuagcc auccgaggcn n                                         21

<210> SEQ ID NO 37
<211> LENGTH: 21
<212> TYPE: DNA
<213> ORGANISM: Artificial Sequence
<220> FEATURE:
<221> NAME/KEY: misc_feature
<222> LOCATION: (1), (2)
<223> OTHER INFORMATION: n stands for deoxy ribothymidine

<400> SEQUENCE: 37
nngaacaatc ggtaggctcc g                                         21

<210> SEQ ID NO 38
<211> LENGTH: 27
<212> TYPE: DNA
<213> ORGANISM: Artificial Sequence
<220> FEATURE:
<223> OTHER INFORMATION: primer

<400> SEQUENCE: 38
gtcgacaagc agtgaactcg gggtctc                                   27
```

```
<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
gtcgacagat cagaactgag cttcccgtca                                     30

<210> SEQ ID NO 40
<211> LENGTH: 33
<212> TYPE: DNA
<213> ORGANISM: Artificial Sequence
<220> FEATURE:
<223> OTHER INFORMATION: primer for sense strand

<400> SEQUENCE: 40
cgtcgacccg gcggccccat ggacctgccc ccg                                 33

<210> SEQ ID NO 41
<211> LENGTH: 33
<212> TYPE: DNA
<213> ORGANISM: Artificial Sequence
<220> FEATURE:
<223> OTHER INFORMATION: primer for antisense strand

<400> SEQUENCE: 41
catcgattag cagtggcgtt acttctggga ctt                                 33
```